(12) United States Patent
Thomas et al.

(10) Patent No.: US 8,268,586 B2
(45) Date of Patent: Sep. 18, 2012

(54) MODIFIED MESSENGER RNA STABILIZING SEQUENCES FOR EXPRESSING GENES IN BACTERIAL CELLS

(75) Inventors: Michael Thomas, Davis, CA (US);
Gloria Erichsen, Davis, CA (US);
William Widner, Davis, CA (US)

(73) Assignee: Novozymes, Inc., Davis, CA (US)

( * ) Notice: Subject to any disclaimer, the term of this patent is extended or adjusted under 35 U.S.C. 154(b) by 376 days.

(21) Appl. No.: 12/520,072

(22) PCT Filed: Dec. 19, 2007

(86) PCT No.: PCT/US2007/088060
§ 371 (c)(1),
(2), (4) Date: Jul. 2, 2009

(87) PCT Pub. No.: WO2008/140615
PCT Pub. Date: Nov. 20, 2008

(65) Prior Publication Data
US 2010/0028943 A1 Feb. 4, 2010

Related U.S. Application Data

(60) Provisional application No. 60/876,894, filed on Dec. 21, 2006.

(51) Int. Cl.
*C12P 21/02* (2006.01)
(52) U.S. Cl. .................. 435/69.1; 435/252.31; 435/485
(58) Field of Classification Search ........................ None
See application file for complete search history.

(56) References Cited

U.S. PATENT DOCUMENTS

| 5,955,310 A | 9/1999 | Widner et al. |
| 6,255,076 B1 | 7/2001 | Widner et al. |

FOREIGN PATENT DOCUMENTS
WO 9943835 A2 9/1999

OTHER PUBLICATIONS

Daguer et al., 2005, Lett Appl Microbiol 41, 221-22.
Dimari et al., 1993, Mol Microbiol 7 (5). 705-717.
Hue et al., 1995, J Bacteriol 177 (12), 3465-3471.
Regnier et al., 2000, Bioessays 22: 235-244.
Steege et al., 2000, RNA 6: 1079-1090.
Hambraeus et al., 2002, Microbiology 148: 1795-1803.
Sharp et al., 2003, J. Bacteriology, v. 185, p. 5372-5379.
Agaisse et al., 1996, Mol. Microbiol. 20: 633-643.
Wu et al., 1991, J. Bacteriology, v. 173, p. 4952-4958.

*Primary Examiner* — Jim Ketter
(74) *Attorney, Agent, or Firm* — Eric J. Fechter; Robert L. Starnes

(57) ABSTRACT

The present invention relates to methods of producing a polypeptide having biological activity in a bacterial cell, comprising: (a) cultivating a bacterial host cell in a medium conducive for production of the polypeptide, wherein the bacterial host cell comprises a nucleic acid construct comprising a promoter region operably linked to a polynucleotide sequence encoding the polypeptide and a modified mRNA processing/stabilizing sequence located downstream of the promoter region and upstream of the ribosome binding site of the polynucleotide sequence encoding the polypeptide, wherein the modified mRNA processing/stabilizing sequence promotes higher expression of the polynucleotide sequence compared to an unmodified mRNA processing/stabilizing sequence; and (b) isolating the polypeptide having biological activity from the cultivation medium. The present invention also relates to such modified mRNA processing/stabilizing sequences, nucleic acid constructs, and bacterial host cells and to methods of obtaining such bacterial host cells.

28 Claims, 29 Drawing Sheets

MODIFIED MESSENGER RNA STABILIZING SEQUENCES FOR EXPRESSING GENES IN BACTERIAL CELLS

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to methods of producing polypeptides having biological activity in bacterial host cells. The present invention also relates to isolated modified mRNA processing/stabilizing sequences and to nucleic acid constructs, vectors, and host cells comprising the modified mRNA processing/stabilizing sequences operably linked to promoter regions for expressing polynucleotide sequences encoding polypeptides having biological activity.

2. Description of the Related Art

The recombinant production of a native or heterologous polypeptide having biological activity in a bacterial host cell, particularly a *Bacillus* cell, may provide for a more desirable vehicle for producing the substance in commercially relevant quantities.

Recombinant production of a native or heterologous polypeptide having biological activity is accomplished by constructing an expression cassette in which the DNA coding for the polypeptide is placed under the expression control of a promoter, excised from a regulated gene, suitable for the host cell. The expression cassette is introduced into the host cell, usually by plasmid-mediated transformation. Production of the polypeptide is then achieved by culturing the transformed host cell under inducing conditions necessary for the proper functioning of the promoter contained on the expression cassette.

Translation initiation frequency, codon usage, and RNA secondary structure are factors that affect mRNA stability in bacteria (Regnier and Arraiano, 2000, *Bioessays* 22: 235-244; Steege, 2000, *RNA* 6: 1079-1090). In *Bacillus subtilis*, mRNA stability is influenced by ribosome stalling at the 5'-untranslated region. For example, the stability of the *Bacillus subtilis* alkaline protease gene (aprE) was found to have a high half-life in *Bacillus subtilis* of approximately 25 minutes as a result of the ribosome binding site (Shine-Dalgarno sequence) present in the gene leader region (Hambraeus et al., 2002, *Microbiology* 148: 1795-1803). The complementarity of the Shine-Dalgarno sequences at the 3'-OH end of the 16S ribosomal RNA determines the affinity between the ribosomal subunits and the mRNA. The fixation of a ribosomal subunit to the 5'-UTR has been reported to be an mRNA stability inducer in *Bacillus subtilis* (Sharp and Bechhofer, 2003, *J. Bacteriology* 173: 4952-4958). The presence of Shine-Dalgarno-like sequences, referred to as stabilizer sequences, in the 5'-UTR has been proposed to be one of the causes of high mRNA stability observed for the cryIIIA gene (Agaisse and Lereclus, 1996, *Mol. Microbiol.* 20: 633-643). U.S. Pat. Nos. 6,255,076 and 5,955,310 describe the use of the cryIIIA mRNA stabilizer sequence for improved expression of enzymes in *Bacillus* cells. Daguer et al., 2005, *Letters in Applied Microbiology* 41: 221-226, describe increasing the stability of sacB transcripts improves levansucrase production in *Bacillus subtilis*.

It would be an advantage in the art to provide new methods for transcript stabilization to improve the level of a polypeptide expressed by a bacterial host strain.

The present invention relates to improved methods of producing a polypeptide having biological activity in a bacterial host cell.

SUMMARY OF THE INVENTION

The present invention relates to methods of producing a polypeptide having biological activity in a bacterial host cell, comprising: (a) cultivating a bacterial host cell in a medium conducive for production of the polypeptide having biological activity, wherein the bacterial host cell comprises a nucleic acid construct comprising a promoter region operably linked to a polynucleotide sequence encoding the polypeptide having biological activity and a modified mRNA processing/stabilizing sequence located downstream of the promoter region and upstream of the ribosome binding site (RBS) of the polynucleotide sequence encoding the polypeptide having biological activity, wherein the modified mRNA processing/stabilizing sequence promotes higher expression of the polynucleotide sequence compared to an unmodified mRNA processing/stabilizing sequence; and (b) isolating the polypeptide having biological activity from the cultivation medium.

The present invention also relates to bacterial host cells comprising a nucleic acid construct that comprises a promoter region operably linked to a polynucleotide sequence encoding a polypeptide having biological activity and a modified mRNA processing/stabilizing sequence located downstream of the promoter region and upstream of the ribosome binding site of the polynucleotide sequence encoding the polypeptide having biological activity, wherein the modified mRNA processing/stabilizing sequence promotes higher expression of the polynucleotide sequence compared to an unmodified mRNA processing/stabilizing sequence.

The present invention also relates to methods of obtaining a bacterial host cell, comprising introducing into a bacterial cell a nucleic acid construct comprising a promoter region operably linked to a polynucleotide sequence encoding a polypeptide having biological activity and a modified mRNA processing/stabilizing sequence located downstream of the promoter region and upstream of the ribosome binding site of the polynucleotide sequence encoding the polypeptide having biological activity, wherein the modified mRNA processing/stabilizing sequence promotes higher expression of the polynucleotide sequence compared to an unmodified mRNA processing/stabilizing sequence.

The present invention also relates to modified mRNA processing/stabilizing sequences.

The present invention also relates to nucleic acid constructs comprising a promoter region operably linked to a polynucleotide sequence encoding a polypeptide having biological activity and a modified mRNA processing/stabilizing sequence located downstream of the promoter region and upstream of the ribosome binding site of the polynucleotide sequence encoding the polypeptide having biological activity, wherein the modified mRNA processing/stabilizing sequence promotes higher expression of the polynucleotide sequence compared to an unmodified mRNA processing/stabilizing sequence.

The present invention further relates to methods of producing a selectable marker-free mutant of a bacterial host cell, comprising deleting a selectable marker gene of the bacterial host cell, wherein the bacterial cell comprises a nucleic acid construct comprising a promoter region operably linked to a polynucleotide sequence encoding a polypeptide having biological activity and a modified mRNA processing/stabilizing sequence located downstream of the promoter region and upstream of the ribosome binding site of the polynucleotide sequence encoding the polypeptide having biological activity, wherein the modified mRNA processing/stabilizing sequence promotes higher expression of the polynucleotide sequence compared to an unmodified mRNA processing/stabilizing sequence.

DEFINITIONS

Figure 1:
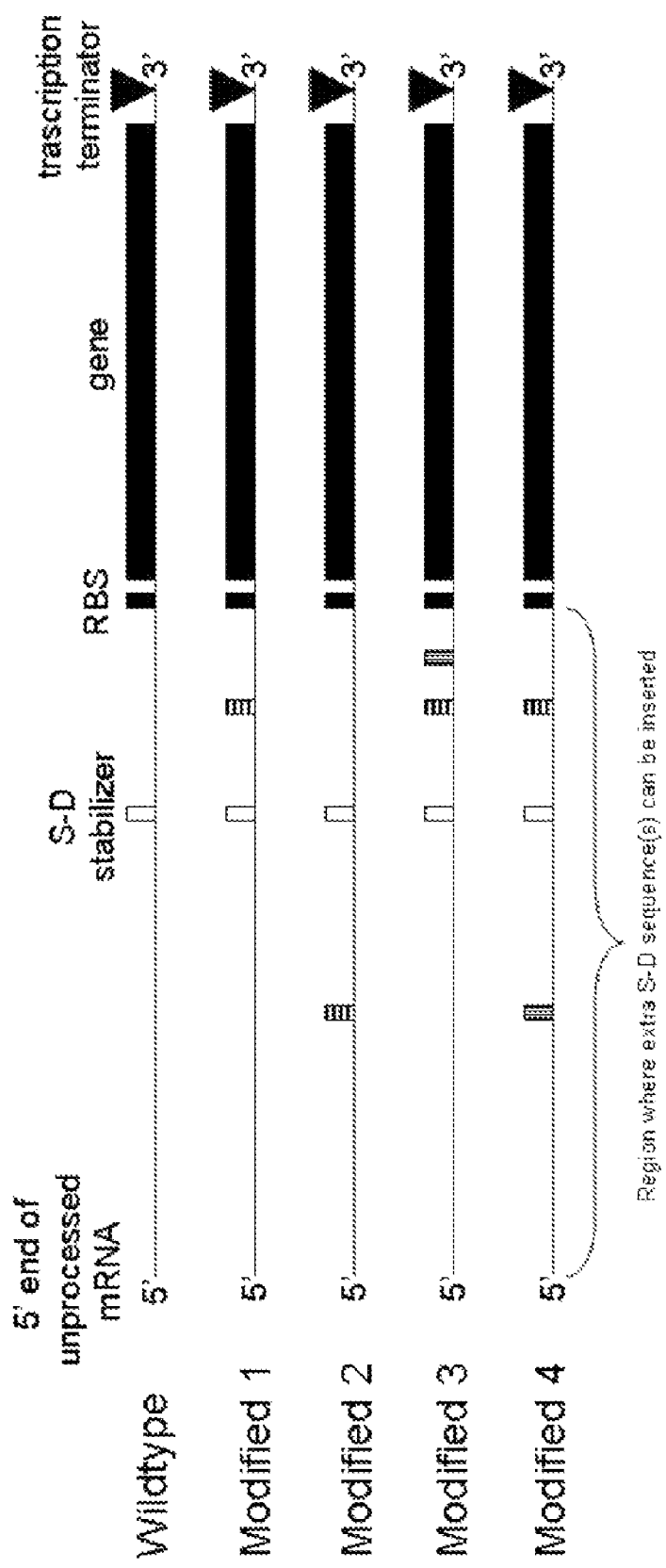
FIG. 1 shows a schematic diagram of unprocessed mRNAs and the position of various modified mRNA processing/stabilizing Shine-Dalgarno (S-D) sequences in relation to a gene being expressed, the endogenous ribosome binding site (RBS) of the gene, and the transcription terminator sequence (stem-loop). "Wild-type" depicts the unmodified mRNA processing/stabilizing sequence. "Modified 1" is the modified version of the mRNA processing/stabilizing sequence that is described in Example 5. "Modified 2, 3, and 4" are various modified mRNA processing/stabilizing sequences. "Modified 2" contains one extra Shine-Dalgarno sequence, similar to "Modified 1" except the extra Shine-Dalgarno sequence is in a different location, "Modified 3 and 4" contain yet additional Shine-Dalgarno sequences located at different locations. All of the additional Shine-Dalgarno sequences are located between the gene's endogenous RBS and the 5' end of the unprocessed mRNA.

Messenger RNA (mRNA) processing/stabilizing sequence: The term "mRNA processing/stabilizing sequence" is defined herein as a sequence located downstream of a promoter region and upstream of the translation initiation site (i.e., ribosome binding site; RBS) of a polynucleotide encoding a polypeptide having biological activity to which the promoter region is operably linked such that all mRNAs synthesized from the promoter region may be processed to generate mRNA transcripts with a stabilizer sequence at the 5' end of the transcripts. The presence of such a stabilizer sequence at the 5' end of the mRNA transcripts increases their half-life (Agaisse and Lereclus, 1994, supra, Hue et al., 1995, *Journal of Bacteriology* 177: 3465-3471). The mRNA processing/stabilizing sequence is complementary to the 3' extremity of bacterial 16S ribosomal RNA. In a preferred aspect, the mRNA processing/stabilizing sequence generates essentially single-size transcripts with a stabilizing sequence at the 5' end of the transcripts. The mRNA processing/stabilizing sequence is preferably one that is complementary to the 3' extremity of a bacterial 16S ribosomal RNA. See, for example, U.S. Pat. Nos. 6,255,076 and 5,955,310.

Shine-Dalgarno sequence: The term "Shine-Dalgarno sequence" is defined herein as a nucleotide sequence in a messenger RNA molecule to which a ribosome will bind. Such a sequence is complementary to the 3' end of a bacterial 16S ribosomal RNA.

In a preferred aspect, the Shine-Dalgarno sequence comprises the sequence GGAG. In another preferred aspect, the Shine-Dalgarno sequence comprises the sequence GGAGG. In another preferred aspect, the Shine-Dalgarno sequence comprises the sequence AGAAAGGAGG (SEQ ID NO: 1). In another preferred aspect, the Shine-Dalgarno sequence comprises the sequence AGAAAGGAGGTGATCCAGC-CGCACC (SEQ ID NO: 2). In another preferred aspect, the Shine-Dalgarno sequence comprises the sequence TAGAAAGGAGGTGATCCAGCCGCACCTT (SEQ ID NO: 3).

Unmodified mRNA processing/stabilizing sequence: The term "unmodified mRNA processing/stabilizing sequence" is defined herein as a wild-type polynucleotide comprising a mRNA processing/stabilizing sequence(s).

Modified mRNA processing/stabilizing sequence: The term "modified mRNA processing/stabilizing sequence" is defined herein as a mRNA stabilizing sequence that has been recombinantly modified to comprise at least one additional copy of a Shine-Dalgarno sequence, wherein the modified mRNA processing/stabilizing sequence promotes higher expression of a polynucleotide sequence compared to an unmodified mRNA processing/stabilizing sequence.

Promoter: The term "promoter" is defined herein as a DNA sequence that binds RNA polymerase and directs the polymerase to the correct downstream transcriptional start site of a polynucleotide encoding a polypeptide having biological activity to initiate transcription. RNA polymerase effectively catalyzes the assembly of messenger RNA complementary to the appropriate DNA strand of the coding region. The term "promoter" will also be understood to include the 5' non-coding region (between promoter and translation start) for translation after transcription into mRNA, cis-acting transcription control elements such as enhancers, and/or other nucleotide sequences capable of interacting with transcription factors. The promoter can be a wild-type, variant, hybrid, or consensus promoter.

Promoter region: The term "promoter region" is defined herein as a nucleotide sequence comprising one or more (several) promoter sequences, e.g., tandem triple promoter.

Promoter variant: The term "promoter variant" is defined herein as a promoter having a nucleotide sequence comprising a substitution, deletion, and/or insertion of one or more (several) nucleotides of a parent promoter, wherein the mutant promoter has more or less promoter activity than the corresponding parent promoter. The term "promoter variant" will also encompass natural variants and in vitro generated variants obtained using methods well known in the art such as classical mutagenesis, site-directed mutagenesis, and DNA shuffling.

Tandem promoter: The term "tandem promoter" is defined herein as two or more promoter sequences each of which is operably linked to a coding sequence and mediates the transcription of the coding sequence into mRNA.

Hybrid promoter: The term "hybrid promoter" is defined herein as parts of two or more promoters that are fused together to generate a sequence that is a fusion of the two or more promoters, which when operably linked to a coding sequence of a polynucleotide encoding a polypeptide having biological activity mediates the transcription of the coding sequence into mRNA.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated, it is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, conjugation, and the like with a nucleic acid construct or expression vector.

DETAILED DESCRIPTION OF THE INVENTION

The present invention relates to methods of producing a polypeptide having biological activity in a bacterial host cell, comprising: (a) cultivating a bacterial host cell in a medium conducive for production of the polypeptide having biological activity, wherein the bacterial host cell comprises a nucleic acid construct comprising a promoter region operably linked to a polynucleotide sequence encoding the polypeptide having biological activity and a modified mRNA processing/stabilizing sequence located downstream of the promoter region and upstream of the ribosome binding site of the polynucleotide sequence encoding the polypeptide having biological activity, wherein the modified mRNA processing/stabilizing sequence promotes higher expression of the polynucleotide sequence compared to an unmodified mRNA processing/stabilizing sequence; and (b) isolating the polypeptide having biological activity from the cultivation medium.

An advantage of the present invention is that fewer copies of an expression cassette need to be introduced into the host chromosome in order to obtain saturating levels of mRNA, thus significantly reducing the length of time required to construct a production strain. Also, the present invention allows higher levels of gene expression in situations where current technology is insufficient to generate saturating levels of mRNA.

In a preferred aspect, the modified mRNA processing/stabilizing sequence promotes higher expression of a polynucleotide sequence compared to an unmodified mRNA processing/stabilizing sequence of at least 15%, preferably at least 25%, more preferably at least 50%, more preferably at least 75%, more preferably at least 100%, more preferably at least 150%, more preferably at least 200%, more preferably at least 250%, even more preferably at least 300%, most preferably at least 400%, and even most preferably at least 500%.

Messenger RNA (mRNA) Processing/Stabilizing Sequences

The present invention also relates to modified mRNA processing/stabilizing sequences. Any mRNA processing/stabilizing sequence(s) may be used as a parent(s) to construct a modified mRNA processing/stabilizing sequence of the present invention.

A modified mRNA processing/stabilizing sequence of the present invention comprises at least one additional Shine-Dalgarno sequence providing enhanced protection of the mRNA to which it is linked, thereby, resulting in even higher levels of gene expression in comparison to constructs that utilize the wild-type mRNA stabilizing sequence. The at least one additional Shine-Dalgarno sequence may be a duplicate of the Shine-Dalgarno sequence naturally associated or native to the mRNA processing/stabilizing sequence or may be obtained from a different mRNA processing/stabilizing sequence. FIG. 1 shows a schematic diagram of unprocessed mRNAs and the position of various modified mRNA processing/stabilizing sequences in relation to the gene being expressed, the endogenous ribosome binding site (RBS), and the transcription terminator sequence (stem-loop).

In a preferred aspect, the modified mRNA processing/stabilizing sequence comprises at least two Shine-Dalgarno sequences. In another preferred aspect, the modified mRNA processing/stabilizing sequence comprises at least three Shine-Dalgarno sequences. In another preferred aspect, the modified mRNA processing/stabilizing sequence comprises at least four Shine-Dalgarno sequences. In another preferred aspect, the modified mRNA processing/stabilizing sequence comprises at least five Shine-Dalgarno sequences.

In another preferred aspect, a Shine-Dalgarno sequence comprising the modified mRNA processing/stabilizing sequence is at least 4 bp. In another preferred aspect, a Shine-Dalgarno sequence comprising the modified mRNA processing/stabilizing sequence is at least 5 bp. In another preferred aspect, a Shine-Dalgarno sequence comprising the modified mRNA processing/stabilizing sequence is at least 10 bp. In another preferred aspect, a Shine-Dalgarno sequence comprising the modified mRNA processing/stabilizing sequence is at least 15 bp. In another preferred aspect, a Shine-Dalgarno sequence comprising the modified mRNA processing/stabilizing sequence is at least 20 bp. In another preferred aspect, a Shine-Dalgarno sequence comprising the modified mRNA processing/stabilizing sequence is at least 25 bp. In another preferred aspect, a Shine-Dalgarno sequence comprising the modified mRNA processing/stabilizing sequence is at least 30 bp.

The modified mRNA processing/stabilizing sequence can be constructed (1) by placing one or more (several) Shine-Delgarno sequences, in addition to a Shine-Delgarno/mRNA stabilization sequence that is already present, between the transcription start site of the gene of interest and the gene's RBS, or (2) by placing two or more (several) Shine-Delgarno sequences between the transcription start site of the gene of interest and the gene's RBS, where the gene does not already contain a Shine-Delgarno/mRNA stabilization sequence in addition to the existing RBS. The modified mRNA processing/stabilizing sequence can be constructed from Shine-Delgarno sequences distinct from the gene. Each of the Shine-Delgarno sequences of the modified mRNA processing/stabilizing sequence may be the same sequence or a combination of one or more (several) different sequences. For example, as described herein, an extra Shine-Delgarno sequence is placed midway between the already existing Shine-Delgarno/mRNA stabilizing sequence and the RBS. Because the RBS is itself usually also a Shine-Delgarno sequence, there are, therefore, a minimum of three Shine-Delgarno sequences present on the unprocessed mRNA. The first two (starting from the 5' end) confer mRNA stability and the third (the RBS) directs translation of the mRNA.

In a preferred aspect, the parent mRNA processing/stabilizing sequence is the *Bacillus thuringiensis* cryIIIA mRNA processing/stabilizing sequence disclosed in WO 94/25612 and Agaisse and Lereclus, 1994, Molecular Microbiology 13: 97-107, or portions thereof that retain the mRNA processing/stabilizing function.

In another preferred aspect, the parent mRNA processing/stabilizing sequence is the *Bacillus subtilis* SP82 mRNA processing/stabilizing sequence disclosed in Hue et al., 1995, supra, or portions thereof that retain the mRNA processing/stabilizing function.

In a more preferred aspect, the cryIIIA mRNA processing/stabilizing sequence is SEQ ID NO: 4, or a portion thereof that retains the mRNA stabilizing function of SEQ ID NO: 4.

In another more preferred aspect, the SP82 mRNA processing/stabilizing sequence is SEQ ID NO: 5, or a portion thereof that retains the mRNA stabilizing function of SEQ ID NO: 5.

In a preferred aspect, the modified mRNA processing/stabilizing sequence is SEQ ID NO: 6, or a portion thereof that retains the mRNA stabilizing function of SEQ ID NO: 6.

The modified mRNA processing/stabilizing sequence is preferably located downstream of the promoter region and upstream of the gene's ribosome binding site. However, the modified mRNA processing/stabilizing sequence can be located downstream of any promoter comprising the promoter region and upstream of the ribosome binding site of the polynucleotide sequence encoding the polypeptide having biological activity. Furthermore, the modified mRNA processing/stabilizing sequence can be located downstream of each of the promoters comprising the promoter region and upstream of the ribosome binding site of the polynucleotide sequence encoding the polypeptide having biological activity. The parent of the modified mRNA processing/stabilizing sequence or sequences may be foreign to one or more (several) of the promoters of the promoter region.

Polynucleotides Encoding Polypeptides Having Biological Activity

A polypeptide having biological activity encoded by a polynucleotide introduced into a bacterial host cell may be any polypeptide of interest. The term "polypeptide" is not meant herein to refer to a specific length of the encoded product and, therefore, encompasses peptides, oligopeptides, and proteins. The polypeptide may be native or heterologous (foreign) to the bacterial host cell. The term "heterologous polypeptide" is defined herein as a polypeptide that is not native to the host cell; a native polypeptide in which structural modifications have been made to alter the native polypeptide, e.g., the protein sequence of a native polypeptide; or a native polypeptide whose expression is quantitatively altered as a result of a manipulation of the DNA encoding the polypeptide by recombinant DNA techniques, e.g., a stronger promoter. The polypeptide may be an engineered variant of any polypeptide.

In a preferred aspect, the polypeptide is an antibody, antigen, antimicrobial peptide, enzyme, growth factor, hormone, immunodilator, neurotransmitter, receptor, reporter protein, structural protein, and transcription factor.

In a more preferred aspect, the polypeptide is an oxidoreductase, transferase, hydrolase, lyase, isomerase, or ligase. In a most preferred aspect, the polypeptide is an acetylxylan esterase, alpha-glucosidase, aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, ferulic acid esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase.

In another preferred aspect, the polypeptide is an albumin, collagen, tropoelastin, elastin, or gelatin.

In another preferred aspect, the polypeptide is a hybrid polypeptide, which comprises a combination of partial or complete polypeptide sequences obtained from at least two different polypeptides wherein one or more (several) may be heterologous to the bacterial host cell.

In another preferred aspect, the polypeptide is a fused polypeptide in which another polypeptide is fused at the N-terminus or the C-terminus of the polypeptide or fragment thereof. A fused polypeptide is produced by fusing a nucleotide sequence (or a portion thereof) encoding one polypeptide to a nucleotide sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator.

A polynucleotide encoding a polypeptide of interest may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The techniques used to isolate or clone a polynucleotide encoding a polypeptide of interest are known in the art and include isolation from genomic DNA, preparation from cDNA, or a combination thereof. The cloning of the polynucleotide of interest from such genomic DNA can be effected, e.g., by using the well known polymerase chain reaction (PCR). See, for example, Innis at al., 1990, *PCR Protocols: A Guide to Methods and Application*. Academic Press, New York. The cloning procedures may involve excision and isolation of a desired nucleic acid fragment comprising the polynucleotide encoding the polypeptide, insertion of the fragment into a vector molecule, and incorporation of the recombinant vector into a bacterial host cell where multiple copies or clones of the polynucleotide will be replicated. The DNA may be of genomic, cDNA, RNA, semisynthetic, synthetic origin, or any combinations thereof.

A polynucleotide encoding a polypeptide of interest may be manipulated in a variety of ways to provide for expression of the polynucleotide in a suitable bacterial host cell. The construction of nucleic acid constructs and recombinant expression vectors for the polynucleotide encoding a polypeptide of interest can be carried out as described herein for the expression of a polypeptide having biological activity.

Nucleic Acid Constructs

The present invention also relates to nucleic acid constructs comprising a promoter region operably linked to a polynucleotide sequence encoding a polypeptide having biological activity and a modified mRNA processing/stabilizing sequence located downstream of the promoter region and upstream of the ribosome binding site of the polynucleotide sequence encoding the polypeptide having biological activity.

The construction of a nucleic acid construct comprising a promoter region operably linked to a polynucleotide sequence encoding a polypeptide having biological activity and a modified mRNA processing/stabilizing sequence of the present invention, which is located downstream of the promoter region and upstream of the ribosome binding site of the polynucleotide sequence, may be accomplished by modifying the polynucleotide sequence using methods well known in the art to operably link the promoter region and the modified mRNA processing/stabilizing sequence, as well as other control sequences, to the polynucleotide, inserting the construct into a vector, and introducing the vector into the bacterial cell's chromosome by homologous recombination or into the bacterial cell as an extrachromosomal autonomously replicating element, e.g., plasmid.

Each control sequence may be native or foreign to the polynucleotide sequence encoding the polypeptide having biological activity and may be foreign to each other. Such control sequences include, but are not limited to, a leader, a promoter region, a signal sequence, and a transcription terminator. At a minimum, the control sequences include a promoter region, and transcriptional and translational stop signals. The control sequences may be provided with linkers for the purpose of introducing specific restriction sites facilitating ligation of the control sequences with the coding region of the polynucleotide sequence encoding a polypeptide having biological activity.

Promoter Region. The promoter region may comprise a single promoter or a combination of promoters. Where the promoter region comprises a combination of promoters, the promoters are preferably in tandem. A promoter of the promoter region can be any promoter that can initiate transcription of a polynucleotide encoding a polypeptide having biological activity in a bacterial host cell of interest. The promoter may be native, foreign, or a combination thereof, to the nucleotide sequence encoding a polypeptide having biological activity. Such a promoter can be obtained from genes directing synthesis of extracellular or intracellular polypeptides having biological activity either homologous or heterologous to the bacterial host cell.

In a preferred aspect, the promoter region comprises a promoter obtained from a bacterial source. In a more preferred aspect, the promoter region comprises a promoter obtained from a Gram positive bacterium. In another more preferred aspect, the promoter region comprises a promoter obtained from a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

In a most preferred aspect, the promoter region comprises a promoter obtained from a *Bacillus* strain, e.g., *Bacillus agaradherens, Bacillus alkalophilus, Bacillus amyloiquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis*; or from a *Streptomyces* strain, e.g., *Streptomyces lividans* or *Streptomyces murinus*.

Examples of suitable promoters for directing transcription of a polynucleotide encoding a polypeptide having biological activity in the methods of the present invention are the promoters obtained from the *E. coli* lac operon, *Streptomyces coelicolor* agarase gene (dagA), *Bacillus lentus* or *Bacillus clausii* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. *tenebrionis* CryIIIA gene (cryIIIA) or portions thereof, prokaryotic beta-lactamase gene (VIIIa-Kamaroff et al. 1978, *Proceedings of the National Academy of Sciences USA* 75:3727-3731), and *Bacillus megaterium* xylA gene (Rygus and Hillen, 1992, *J. Bacteriol.* 174: 3049-3055; Kim et al., 1996. *Gene* 181: 71-76), as well as the tac promoter (DeBoer et al., 1983, *Proceedings of the National Academy of Sciences USA* 80: 21-25), the orfβ promoter of plasmid pUB110 (Tortosa et al., 2000, *Mol. Microbiol.* 35: 1110-1119), and the spac promoter (Henner, 1990, *Methods Enzymol.* 185: 223-228). Other examples are the promoter of the spo1 bacterial phage promoter and the tac promoter (DeBoer et al., 1983, *Proceedings of the National Academy of Sciences USA* 80:21-25). Further promoters are described in "Useful proteins from recombinant bacteria" in *Scientific American*, 1980, 242:74-94; and in Sambrook, Fritsch, and Maniatus, 1989, *Molecular Cloning, A Laboratory Manual*, 2d edition, Cold Spring Harbor, N.Y.

In another preferred aspect, the promoter region comprises a promoter that is a "consensus" promoter having the sequence TTGACA for the "−35" region and TATAAT for the "−10" region. The consensus promoter may be obtained from any promoter that can function in a bacterial host cell, e.g., *Bacillus*. The construction of a "consensus" promoter may be accomplished by site-directed mutagenesis using methods well known in the art to create a promoter that conforms more perfectly to the established consensus sequences for the "−10" and "−35" regions of the vegetative "sigma A-type" promoters for *Bacillus subtilis* (Voskuil et al., 1995, *Molecular Microbiology* 17: 271-279).

In another preferred aspect, the promoter region comprises a "consensus" promoter obtained from a promoter obtained from the *E. coli* lac operon, *Streptomyces coelicolor* agarase gene (dagA), *Bacillus clausii* or *Bacillus lentus* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. *tenebrionis* CryIIIA gene (cryIIIA) or portions thereof, or prokaryotic beta-lactamase gene spo1 bacterial phage promoter.

In a more preferred aspect, the promoter region comprises a "consensus" promoter obtained from *Bacillus amyloliquefaciens* alpha-amylase gene (amyQ).

In another preferred aspect, the promoter region comprises a promoter that is a hybrid promoter.

In another preferred aspect, the promoter region comprises a promoter that is a variant promoter. See, for example, WO 05/098016, U.S. Pat. No. 5,698,415, and U.S. Pat. No. 6,100,063. In a preferred aspect, the variant promoter is $P_{amyL4199}$, wherein P=promoter In another preferred aspect, the promoter region comprises a promoter that is a tandem promoter. See, for example, WO 99/043835 and WO 05/098016. In a preferred aspect, the tandem promoter is $P_{consensus\ amyQ}$-$P_{cryIIIA}$-cryIIIA mRNA processing/stabilizing sequence. In another preferred aspect, the tandem promoter is $P_{amyL4199}$-$P_{consensus\ amyQ}$-$P_{cryIIIA}$-cryIIIA mRNA processing/stabilizing sequence.

In the methods of the present invention, a hybrid or tandem promoter will be understood to be foreign to a polynucleotide sequence encoding a polypeptide having biological activity even if the wild-type promoter is native to the polynucleotide sequence. For example, in a tandem promoter consisting of at least two promoters, one of the promoters may be a the wild-type promoter of the polynucleotide encoding a biological substance.

Terminator. The control sequence may also be a suitable transcription terminator sequence, a sequence recognized by a bacterial cell to terminate transcription. The terminator sequence is operably linked to the 3' terminus of the nucleotide sequence encoding a polypeptide having biological activity. Any terminator that is functional in the bacterial host cell of choice may be used in the present invention.

Leader. The control sequence may also be a suitable leader sequence, a nontranslated region of a mRNA that is important for translation by the bacterial cell. The leader sequence is operably linked to the 5' terminus of the nucleotide sequence directing synthesis of the polypeptide having biological activity. Any leader sequence that is functional in the bacterial host cell of choice may be used in the present invention.

Signal peptide coding region. The control sequence may also be a signal peptide coding region, which codes for an amino acid sequence linked to the amino terminus of a polypeptide that can direct the expressed polypeptide into the cell's secretory pathway. The signal peptide coding region may be native to the polypeptide or may be obtained from foreign sources. The 5' end of the coding sequence of the polynucleotide encoding the polypeptide may inherently contain a signal peptide coding region naturally linked in translation reading frame with the segment of the coding region that encodes the secreted polypeptide. Alternatively, the 5' end of the coding sequence may contain a signal peptide coding region that is foreign to that portion of the coding sequence that encodes the secreted polypeptide. The foreign signal peptide coding region may be required where the coding sequence does not naturally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained, for example, from an amylase or a protease gene from a *Bacillus* species. However, any signal peptide coding region capable of directing the expressed polypeptide into the secretory pathway of a bacterial host cell of choice may be used in the present invention.

An effective signal peptide coding region for bacterial cells, e.g., *Bacillus* cells, is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, *Microbiological Reviews* 57:109-137.

Selectable markers. A nucleic acid construct may further contain one or more (several) selectable markers that permit easy selection of transformed cells. A selectable marker is a gene the product of which provides for biocide resistance, resistance to heavy metals, prototrophy to auxotrophs, and the like. Examples of bacterial selectable markers are the dal genes from *Bacillus subtilis* or *Bacillus licheniformis*, or markers that confer antibiotic resistance, such as ampicillin, kanamycin, erythromycin, chloramphenicol or tetracycline resistance. Furthermore, selection may be accomplished by co-transformation, e.g., as described in WO 91/09129, where the selectable marker is on a separate vector.

The nucleic acid construct can then be introduced into a bacterial host cell using methods known in the art or those methods described herein for expressing the polypeptide having biological activity. The bacterial host cell may contain one or more (several) copies of the same nucleic acid construct or one or more (several) copies of at least two different nucleic acid constructs, wherein each of the constructs are constructed as described supra.

Expression Vectors

In the methods of the present invention, a recombinant expression vector can be constructed comprising a promoter region operably linked to a polynucleotide sequence encoding a polypeptide having biological activity and a modified mRNA processing/stabilizing sequence of the present invention, which is located downstream of the promoter region and upstream of the ribosome binding site of the polynucleotide sequence encoding the polypeptide having biological activity. The various nucleic acid and control sequences described above may be joined together to produce a recombinant expression vector that may include one or more (several) convenient restriction sites to allow for insertion or substitution of the polynucleotide at such sites. Alternatively, the polynucleotide sequence encoding the polypeptide having biological activity may be expressed by inserting the polynucleotide sequence or a nucleic acid construct comprising the polynucleotide sequence into an appropriate vector for expression. In creating the expression vector, the polynucleotide sequence encoding the polypeptide having biological activity is located in the vector so that the coding sequence is operably linked to a promoter region and a modified mRNA processing/stabilizing sequence, and any other appropriate control sequences for expression, and possibly translocation.

The recombinant expression vector may be any vector that can be conveniently subjected to recombinant DNA procedures and can bring about expression of the polypeptide having biological activity on introduction into a bacterial host cell. The choice of the vector will typically depend on the compatibility of the vector with the bacterial host cell into which the vector is to be introduced. The vectors may be linear or closed circular plasmids. The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the bacterial host cell, is integrated into the chromosome and replicated together with the chromosome into which it has been integrated. The vector system may be a single vector or plasmid or two or more vectors or plasmids, or a transposon.

"Introduction" means introducing a vector into a bacterial host cell so that the vector is maintained as a chromosomal integrant or as a self-replicating extrachromosomal vector. Integration is generally considered to be an advantage as the one or more (several) coding sequences or genes are more likely to be stably maintained in the cell. Integration of the vector into the chromosome occurs by homologous recombination, non-homologous recombination, or transposition.

The introduction of an expression vector into a bacterial host cell may, for instance, be effected by transformation, transfection, transduction, conjugation, and the like For integration, the vector may rely on any component of the vector for stable integration of the vector into the genome by homologous recombination. The vector may contain additional polynucleotide sequences for directing integration by homologous recombination into the genome of the bacterial host cell. The additional polynucleotide sequences enable the vector to be integrated into the bacterial host cell genome at a precise location in the chromosome. To increase the likelihood of integration at a precise location, the integrational components should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational components may be any polynucleotide sequence that is homologous with the target sequence in the genome of the bacterial host cell. Furthermore, the integrational components may be non-encoding or encoding sequences.

For autonomous replication, the vector may further comprise an origin of replication enabling the vector to replicate autonomously in the *Bacillus* cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. The origin of replication may be one having a mutation to make its function temperature-sensitive in the bacterial host cell (see, e.g., Ehrlich, 1978, *Proceedings of the National Academy of Sciences USA* 75: 1433).

The procedures used to ligate the components described above to construct the recombinant expression vectors are well known to one skilled in the art (see, e.g., Sambrook et al., 1989, supra).

Bacterial Host Cells

The present invention also relates to bacterial host cells comprising a promoter region operably linked to a polynucleotide sequence encoding a polypeptide having biological activity and a modified mRNA processing/stabilizing sequence of the present invention, which is located downstream of the promoter region and upstream of the ribosome binding site of the polynucleotide sequence encoding the polypeptide having biological activity, wherein the modified mRNA processing/stabilizing sequence promotes higher expression of the polynucleotide sequence compared to an unmodified mRNA processing/stabilizing sequence. In a preferred aspect, the bacterial cell is free of a foreign (heterologous) selectable marker gene.

The present invention also relates to methods of obtaining a bacterial host cell, comprising introducing into a bacterial cell a nucleic acid construct comprising a promoter region operably linked to a polynucleotide sequence encoding a polypeptide having biological activity and a modified mRNA processing/stabilizing sequence of the present invention, which is located downstream of the promoter region and upstream of the ribosome binding site of the polynucleotide sequence encoding the polypeptide having biological activity, wherein the modified mRNA processing/stabilizing sequence promotes higher expression of the polynucleotide sequence compared to an unmodified mRNA processing/stabilizing sequence.

The bacterial host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

In the methods of the present invention, the bacterial host cell may be any *Bacillus* cell. *Bacillus* cells useful in the practice of the present invention include, but are not limited to, *Bacillus alkalophilus, Bacillus amyloliquefaciens, Bacillus atrophaeus, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus mojavensis, Bacillus pumilus, Bacillus stearothermophilus, Bacillus subtilis, Bacillus thuringiensis*, and *Bacillus vallismortis* cells.

In a preferred aspect, the bacterial host cell is a *Bacillus amyloliquefaciens, Bacillus lentus, Bacillus licheniformis, Bacillus stearothermophilus*, or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

In the methods of the present invention, the bacterial host cell may be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus*.

In another preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

In the methods of the present invention, the bacterial host cell may be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans*.

In another preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

In a further aspect of the present invention, the bacterial host cells may additionally contain modifications, e.g., deletions or disruptions, of other genes that may be detrimental to the production, recovery, and/or application of a polypeptide having biological activity. In a preferred aspect, a bacterial host cell is a protease-deficient cell. In a more preferred aspect, the bacterial host cell, e.g., *Bacillus* cell, comprises a disruption or deletion of aprE and nprE. In another preferred aspect, the bacterial host cell does not produce spores. In another more preferred aspect, the bacterial host cell, e.g., *Bacillus* cell, comprises a disruption or deletion of spoIIAC. In another preferred aspect, the bacterial host cell, e.g., *Bacillus* cell, comprises a disruption or deletion of one of the genes involved in the biosynthesis of surfactin, e.g., srfA, srfB, srfC, and srfD. See, for example, U.S. Pat. No. 5,958,728. Other genes, e.g., the amyE gene, which are detrimental to the production, recovery, and/or application of a polypeptide having biological activity may also be disrupted or deleted.

The introduction of DNA into a *Bacillus* cell may, for instance, be effected by protoplast transformation (see, e.g., Chang and Cohen. 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al, 2004, *Folia Microbiol. (Praha)* 49: 399-405), by conjugation (see, e.g., Mazodier et al., 1989, *J. Bacterio* 171: 3583-3585), or by transduction (see, e.g., Burke et al., 2001, *Proc. Natl. Acad. Sci. USA* 98:6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g. Perry and Kuramitsu, 1981, *Infect. Immun,* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65; 3800-3804), or by conjugation (see, e.g., Clewell, 1981, *Microbio Rev.* 45: 409-436). However, any method known in the art for introducing DNA into a host cell can be used.

Production

In the production methods of the present invention, the bacterial host cells are cultivated in a nutrient medium suitable for production of the polypeptide having biological activity using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide having biological activity to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide having biological activity is secreted into the nutrient medium, it can be recovered directly from the medium. If the polypeptide having biological activity is not secreted, it can be recovered from cell lysates.

The polypeptide having biological activity may be detected using methods known in the art that are specific for the polypeptide having biological activity. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.). *Enzyme Handbook,* Springer-Verlag, New York, 1990).

The resulting polypeptide having biological activity may be isolated using methods well known in the art. For example, the polypeptide having biological activity may be isolated from the nutrient medium by conventional procedures including, but not limited to, centrifugation, filtration, extraction, spray-drying, evaporation, or precipitation. The isolated polypeptide having biological activity may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., *Protein Purification,* J.-C. Janson and Lars Ryden, editors, VCH Publishers, New York, 1989).

In the methods of the present invention, the bacterial host cell preferably produces at least 15%, preferably at least 25%, more preferably at least 50%, more preferably at least 75%, more preferably at least 100%, more preferably at least 150%, more preferably at least 200%, more preferably at least 250%, even more preferably at least 300%, most preferably at least 400%, and even most preferably at least 500% more of the polypeptide having biological activity relative to a bacterial host containing the promoter region operably linked to a polynucleotide sequence encoding the polypeptide having biological activity and the parent mRNA processing/stabilizing sequence located downstream of the promoter region and upstream of the ribosome binding site of the polynucleotide sequence encoding the polypeptide having biological activity when cultured under identical production conditions, Deletions/Disruptions The present invention also relates to methods of producing a selectable marker-free mutant of a bacterial host cell, comprising deleting a selectable marker gene of the bacterial host cell, wherein the bacterial cell comprises a nucleic acid construct comprising a promoter region operably linked to a polynucleotide sequence encoding a polypeptide having biological activity and a modified mRNA processing/stabilizing sequence located downstream of the promoter region and upstream of the ribosome binding site of the polynucleotide sequence encoding the polypeptide having biological activity, wherein the modified mRNA processing/stabilizing sequence promotes higher expression of the polynucleotide sequence compared to an unmodified mRNA processing/stabilizing sequence.

Gene deletion or replacement techniques may be used for the complete removal of a foreign or heterologous selectable marker gene or other undesirable gene. In such methods, the deletion of the selectable marker gene may be accomplished by homologous recombination using a plasmid that has been constructed to contiguously contain the 5' and 3' regions flanking the selectable marker gene. For example, the contiguous 5' and 3' regions may be introduced into a *Bacillus* cell on a temperature-sensitive plasmid, e.g., pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, for example, Perego, 1993, In A. L. Sonneshein, J. A. Hoch, and R. Losick, editors, *Bacillus subtilis and Other Gram-Positive Bacteria,* Chapter 42, American Society of Microbiology. Washington, D.C., 1993).

A selectable marker gene may also be removed by homologous recombination by introducing into the mutant cell a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

The procedures described above can also be used to delete or disrupt any undesirable gene. U.S. Pat. No. 5,891,701 discloses techniques for deleting several genes including spoIIAC, aprE, nprE, and amyE.

Other undesirable biological compounds may also be removed by the above described methods such as the red pigment synthesized by cypX (accession no. BG12580) and/or yvmC (accession no. BG14121).

In a preferred aspect, the *Bacillus* host cell is unmarked with any foreign or heterologous selectable markers. In another preferred aspect, the *Bacillus* host cell does not produce any red pigment synthesized by cypX and yvmC.

The present invention is further described by the following examples that should not be construed as limiting the scope of the invention.

EXAMPLES

DNA Sequencing

DNA sequencing was performed using an Applied Biosystems Model 3130× Genetic Analyzer (Applied Biosystems, Foster City, Calif., USA) using dye terminator chemistry (Giesecke et at, 1992, *Journal of Virol Methods* 38: 47-60). Sequences were assembled using phred/phrap/consed (University of Washington, Seattle, Wash., USA) with sequence specific primers.

Strains

*Bacillus* plasmids were constructed in *Bacillus subtilis* 168Δ4. *Bacillus subtilis* 168Δ4 is derived from the *Bacillus subtilis* type strain 168 (BGSC 1A1, *Bacillus* Genetic Stock Center, Columbus, Ohio, USA) and has deletions in the spoIIAC, aprE, nprE, and amyE genes. The deletion of these four genes was performed essentially as described for *Bacillus subtilis* A164Δ5, which is described in detail in U.S. Pat. No. 5,891,701.

Media

LB medium was composed per liter of 10 g of tryptone, 5 g of yeast extract, and 5 g of NaCl.

LB plates were composed of LB medium and 15 g of bacto agar per liter.

LB ampicillin medium was composed of LB medium and 100 μg of ampicillin per ml.

LB ampicillin plates were composed of LB ampicillin medium and 15 g of bacto agar per liter.

VY medium was composed per liter of 25 g of veal infusion (BD Diagnostics, Franklin Lakes, N.J., USA) and 5 g of yeast extract.

2×YT medium was composed per liter of 16 g of Tryptone, 10 g of yeast extract, and 5 g of NaCl.

2×YT ampicillin medium was composed of 2×YT medium and 100 μg of ampicillin per ml.

2×YT ampicillin plates were composed per liter of 2×YT ampicillin medium and 15 g of bacto agar.

TBAB medium was composed of Difco Tryptose Blood Agar Base (BD Diagnostics, Franklin Lakes, N.J., USA).

TBAB chloramphenicol plates were composed of TBAB medium and 5 μg of chloramphenicol per ml.

TBAB neomycin plates were composed of TBAB medium and 6 μg of neomycin per ml.

TBAB erythromycin/lincomycin plates were composed of TBAB medium and 1 μg of erythromycin and 25 μg of lincomycin per ml.

TBAB milk plates were composed of TBAB medium overlaid with a milk overlay composed of 0.6 ml of a sterile 10% solution of powdered milk dissolved in deionized water added to 6 ml of melted TBAB agar.

PS-1 medium was composed per liter of 100 g sucrose, 40 g of soybean flour, 3.96 g of disodium phosphate (anhydrous), 5 g of CaCO$_3$, and 100 μl of pluronic acid.

Example 1

Construction of a Consensus cryIIIA Promoter

A consensus version of the cryIIIA promoter was constructed in which the native −35 and −10 regions were changed to those of a consensus sigma A-dependent promoter. The consensus cryIIIA (cry3A) promoter was constructed by annealing two complementary 97 nucleotide oligos, 999555 and 999556,

```
Oligo 999555:                         (SEQ ID NO: 7)
5'-CGGGCCTTAAGGGCCCTCGAAACGTAAGATGAAACCTTAGATAAAA

GTGCTTTTTTTGTTGACATTGAAGAATTATTAATGTTATAATTAATTAA

GG-3'

Oligo 999556:                         (SEQ ID NO: 8)
5'-CCTTAATTAATTATAACATTAATAATTCTTCAATGTCAACAAAAAA

AGCACTTTTATCTAAGGTTTCATCTTACGTTTCGAGGGCCCTTAAGGCC

CG-3'
```

Two 20 μl annealing reactions were performed containing 10 μl (500 pmol) and 5 μl (250 pmol) of each oligo, respectively. Both reactions were incubated at 95° C. for 5 minutes, and then the tubes were cooled gradually to room temperature. The resulting annealed product from each reaction was an approximately 97 bp double-stranded DNA fragment including the consensus −35 and −10 promoter regions, an Sfi I restriction site at the 5' end, and a Pac I site at the 3' end.

Each annealed product was amplified by PCR using 2 μl (25 or 12.5 pmol) of the annealed product as template with primers 999557 and 999558, using an EXPAND® High Fidelity PLUS PCR System (Roche Applied Science, Indianapolis, Ind., USA), according to manufacturer's instructions.

```
Primer 999557:
5'-CGGGCCTTAAGGGCCCTCGAA-3'       (SEQ ID NO: 9)

Primer 999558:
5'-CCTTAATTAATTATAACATT-3'        (SEQ ID NO: 10)
```

The products of the two PCR reactions, which were the same, were pooled, analyzed by 2.0% agarose electrophoresis with 50 mM Tris base-50 mM boric acid-1 mM disodium EDTA (TBE) buffer, and purified using a QIAQUICK® Gel Extraction Kit (QIAGEN Inc., Valencia, Calif., USA).

The purified 97 bp PCR product was then cloned into pCR2.1 using a TOPO® TA Cloning Kit (invitrogen, Carlsbad, Calif., USA) and transformed into ONE SHOT® TOP10 Chemically Competent *E. coli* cells (Invitrogen, Carlsbad, Calif., USA) according to the manufacturers instructions. Plasmid DNA from several transformants was purified using a BIOROBOT® 9600 (QIAGEN Inc., Valencia, Calif., USA) and tested for the presence of the cloned PCR fragment by digestion with Eco RI followed by 0.8% agarose electrophoresis in TEE buffer. One plasmid with Eco RI fragments of approximately 3.94 kb and 115 bp was designated pCR2.1-consensus cryIIIA. The DNA sequence of the cloned PCR fragment was confirmed by DNA sequencing.

Figure 2:
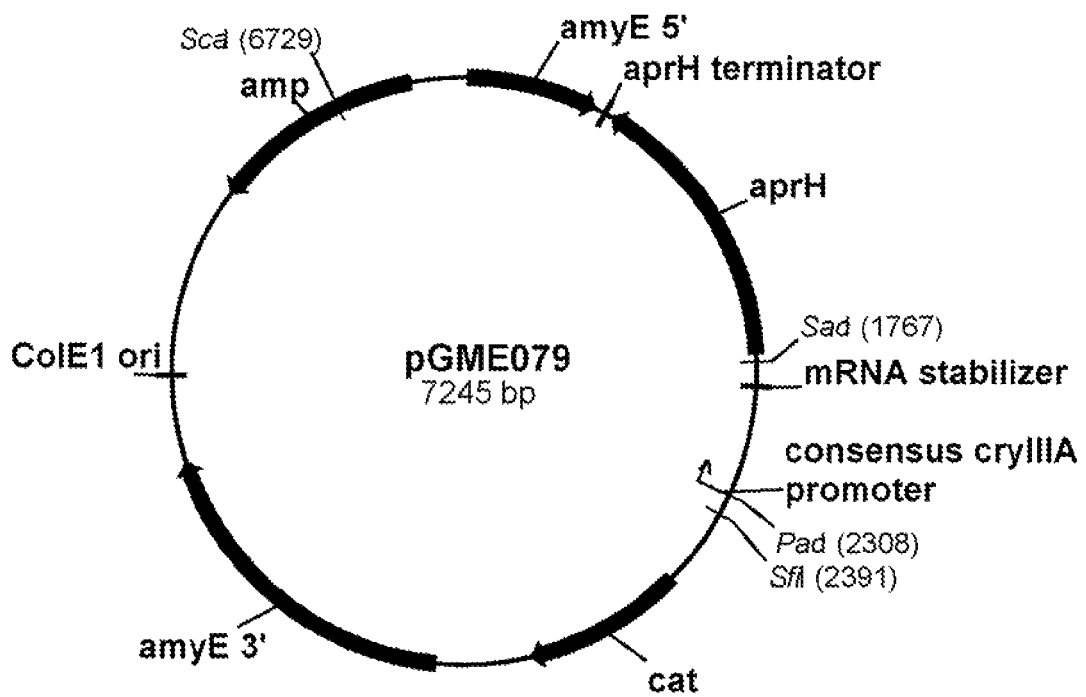
FIG. 2 shows a restriction map of pGME079.

Plasmid pCR2.1-consensus cryIIIA was digested with Sfi I and Pac I and analyzed by 2.0% agarose electrophoresis in TBE buffer, and an approximately 82 bp fragment bearing the consensus cryIIIA promoter was purified using a QIAQUICK® Gel Extraction Kit. Plasmid pNBT2 (pDG268Δ-$P_{cryIIIA}$/cryIIIAstab/SAV, U.S. Pat. No. 6,255,076) was digested with Sfi I and Pac I and analyzed by 2.0% agarose electrophoresis in TBE buffer, and an approximately 7162 bp vector fragment was purified using a QIAQUICK® Gel Extraction Kit. The pNBT2 vector fragment and consensus cryIIIA promoter fragment were ligated together with T4 DNA ligase (Roche Diagnostics Corporation, Indianapolis, Ind., USA) according to the manufacturer's instructions, and *E. coli* XL10-GOLD Ultracompetent cells (Stratagene Corporation, La Jolla, Calif., USA) were transformed with the ligation according to manufacturer's instructions. Plasmid DNA from several transformants was purified using a BIOROBOT® 9600 and tested by digestion with Eco RI and Sfi I followed by 0.8% agarose electrophoresis in TBE buffer. One plasmid with expected fragments of approximately 5799 bp and 1446 bp was designated pGME079 (FIG. 2).

Plasmid pGME079 was linearized by digestion with Sca I. *Bacillus subtilis* 168Δ4 was transformed with the linearized plasmid according to the procedure of Anagnostopoulos and Spizizen, 1961, *J. Bacteriol.* 81: 741-746, and transformants were selected for chloramphenicol resistance on TBAB chloramphenicol plates at 37° C. One transformant with the $P_{consensus\ cryIIIA}$/cryIIIA stab/aprH cassette inserted at the amyL locus was designated *Bacillus subtilis* GME201.

Example 2

Construction of a Modified cryIIIA mRNA Processing/Stabilizing Sequence

Figure 3:
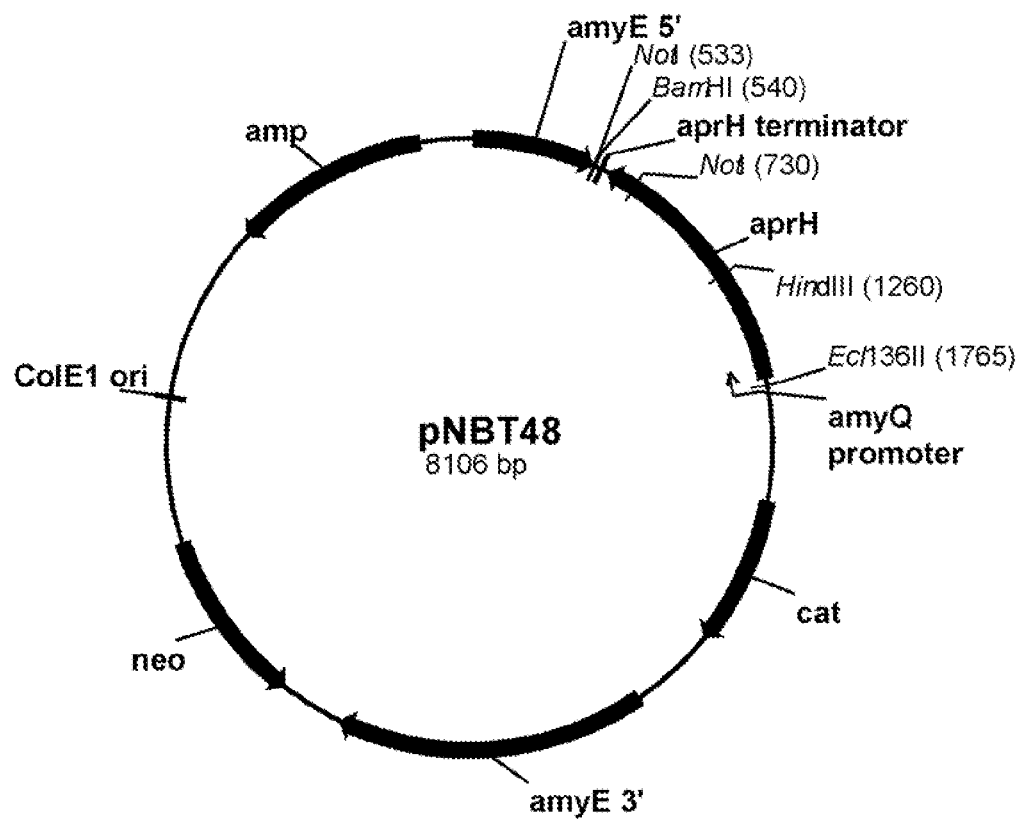
FIG. 3 shows a restriction map of pNBT48.

A modified mRNA processing/stabilizing sequence was constructed comprising a second Shine-Dalgarno sequence in addition to the native cryIIIA mRNA processing/stabilizing sequence.

An approximately 524 bp fragment, comprising the cryIIIA mRNA processing/stabilizing sequence, was amplified by PCR from plasmid pNBT3 (pDG268ΔNeo-$P_{cryIIIA}$/cryIIIAstab/SAV, U.S. Pat. No. 6,255,076) using primers 999255 and 999254 shown below. The 5' end of primer 999254 incorporates the complement of an extra Shine-Dalgarno sequence.

```
Primer 999255:                    (SEQ ID NO: 11)
5'-AGCTTAATTAAAGATAATAT-3'

Primer 999254:                    (SEQ ID NO: 12)
5'-GGCTGGATCACCTCCTTTCTATCCATTAGACGGTGCAAAT-3'
```

An approximately 596 bp fragment, comprising the N-terminal coding region of the *Bacillus clausii* alkaline protease gene (aprH), was amplified from plasmid pNBT3 using primers 999253 and 999256 shown below. The 5' end of primer 999253 incorporates an extra Shine-Dalgarno sequence and is complementary to the 5' end of primer 999254.

```
Primer 999253;                    (SEQ ID NO: 13)
5'-AGAAAGGAGGTGATCCAGCCGCACCTTATGAAAAATCATTTTAT
C-3'
```

-continued

```
Primer 999256:                    (SEQ ID NO: 14)
5'-AAGCTTGCGCCACCACGAAT-3'
```

Both PCRs were performed using 50 ng of plasmid pNBT3 template DNA, 0.4 μM each of each primer, 200 μM each of dATPP, dCTP, dGTP, and dTTP, 1×PCR Buffer II with 2.5 mM $MgCl_2$, and 2.5 units of Taq DNA polymerase in a 50 μl reaction volume. The reactions were performed in a ROBOCYCLER® 40 thermocycler (Stratagene Corporation, Lo Jolla, Calif., USA) programmed for 1 cycle at 95° C. for 2 minutes; 30 cycles each at 95° C. for 1 minute, 55° C. for 1 minute, and 72° C. for 2 minutes; and 1 cycle at 72° C. for 5 minutes.

The two PCR reactions were analyzed by 0.8% agarose electrophoresis in TBE buffer and the products were purified using a QIAQUICK® Gel Extraction Kit. The two purified PCR products were used as template DNA for a third PCR, using primers 999255 and 999256, which fused the two fragments via the complementary ends provided by the sequences of primers 999593 and 999594.

The PCR was performed using 50 ng of each purified PCR fragment, 200 μM each of dATP, dCTP, dGTP, and dTTP, 1×PCR Buffer II with 2.5 mM $MgCl_2$, and 2.5 units of Taq DNA polymerase. The reactions were performed in a ROBOCYCLER® 40 thermocycler programmed for 1 cycle at 95° C. for 2 minutes; 5 cycles each at 95° C. for 1 minute, 55° C. for 1 minute, and 72° C. for 2 minutes; 0.4 μM each of each primer was then added to the reaction and 25 cycles were performed, each at 95° C. for 1 minute, 55° C. for 1 minute, and 72° C. for 2 minutes; and finally 1 cycle at 72° C. for 5 minutes. The PCR products were visualized by 0.8% agarose electrophoresis in TBE buffer.

The resulting approximately 1080 bp PCR product was cloned into pCR2.1 using a TOPO® TA Cloning Kit and transformed into ONE SHOT® TOP10 Chemically Competent *E. coli* cells according to the manufacturer's instructions. Plasmid DNA from several transformants was purified using a BIOROBOT® 9600 and analyzed by DNA sequencing to identify those containing the desired modified cryIIIA mRNA processing/stabilizing sequence. One plasmid with the expected DNA sequence was designated pCR2.1-stabx2.

Example 3

Construction of Plasmid pNBT48

Plasmid pNBT3 (pDG268MCSΔneo-$P_{cryIIIA}$/cryIIIA stab/SAV; U.S. Pat. No. 5,955,310) was digested with Sfi I and Bam HI and analyzed by 0.8% agarose electrophoresis in TBE buffer, and an approximately 6704 bp vector fragment was purified using a QIAQUICK® Gel Extraction Kit. Plasmid pNBT8 (pDG268MCS-$P_{amyQ}$/SAV; U.S. Pat. No. 5,955,310) was digested with Sfi I and Bam HI and analyzed by 0.8% agarose electrophoresis in TBE buffer, and an approximately 1402 bp fragment comprising the *Bacillus amyloliquefaciens* amyQ promoter and *Bacillus clausii* aprH coding sequence was purified using a QIAQUICK® Gel Extraction Kit. The pNBT3 vector fragment and the $P_{amyQ}$-aprH fragment were ligated together with T4 DNA ligase as described according to the manufacturer's instructions, and *E. coli* DH5α cells (Gibco BRL, Gaithersburg, Md., USA) were transformed with the ligation according to the manufacturer's instructions, selecting for ampicillin resistance on 2×YT ampicillin plates at 37° C.

Plasmid DNA from one transformant was purified using a QIAPREP® 8 Plasmid Kit (QIAGEN Inc., Valencia, Calif., USA) and analyzed by restriction enzyme digestion with Nco I followed by 0.8% agarose electrophoresis in TBE buffer. One plasmid that yielded expected DNA fragment sizes of approximately 6802 bp and 1304 bp was identified and designated pNBT48 (FIG. 3).

Example 4

Construction of an amyQ Promoter—Modified cryIIIA mRNA Processing/Stabilizing Sequence An amyQ promoter linked to a modified cryIIIA mRNA processing/stabilizing sequence was constructed. Plasmid pCR2.1-stabx2 was digested with Pac I, and the ends were blunted using T4 DNA polymerase and dNTPs using standard methods. The blunt-ended plasmid was then digested with Hind III and analyzed by 0.8% agarose electrophoresis in TBE buffer, and an approximately 1067 bp fragment, bearing the modified cryIIIA mRNA processing/stabilizing sequence and aprH N-terminal coding region, was purified using a QIAQUICK® Gel Extraction Kit.

Figure 4:
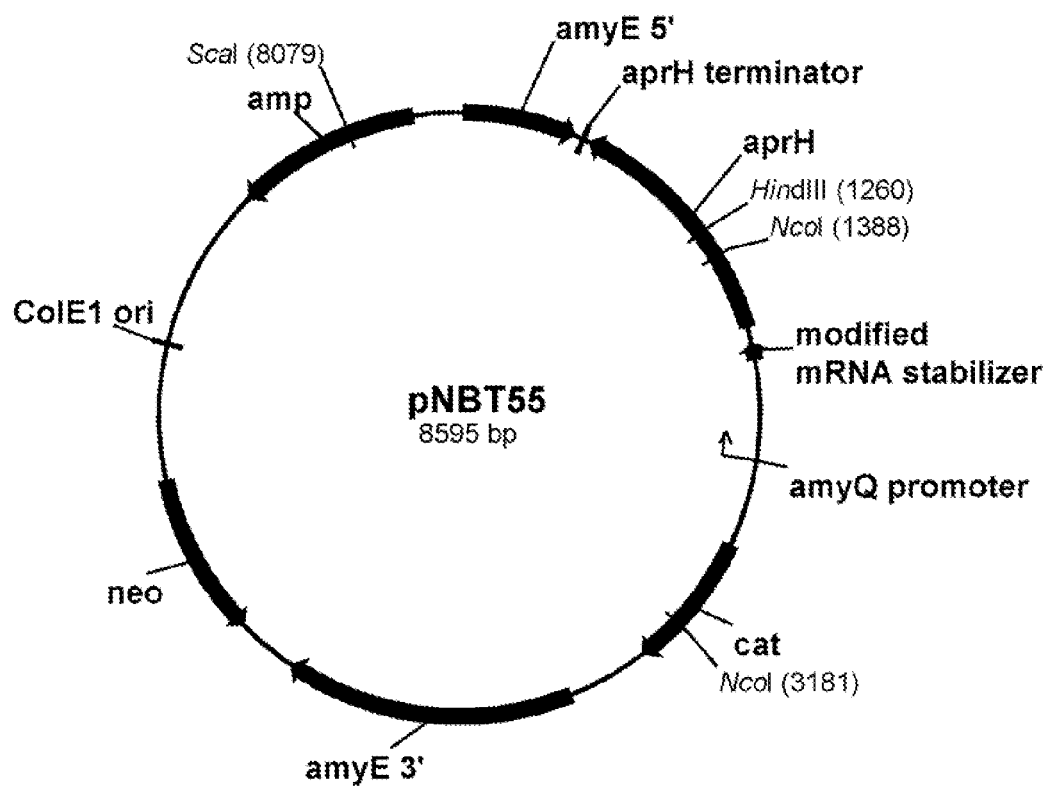
FIG. 4 shows a restriction map of pNBT55.

Plasmid pNBT48 was digested with Ecl 13611 and Hind III and analyzed by 0.8% agarose electrophoresis in TBE buffer, and an approximately 7601 bp vector fragment was purified using a QIAQUICK® Gel Extraction Kit. The pNBT48 vector fragment and the modified cryIIIA mRNA processing/stabilizing sequence fragment were ligated together with T4 DNA ligase according to the manufacturer's instructions, and $E.\ coli$ DH5α cells were transformed with the ligation according to the manufacturer's instructions, selecting for ampicillin resistance on 2×YT ampicillin plates at 37° C. Plasmid DNA from several transformants was purified using a BIOROBOT® 9600 and analyzed by restriction enzyme digestion with Nco I followed by 0.8% agarose gel electrophoresis in TBE buffer. One plasmid that gave an expected DNA fragment size of approximately 1800 bp was identified and designated pNBT55 (pDG268ΔNeo-P$_{amyQ}$/mod, cryIIIA stab/aprH) (FIG. 4).

Example 5

Construction of an amyQ Promoter—Modified cryIIIA mRNA Processing/Stabilizing Sequence An amyQ promoter linked to a modified cryIIIA mRNA processing/stabilizing sequence was constructed. Plasmid pNBT55 was linearized by digestion with Sca I. *Bacillus subtilis* 168Δ4 was transformed with the linearized plasmid according to the procedure of Anagnostopoulos and Spizizen, 1961, supra, and transformants were selected for chloramphenicol resistance on TBAB chloramphenicol plates at 37° C. Chloramphenicol-resistant transformants were screened for protease production by patching colonies onto TBAB milk plates and scoring for clearing zones and also for neomycin sensitivity by patching colonies onto TBAB neomycin plates at 37° C. to confirm that the DNA had inserted into the amyE gene of the *Bacillus subtilis* chromosome by double crossover. A chloramphenicol resistant, neomycin sensitive, protease-producing transformant (with the P$_{amyQ}$/mod. cryIIIA stab/aprH cassette inserted at the amyE locus) was identified and designated *Bacillus subtilis* BW199.

Example 6

Construction of an amyQ Promoter—Wild-Type cryIIIA mRNA Processing/Stabilizing Sequence An amyQ promoter linked to a wild-type cryIIIA mRNA processing/stabilizing sequence was constructed. Plasmid pNBT3 was digested with Pac I, and the ends were blunted using T4 DNA polymerase and dNTPs. The blunt-ended plasmid was then digested with Hind III and analyzed by 0.8% agarose electrophoresis in TBE buffer, and an approximately 1067 bp fragment, bearing the wild-type cryIIIA mRNA processing/stabilizing sequence and *Bacillus clausii* alkaline protease gene (aprH) N-terminal coding region, was purified using a QIAQUICK® Gel Extraction Kit.

Figure 5:
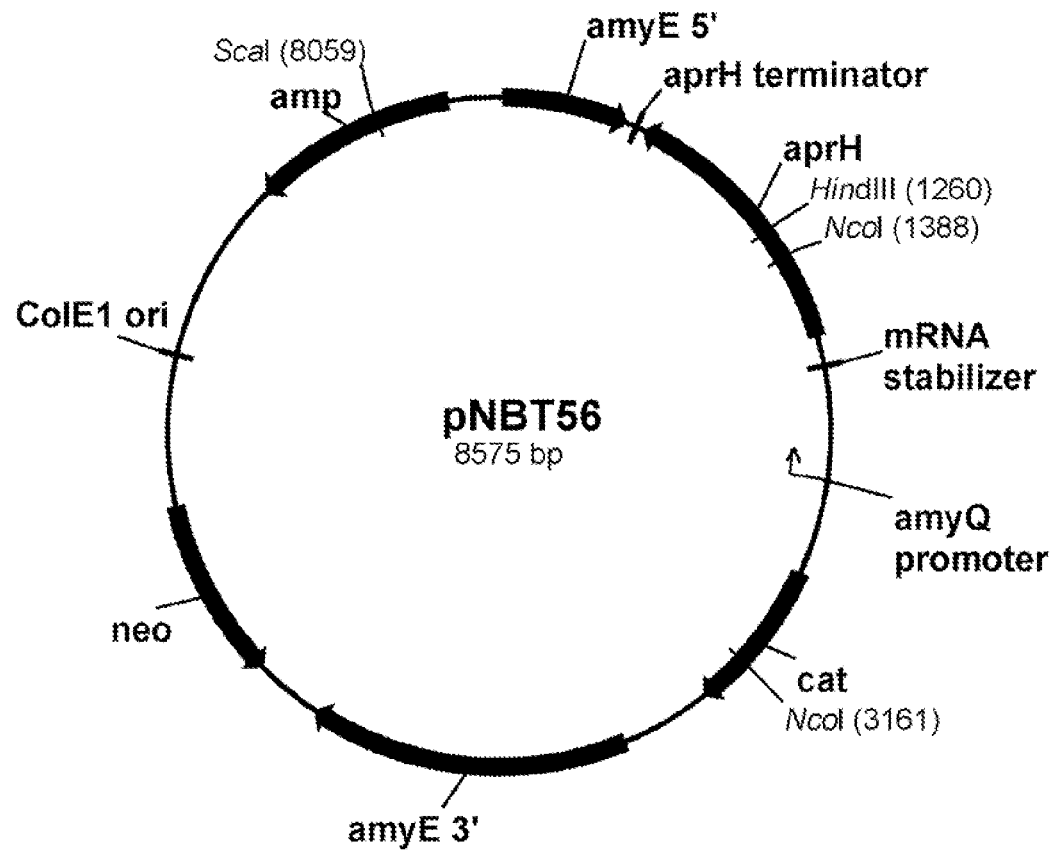
FIG. 5 shows a restriction map of pNBT56.

The pNBT48 vector fragment of approximately 7601 bp (Example 4) and the wild-type cryIIIA mRNA processing/stabilizing sequence fragment of approximately 1067 bp were ligated together with T4 DNA ligase according to the manufacturer's instructions, and $E.\ coli$ DH5α cells were transformed with the ligation according to the manufacturer's instructions, selecting for ampicillin resistance on 2×YT ampicillin plates at 37° C. Plasmid DNA from several transformants was purified using a BIOROBOT® 9600 and analyzed by restriction enzyme digestion with Nco I followed 0.8% agarose electrophoresis in TBE buffer. One plasmid that yielded an expected DNA fragment size of approximately 1800 bp was identified and designated pNBT56 (pDG268ΔNeo-P$_{amyQ}$/cryIIIA stab/aprH) (FIG. 5).

Example 7

Construction of an amyQ Promoter—Wild-Type cryIIIA mRNA Processing/Stabilizing Sequence An amyQ promoter linked to a wild-type cryIIIA mRNA processing/stabilizing sequence was constructed. Plasmid pNBT56 was linearized by digestion with Sca I. *Bacillus subtilis* 168Δ4 was transformed with the linearized plasmid according to the procedure of Anagnostopoulos and Spizizen, 1961, supra, and transformants were selected for chloramphenicol resistance on TBAB chloramphenicol plates at 37° C. Chloramphenicol-resistant transformants were screened for protease production by patching colonies onto TBAB milk plates and scoring for clearing zones and also for neomycin sensitivity by patching colonies onto TBAB neomycin plates at 37° C. to confirm that the DNA had inserted into the amyE gene of the *Bacillus subtilis* chromosome by double crossover. A chloramphenicol resistant, neomycin sensitive, protease-producing transformant (with the P$_{amyQ}$/cryIIIA stab/aprH cassette inserted at the amyE locus) was identified and designated *Bacillus subtilis* BW198.

Example 8

Evaluation of an amyQ Promoter—Modified cryIIIA mRNA Processing/Stabilizing Sequence Production of *Bacillus clausii* alkaline protease (AprH) by *Bacillus subtilis* strain BW199 was compared to the isogenic strain, *Bacillus subtilis* strain BW198, which utilizes the wild-type cryIIIA mRNA processing/stabilizing sequence. Both strains were grown at 37° C. in quadruplicate in 250 ml shake flasks containing 25 ml of PS-1 medium. One ml samples were removed on days 3 (T1), 4 (T2), and 5 (T3); and clarified supernatants were assayed for protease activity.

Protease activity was measured according to the following procedure. Culture supernatants were diluted appropriately in sample buffer (0.01% TWEEN®, 100 mM TRIS pH 8.5) followed by a series dilution from 1-fold to ⅓-fold to ⅕-fold of the diluted sample. *Bacillus clausii* alkaline protease standard (Novozymes A/S, Bagsvaed, Denmark; 4.260 NPU/g) was diluted in sample buffer accordingly to establish a linear standard curve. A total of 20 μl of each dilution including standard was transferred to a 96-well flat-bottom plate. Two hundred microliters of a Suc-Ala-Ala-Pro-Phe-pNA substrate solution (100 mg of Suc-Ala-Ala-Pro-Phe-pNA per ml DMSO diluted 1:55.6 in 100 mM TRIS pH 8.5) was added to each well, and the plate was incubated at ambient temperature for 10 minutes. During the incubation the rate of the reaction was measured at 405 nm using a BIOMEK® 3000 (Beckman Coulter, Inc. Fullerton Calif., USA). Sample concentrations were determined by extrapolation from the generated standard curve.

Figure 6:
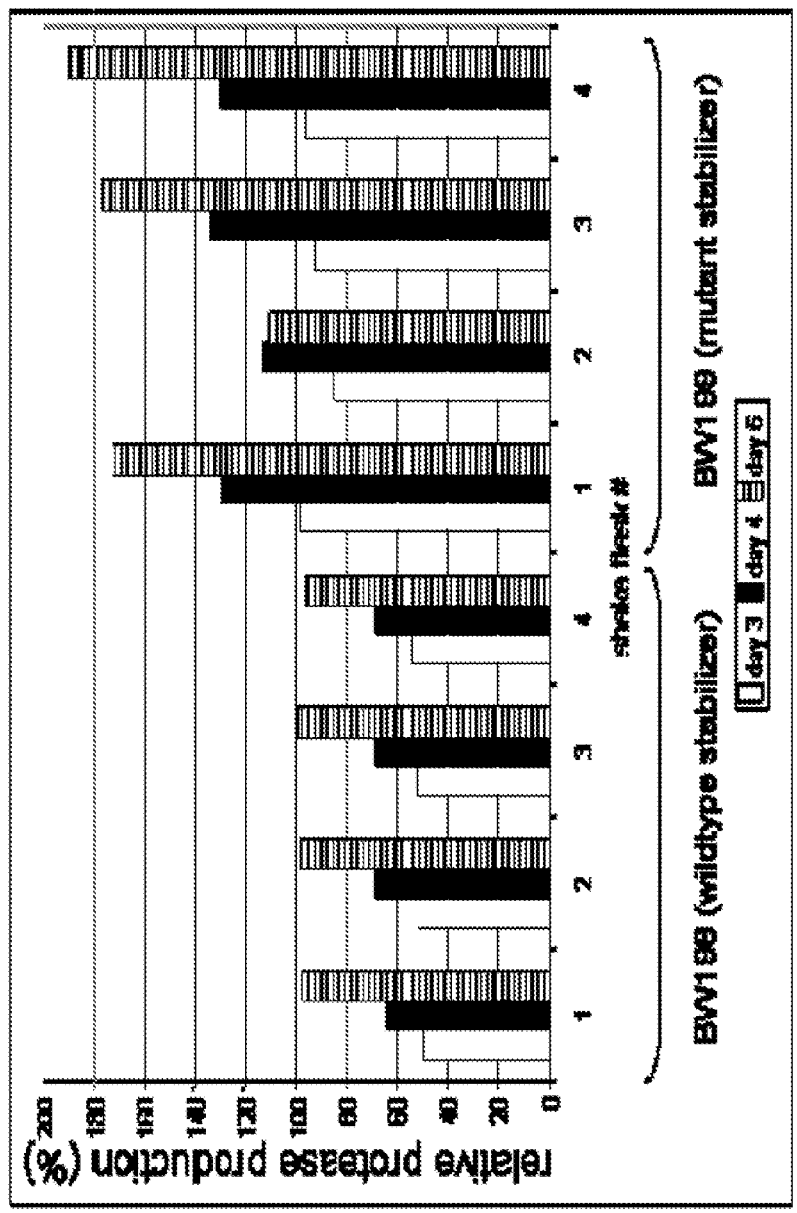
FIG. 6 shows relative *Bacillus clausii* alkaline protease (AprH) activity in shake flasks obtained from *Bacillus subtilis* strains BW198 ($P_{amyQ}$/cryIIIA stab/aprH expression cassette) and BW199 ($P_{amyQ}$/mod. cryIIIA stab/aprH expression cassette).

The relative results are shown in FIG. 6. *Bacillus subtilis* cells harboring the modified cryIIIA mRNA processing/stabilizing sequence produced on average approximately 65% more *Bacillus clausii* alkaline protease by day 5 compared to cells harboring the wild-type cryIIIA mRNA processing/stabilizing sequence. Thus, in comparison to the wild-type cryIIIA mRNA processing/stabilizing sequence, the modified cryIIIA mRNA processing/stabilizing sequence provided a significant increase in productivity.

Example 9

Figure 7:
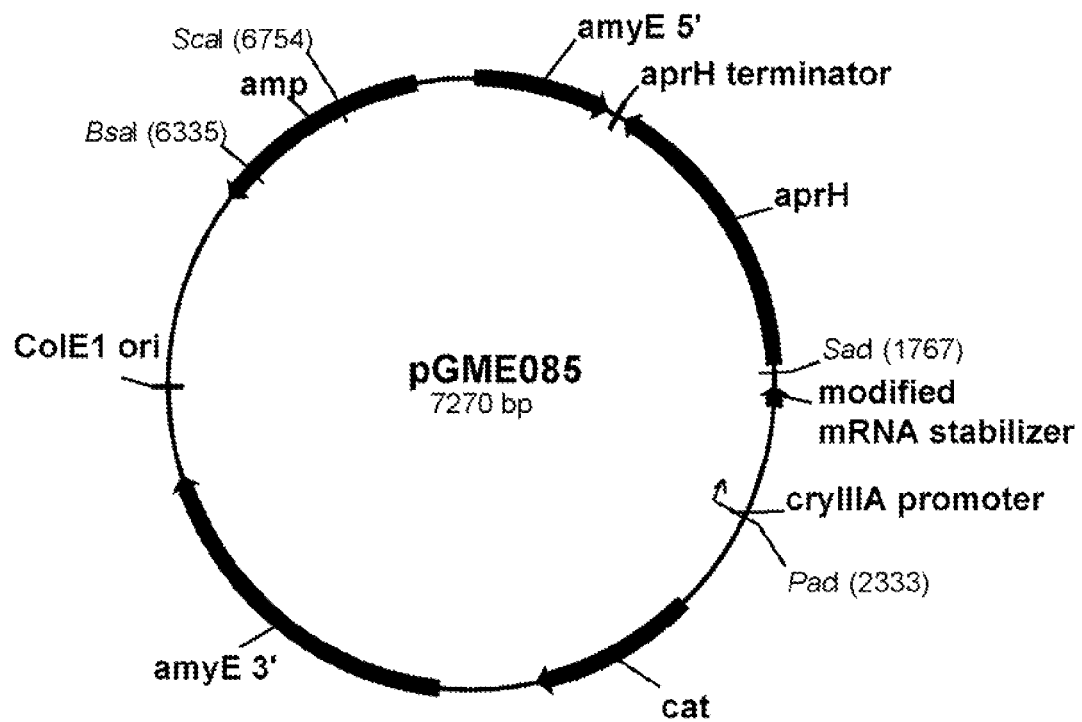
FIG. 7 shows a restriction map of pGME085.

Construction of an cryIIIA Promoter—Modified cryIIIA mRNA Processing/Stabilizing Sequence A cryIIIA promoter linked to a modified cryIIIA mRNA processing/stabilizing sequence was constructed. Plasmid pCR2.1-stabx2 was digested with Fac I and Sac I and analyzed by 0.8% agarose electrophoresis in TBE buffer, and an approximately 568 bp fragment bearing the modified cryIIIA mRNA processing/stabilizing sequence was purified using a QIAQUICK® Gel Extraction Kit. Plasmid pNBT2 was digested with Pac I and Sac I and analyzed by 0.8% agarose electrophoresis in TBE buffer, and an approximately 6704 bp vector fragment was purified using a QIAQUICK® Gel Extraction Kit. The pNBT2 vector fragment and the modified cryIIIA mRNA processing/stabilizing sequence fragment were ligated together with T4 DNA ligase according to the manufacturer's instructions, and *E. coli* XL10-Gold® Ultracompetent cells were transformed with the ligation according to the manufacturer's instructions, selecting for ampicillin resistance on 2×YT ampicillin plates at 37° C. Plasmid DNA from several transformants was purified using a BIOROBOT® 9600 and tested by digestion with Pac I and Eco RI followed by 0.8% agarose electrophoresis in TBE buffer. One plasmid with expected fragments of approximately 5882 bp and 1388 bp was designated pGME085 (FIG. 7).

Plasmid pGME085 was linearized by digestion with Bsa I and Sca I and analyzed by 0.8% agarose electrophoresis in TBE buffer, and an approximately 6851 bp vector fragment was purified using a QIAQUICK® Gel Extraction Kit. *Bacillus subtilis* 168Δ4 was transformed with the purified plasmid fragment according to the procedure of Anagnostopoulos and Spizizen, 1961, supra, and transformants were selected for chloramphenicol resistance on TBAB chloramphenicol plates at 37° C. One transformant with the $P_{cryIIIA}$/mod. cryIIIA stab/aprH cassette inserted at the amyL locus was designated *Bacillus subtilis* GME202.

Example 10

Figure 8:
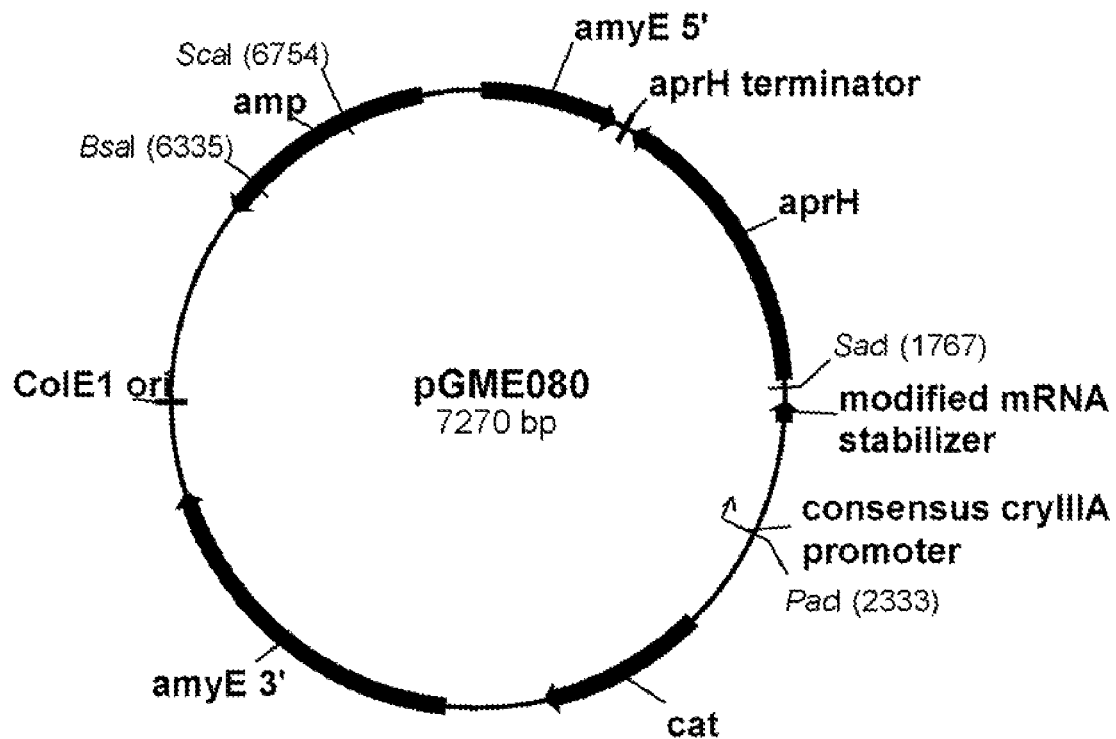
FIG. 8 shows a restriction map of pGME080.

Construction of a Consensus cryIIIA Promoter—Modified cryIIIA mRNA Processing/Stabilizing Sequence A cryIIIA promoter comprising consensus −35 and −10 regions linked to a modified cryIIIA mRNA processing/stabilizing sequence was constructed. Plasmid pGME079 was digested with Pac I and Sac I and analyzed by 0.8% agarose electrophoresis in TBE buffer, and an approximately 6704 bp vector fragment was purified using a QIAQUICK® Gel Extraction Kit. The pGME079 vector fragment and the modified cryIIIA mRNA processing/stabilizing sequence fragment of approximately 568 bp (Example 9) were ligated together with T4 DNA ligase according to the manufacturer's instructions, and *E. coli* XL10-GOLD® Ultracompetent cells were transformed with the ligation according to the manufacturer's instructions, selecting for ampicillin resistance on 2×YT ampicillin plates at 37° C. Plasmid DNA from several transformants was purified using a BIOROBOT® 9600 and tested by digestion with Pac I and Sac I followed by 0.8% agarose electrophoresis in TBE buffer. One plasmid with expected fragments of approximately 6704 bp and 566 bp was designated pGME080 (FIG. 8).

Plasmid pGME080 was linearized by digestion with Bsa I and Sac I and analyzed by 0.8% agarose electrophoresis in TBE buffer, and an approximately 6851 bp vector fragment was purified using a QIAQUICK® Gel Extraction Kit. *Bacillus subtilis* 168Δ4 was transformed with the purified plasmid fragment according to the procedure of Anagnostopoulos and Spizizen, 1961, supra, and transformants were selected for chloramphenicol resistance on TBAB chloramphenicol plates at 37° C. One transformant with the $P_{consensus\ cryIIIA}$/mod. cryIIIA stab/aprH cassette inserted at the amyL locus was designated *Bacillus subtilis* GME203.

Example 11

Evaluation of *Bacillus subtilis* Strains GME201, GME202, and GME203

A *Bacillus subtilis* strain bearing the wild-type cryIIIA promoter and unmodified (wild-type) cryIIIA mRNA processing/stabilizing sequence was created to serve as a baseline control for comparison to *Bacillus subtilis* strains GME201, GME202, and GME203. Genomic DNA was isolated from *Bacillus subtilis* PL1801 spoIIE::Tn917 comprising the $P_{cryIIIA}$/cryIIIA stab/aprH cassette inserted at the amyE locus (U.S. Pat. No. 5,955,310), according to the procedure of Pitcher et al., 1989, *Lett. Appl. Microbiol.* 8: 151-156. *Bacillus subtilis* 168Δ4 was transformed with the genomic DNA according to the procedure of Anagnostopoulos and Spizizen, 1961, supra, and transformants were selected for chloramphenicol resistance on TBAB chloramphenicol plates at 37° C. One such transformant was designated *Bacillus subtilis* GME200.

*Bacillus subtilis* strains GME200, GME201, GME202, and GME203 were grown at 37° C. in triplicate in 250 ml shake flasks containing 25 ml of PS-1 medium. One ml samples were removed on days 3 (T1), 4 (T2), and 5 (T3) and clarified supernatants were assayed for protease activity, as described in Example 8.

Figure 9:
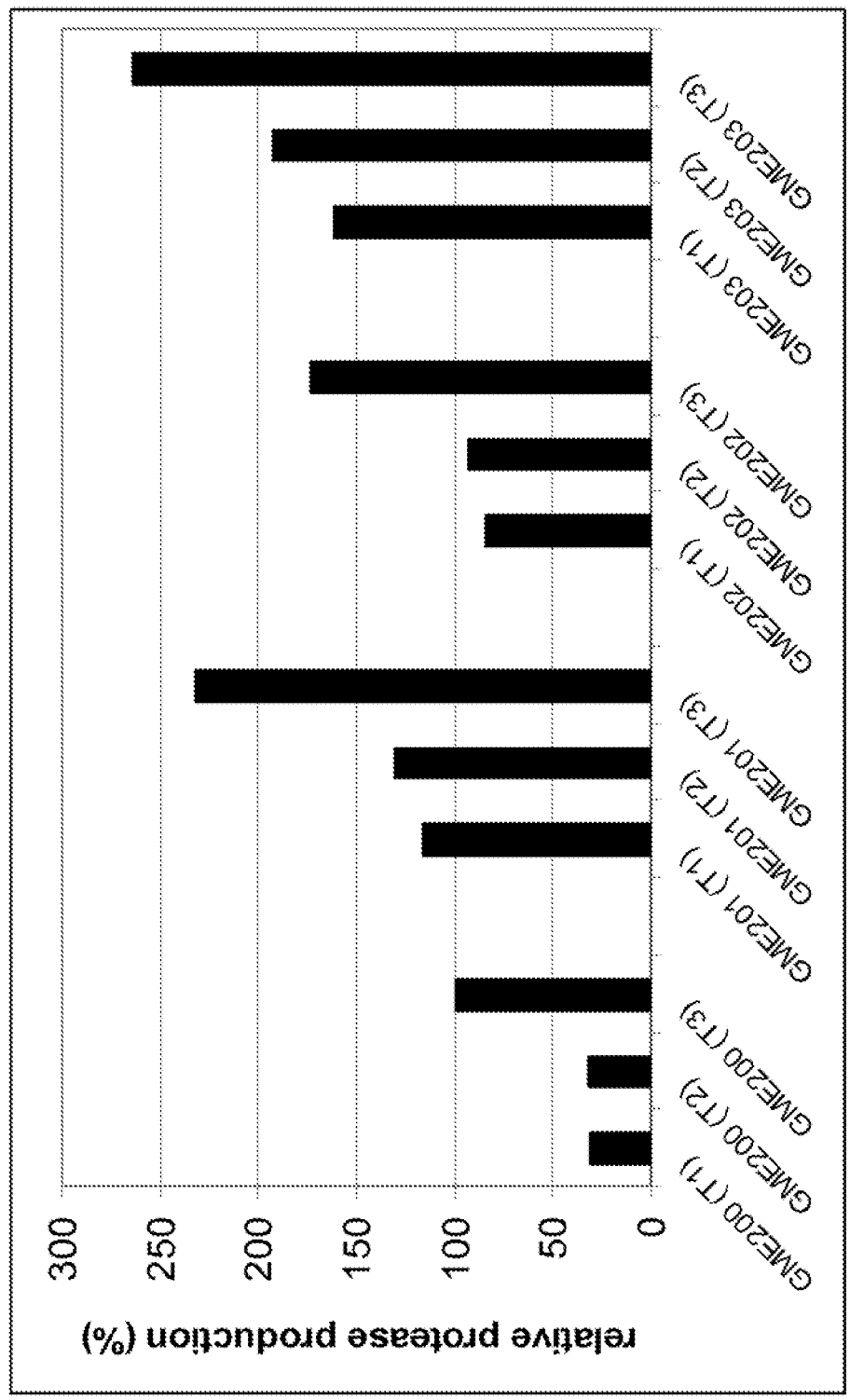
FIG. 9 shows relative *Bacillus clausii* alkaline protease (AprH) activity in shake flasks obtained from *Bacillus subtilis* strains GME200 (wild-type $P_{cryIIIA}$/cryIIIA stab/aprH expression cassette), GME201 ($P_{consensus\ cryIIIA}$/cryIIIA stab/aprH expression cassette), GME202 ($P_{cryIIIA}$/mod. cryIIIA stab/aprH expression cassette), and GME203 ($P_{consensus\ cryIIIA}$/mod. cryIIIA stab/aprH expression cassette).

Mean relative *Bacillus clausii* alkaline protease production values for the above cultures are shown in FIG. 9. The results demonstrated that strains in which the protease was expressed from the constructs comprising a consensus cryIIIA promoter and/or a modified cryIIIA mRNA processing/stabilizing sequence (*Bacillus subtilis* GME201, GME202, and GME203) all produced more protease than *Bacillus subtilis* GME200, in which the protease was expressed from the wild-type cryIIIA promoter linked to an unmodified cryIIIA mRNA processing/stabilizing sequence. *Bacillus subtilis* GME202 provided a 73% increase in comparison to *Bacillus subtilis* GME200, while *Bacillus subtilis* GME203 provided a 13% increase relative to *Bacillus subtilis* GME201. *Bacillus subtilis* GME201 provided a 133% increase in comparison to *Bacillus subtilis* GME200, while *Bacillus subtilis* GME203 provided a 53% increase relative to *Bacillus subtilis* GME202. The highest productivity was from the promoter variant of *Bacillus subtilis* GME203, comprising both the consensus $P_{cryIIIA}$ and the modified cryIIIA mRNA processing/stabilizing sequence, which provided a 164% increase in comparison to *Bacillus subtilis* GME200.

Example 12

Construction of *Bacillus licheniformis* Host Strain MDT283

*Bacillus licheniformis* SJ1904 (WO 94/014968) was transformed with C-component gene deletion plasmid pNBT38 (U.S. Published Application 20050221446) by electroporation according to the procedure of Xue et al., 1999, *J. Microbiol. Methods* 34(3): 183-191. Briefly, 1-5 ml of an overnight culture of *Bacillus licheniformis* grown in LBS medium was used to inoculate 50 ml of fresh LBS medium, and the culture was incubated at 37° C. and 250 rpm. The culture was grown to stationary phase, and cells were harvested by centrifugation at 6500×g when the culture experienced an increase in growth rate after a period of slow growth (1-3 hours after the end of exponential growth). Cells were washed twice with 50 ml of ice-cold MSG (0.5 M mannitol, 0.5 M sorbitol, 10% glycerol) and resuspended in approximately 750 µl of MSG. Cells were transformed as follows or stored at −20° C. Sixty µl of electrocompetent cells were mixed with plasmid DNA in an electroporation cuvette with a 1-mm electrode gap and subjected to an electrical pulse using a GENE PULSER® set to 25 µF, 200Ω, and 1.0 kV. Electroporated cells were then transferred to 950 µl of LBSM medium containing 0.2 µg of erythromycin per ml for induction of erythromycin resistance. The transformants were incubated for 2.5-3 hours at 34° C. and 250 rpm and then selected for erythromycin resistance on TBAB erythromycin/lincomycin plates at 34° C.

One such transformant was grown on TBAB plates with erythromycin selection at 50° C. in order to select for integration of pNBT38 into the chromosome at the C-component gene. One such integrant was then grown in VY medium without selection at 34° C. in order to permit excision and loss of the integrated plasmid. The culture was plated on LB plates at 37° C., and colonies were screened for sensitivity to erythromycin, indicating loss of the plasmid. Several erythromycin-sensitive clones were tested by PCR with primers 991173 and 991176, as described in Example 2.

```
Primer 991173:
5'-GAATTCGACGGCTTCCCGTGCGCC-3'    (SEQ ID NO: 15)

Primer 991176:
5'-AAGCTTCCATTCAAACCTGGTGAGGAAG-3' (SEQ ID NO: 16)
```

One clone in which the PCR amplified a fragment of approximately 606 bp, indicating deletion of the C-component protease gene from the chromosome, was designated *Bacillus licheniformis* MDT283.

Example 13

Construction of Plasmid Vectors pMDT131 and pMDT160

Plasmids pMDT131 and pMDT160 were constructed to create temperature-sensitive plasmids conferring chloramphenicol resistance.

Figure 10:
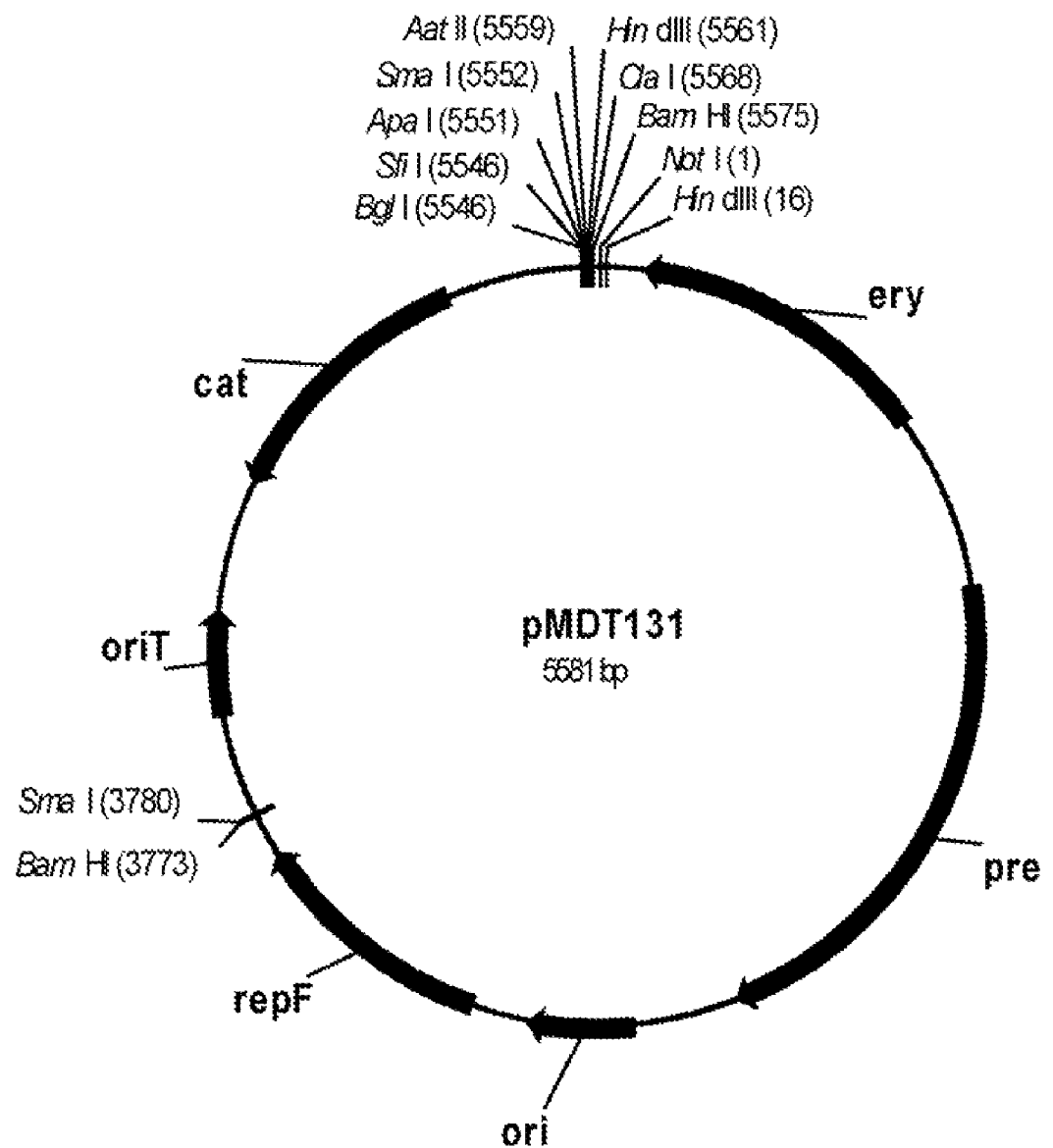
FIG. 10 shows a restriction map of pMDT131.

Plasmid pMDT131 was constructed by insertion of a chloramphenicol resistance gene into plasmid pMRT074 (U.S. Published Application 20030175902). Plasmid pMRT074 was digested with Eco RI, and the ends were blunted by incubation for 20 minutes at 11° C. with T4 DNA polymerase (Roche Diagnostics Corporation, Indianapolis, Ind., USA) and 25 µM of each dNTP, followed by heat-inactivation of the polymerase by incubation for 10 minutes at 75° C. The plasmid was then digested with Not I, analyzed by 0.8% agarose electrophoresis in TBE buffer, and a vector fragment of approximately 4355 bp was purified using a QIAQUICK® Gel Extraction Kit. Plasmid pNBT1 (pDG268MCS; U.S. Pat. No. 6,255,076) was digested with Eco 47II and Not I, analyzed by 0.8% agarose electrophoresis in TBE buffer, and a fragment of approximately 1222 bp, bearing a cat gene and a multiple cloning site, was purified using a QIAQUICK® Gel Extraction Kit. The pMRT074 vector fragment was ligated with the cat fragment using T4 DNA ligase according to the manufacturer's instructions, and *Bacillus subtilis* 168Δ4 was transformed with the ligation according to the procedure of Anagnostopoulos and Spizizen, 1961, supra, selecting for chloramphenicol resistance on TBAB chloramphenicol plates at 34° C. Plasmid DNA was isolated from one transformant using a Plasmid Midi Kit (QIAGEN Inc., Valencia, Calif., USA) and confirmed by digestion with Bam HI followed by 0.8% agarose electrophoresis in TBE buffer, which yielded expected fragments of approximately 3779 bp and 1802 bp. The resulting plasmid was designated pMDT131 (FIG. 10).

Figure 11:
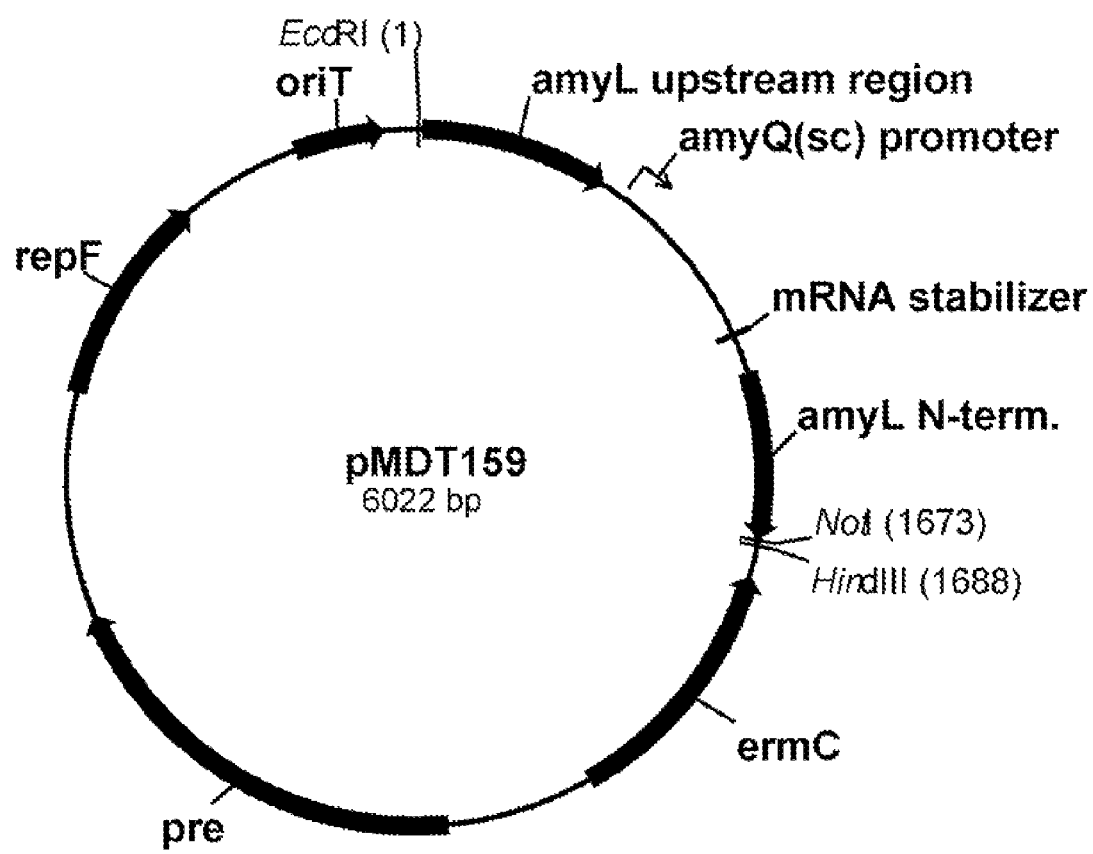
FIG. 11 shows a restriction map of pMDT159.

Plasmid pMDT159 was constructed by elimination of the Bam HI, Sma I, and Asp 718 restriction sites of pMRT074. Plasmid pMRT074 was digested with Bam HI and Asp 718, and the ends were blunted by incubation for 20 minutes at 11° C. with T4 DNA and 25 µM of each dNTP, followed by heat-inactivation of the polymerase by incubation for 10 minutes at 75° C. The digested plasmid was analyzed by 0.8% agarose electrophoresis in TBE buffer, and a vector fragment of approximately 6022 bp was purified using a QIAQUICK® Gel Extraction Kit. The purified fragment was treated with T4 DNA ligase according to the manufacturer's instructions, and *Bacillus subtilis* strain 168Δ4 was transformed with the ligation according to the procedure of Anagnostopoulos and Spizizen, 1961, supra, selecting for erythromycin resistance on TBAB erythromycin/lincomycin plates at 34° C. The resulting plasmid was designated pMDT159 (FIG. 11). Loss of the Bam HI, Sma I, and Asp 718 sites was confirmed by restriction digestion.

Figure 12:
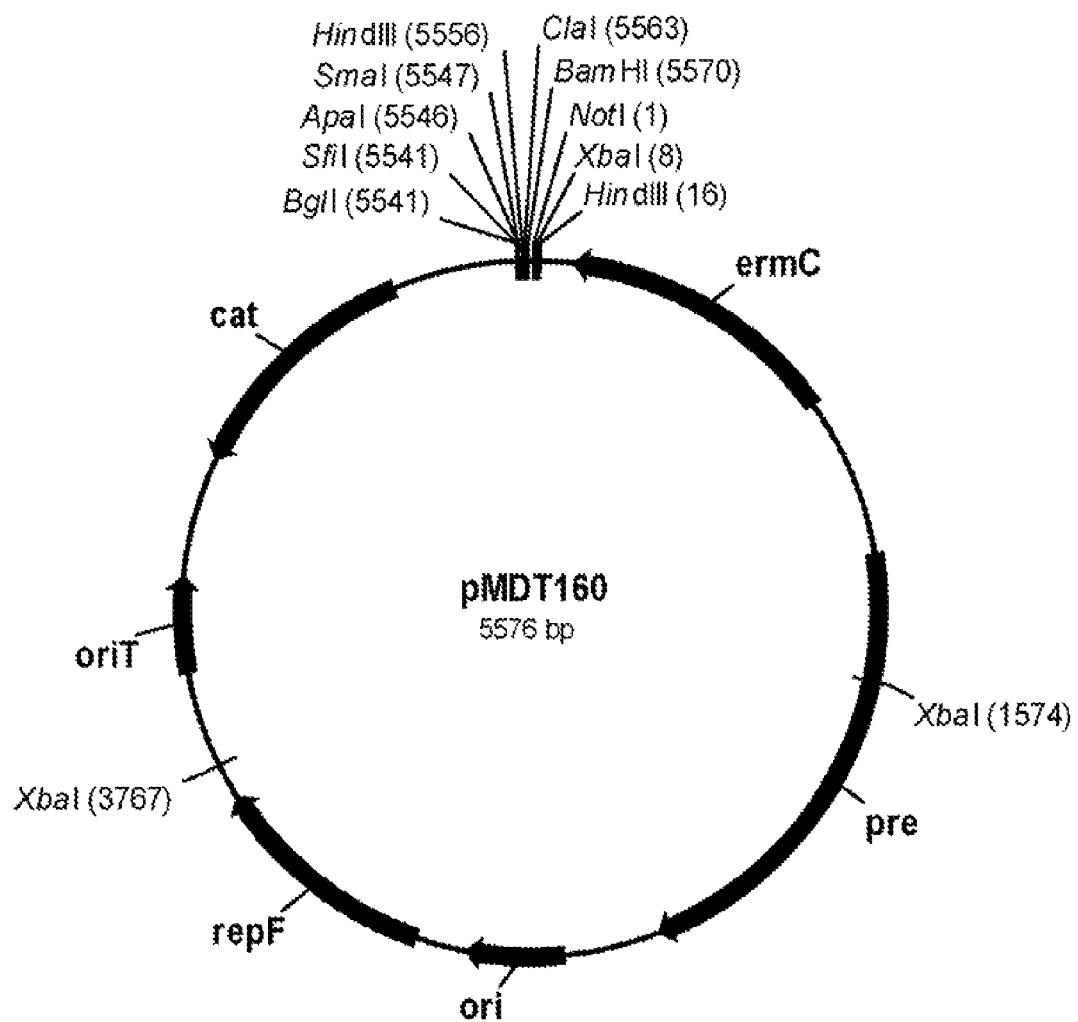
FIG. 12 shows a restriction map of pMDT160.

Plasmid pMDT160 was constructed by introduction of a chloramphenicol resistance gene into pMDT159. Plasmid pMDT159 was digested with Eco RI, and the ends were blunted by incubation for 20 minutes at 11° C. with T4 DNA polymerase and 25 µM of each dNTP, followed by heat-inactivation of the polymerase by incubation for 10 minutes at 75° C. The plasmid was then digested with Not I and analyzed by 0.8% agarose electrophoresis in TBE buffer, and a vector fragment of approximately 4354 bp was purified using a QIAQUICK® Gel Extraction Kit. Plasmid pNBT1 was digested with Eco 47III and Not I, analyzed by 0.8% agarose electrophoresis in TBE buffer, and a fragment of approximately 1222 bp bearing a cat gene and a multiple cloning site was purified using a QIAQUICK® Gel Extraction Kit. The pMRT074 vector fragment was ligated with the pNBT1 cat fragment using T4 DNA ligase as described above, and *Bacillus subtilis* 168Δ4 was transformed with the ligation according to the procedure of Anagnostopoulos and Spizizen, 1961, supra, selecting for chloramphenicol resistance on TBAB chloramphenicol plates at 34° C. Plasmid DNA was isolated from one transformant using a Plasmid Midi Kit and confirmed by digestion with Xba I followed by 0.8% agarose electrophoresis in TBE buffer, which yielded expected fragments of approximately 2193 bp, 1817 bp, and 1566 bp. The resulting plasmid was designated pMDT160 (FIG. 12).

Example 14

Construction of Plasmid pHyGe204

Figure 13:
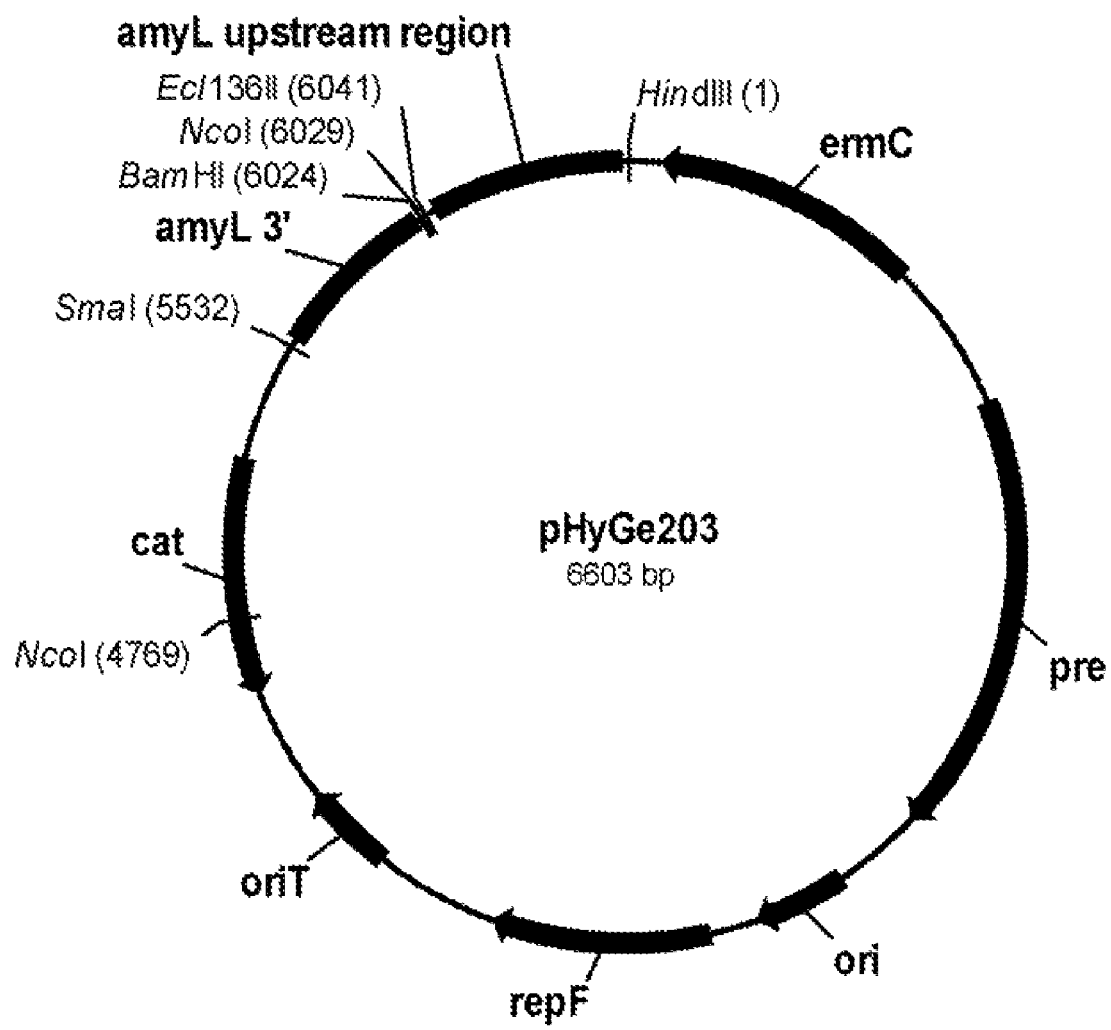
FIG. 13 shows a restriction map of pHyGe203.

Plasmid pHyGe203 was constructed by insertion of the *B. licheniformis* amyL fragments of pMRT044 (U.S. Published Application 20030175902) into plasmid vector pMDT160. Plasmid pMDT160 was digested with Sma I and Hind III and analyzed by 1.0% agarose electrophoresis in TAE (40 mM Tris-20 mM sodium acetate-1 mM EDTA pH7.2) buffer, and a vector fragment of approximately 5531 bp was purified using a QIAQUICK® Gel Extraction Kit. Plasmid pMRT044 was digested with Sma I and Hind III and analyzed by 1.0% agarose electrophoresis in TAE buffer, and a fragment of approximately 1072 bp, bearing amyL upstream and downstream fragments, was purified using a QIAQUICK® Gel Extraction Kit. The pMDT160 vector fragment and pMRT044 amyL fragment were ligated together using a Rapid Ligation Kit (Roche Diagnostics Corporation, Indianapolis, Ind., USA) according to the manufacturer's instructions, and *Bacillus subtilis* strain 168Δ4 was transformed with the ligation according to the procedure of Anagnostopoulos and Spizizen, 1961, supra, selecting for chloramphenicol resistance on TBAB chloramphenicol plates at 34° C. The resulting plasmid was designated pHyGe203 (FIG. 13). The plasmid was confirmed by digestion with Nco I followed by 1.0% agarose electrophoresis in TAE buffer, which yielded expected fragments of approximately 5343 bp and 1260 bp.

Plasmid pHyGe204 was constructed by insertion of the cryIIIA mRNA processing/stabilizing sequence and *Bacillus clausii* aprH gene of pNBT18 (pDG268MCSΔneo-long cryIIIA stab/SAV, U.S. Pat. No. 6,255,076) between the amyL upstream and downstream fragments of pHyGe203. Plasmid pHyGe203 was digested with Ecl 136II and Bam HI and analyzed by 1.0% agarose electrophoresis in TAE buffer, and a vector fragment of approximately 6586 bp was purified using a QIAQUICK® Gel Extraction Kit. Plasmid pNBT18 was digested with Pac I, and the ends were blunted by incubation for 20 minutes at 11° C. with T4 DNA polymerase and 25 µM of each dNTP. The digested plasmid was then digested with Bam HI and analyzed by 1.0% agarose electrophoresis in TAE buffer, and a fragment of approximately 1768 bp, bearing the cryIIIA mRNA processing/stabilizing sequence and *Bacillus clausii* aprH gene, was purified using a QIAQUICK® Gel Extraction Kit. The pHyGe203 vector fragment and the mRNA processing/stabilizing sequence/aprH fragment were ligated using a Rapid Ligation Kit according to the manufacturer's instructions, and *Bacillus subtilis* strain 168Δ4 was transformed with the ligation according to the procedure of Anagnostopoulos and Spizizen, 1961, supra, selecting for chloramphenicoal resistance on TBAB chloramphenicol plates at 34° C. The resulting plasmid was designated pHyGe204. The plasmid was confirmed by digestion with Nco I and with Hind III followed by 1.0% agarose electrophoresis in TAE buffer, which yielded expected fragments of approximately 6249 bp and 2103 bp for Nco I and 6743 bp and 1609 bp for Hind III.

Example 15

Construction of Plasmid pHyGe205

Figure 14:
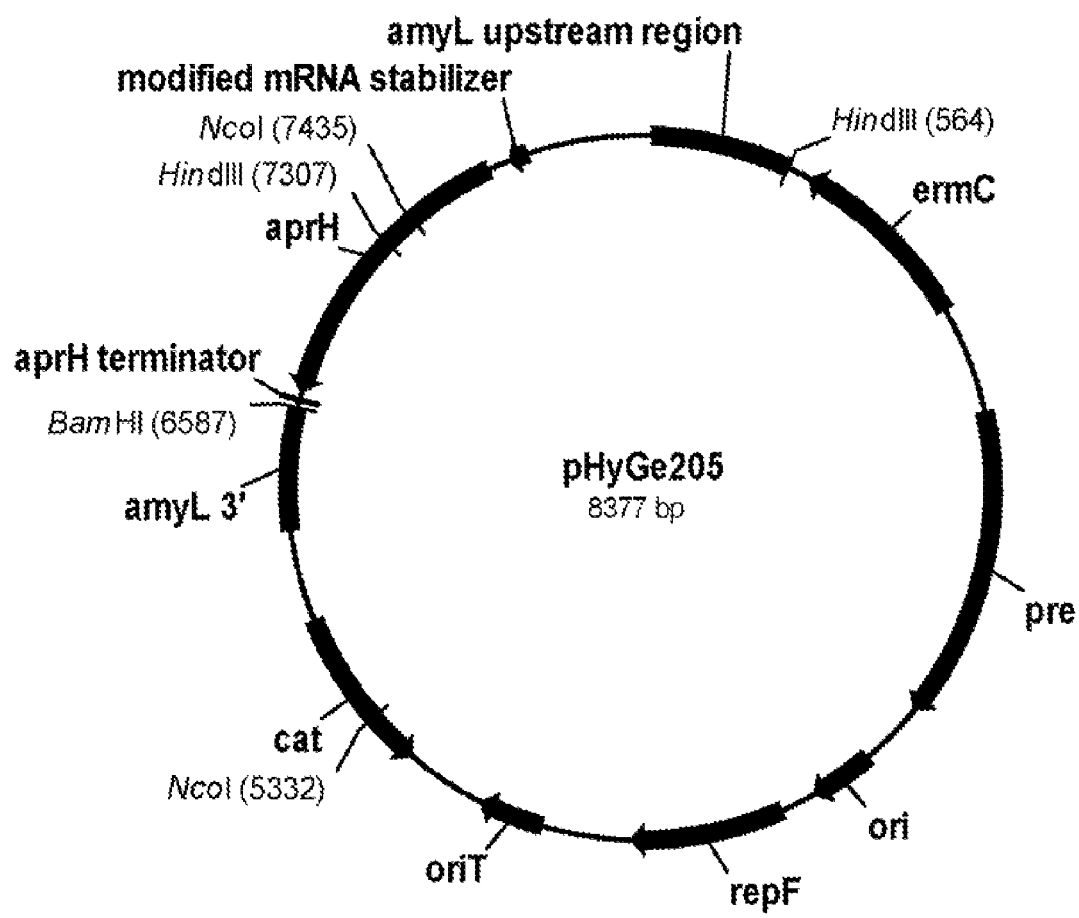
FIG. 14 shows a restriction map of pHyGe205.

Plasmid pHyGe205 was constructed by insertion of the modified cryIIIA mRNA processing/stabilizing sequence and *Bacillus clausii* aprH gene of pGME080 between the amyL upstream and downstream fragments of pHyGe203. Plasmid pGME080 was digested with Pac I, and the ends were blunted by incubation for 20 minutes at 11° C. with T4 DNA polymerase and 25 µM of each dNTP. The digested plasmid was then digested with Bam HI and analyzed by 1.0% agarose electrophoresis in TAE buffer, and a fragment of approximately 1793 bp, bearing the modified cryIIIA mRNA processing/stabilizing sequence and *Bacillus clausii* aprH gene, was purified using a QIAQUICK® Gel Extraction Kit. The pHyGe203 Ecl 136II/Bam HI vector fragment (described above) and the modified mRNA processing/stabilizing sequence/aprH fragment were ligated using a Rapid Ligation Kit according to the manufacturer's instructions, and *Bacillus subtilis* strain 168Δ4 was transformed with the ligation according to the procedure of Anagnostopoulos and Spizizen, 1961, supra, selecting for chloramphenicol resistance on TBAB chloramphenicol plates at 34° C. The resulting plasmid was designated pHyGe205 (FIG. 14). The plasmid was confirmed by digestion with Nco I and with Hind III followed by 1.0% agarose electrophoresis in TAE buffer, which yielded expected fragments of approximately 6274 bp and 2103 bp for Nco 1 and 6743 bp and 1634 bp for Hind III.

Example 16

Construction of Plasmid pHyGe206

A fragment bearing a triple tandem promoter was cloned by PCR from *Bacillus licheniformis* strain MDT220 (U.S. Published Application 20050221446). Genomic DNA was isolated from *Bacillus licheniformis* strain MDT220 according to the procedure of Pitcher et al., 1989, supra. A fragment bearing the $P_{amyL4199}/P_{short\ consensus\ amyQ}/P_{cryIIIA}$ triple tandem promoter was PCR amplified from *Bacillus licheniformis* MDT220 genomic DNA using oligonucleotide primers 994112 and 060762 with an Expand High Fidelity PCR System (Roche Diagnostics Corporation, Indianapolis, Ind., USA) according to manufacturer's instructions. The PCR was performed in an Eppendorf Mastercylcer Gradient thermal cycler programmed for 1 cycle at 9400 for 2 minutes; 11 cycles each at 94° C. for 30 seconds, 58° C. for 30 seconds, 72° C. for 1 minute 15 seconds; 15 cycles each at 94° C. for 30 seconds, 58° C. for 30 seconds, 72° C. for 1 minute 15 seconds plus 5 seconds for each successive cycle; and 1 cycle at 72° C. for 7 minutes.

```
Primer 994112:                    (SEQ ID NO: 17)
5'-GCGGCCGCTCGCTTTCCAATCTGA-3'

Primer 060762:                    (SEQ ID NO: 18)
5'-ATCGATAATAATTTATACACTATTCTATTGG-3'
```

Figure 15:
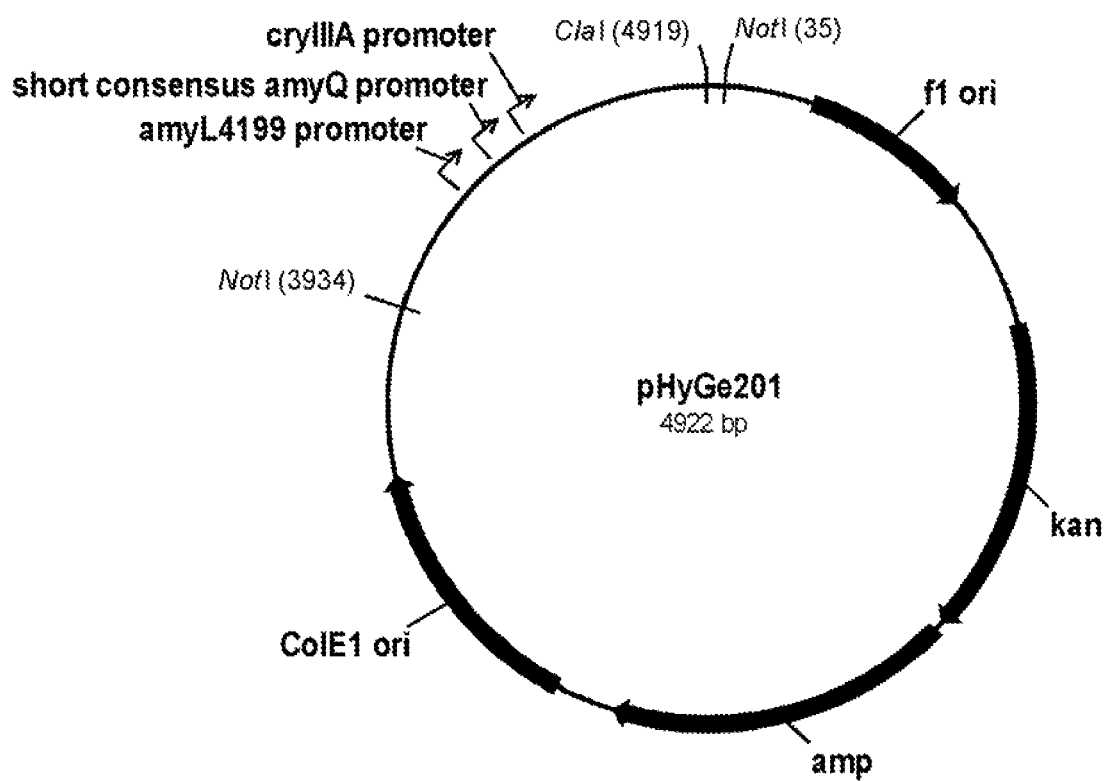
FIG. 15 shows a restriction map of pHyGe201.

The resulting PCR product of approximately 991 bp was purified using a QIAQUICK® PCR Purification Kit (QIAGEN inc., Valencia, Calif.) according to the manufacturer's instructions, cloned into pCR2.1 using a TOPO® TA Cloning Kit, and transformed into ONE SHOT® TOP10 Chemically Competent *E. coli* cells according to the manufacturer's instructions. The resulting plasmid was designated pHyGe201 (FIG. 15). The sequence of the triple tandem promoter in pHyGe201 was confirmed by DNA sequencing.

Figure 16:
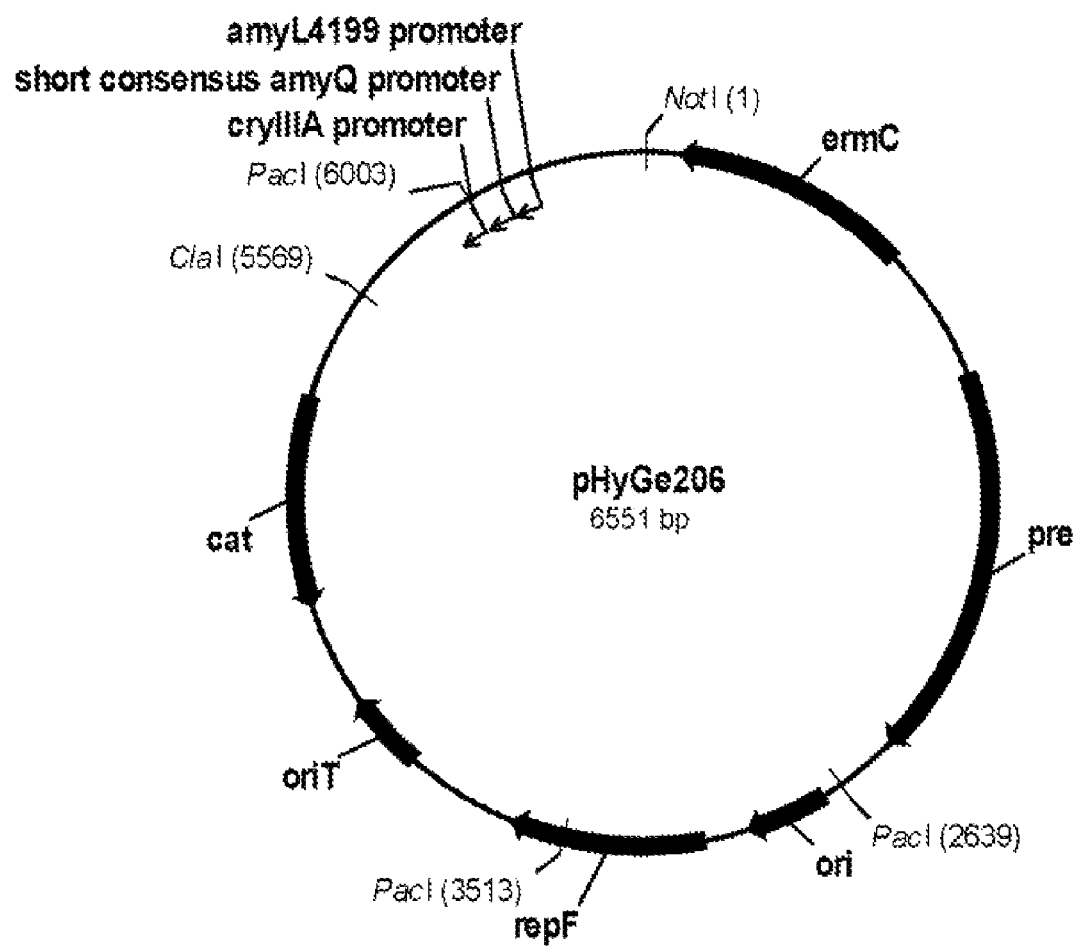
FIG. 16 shows a restriction map of pHyGe206.

Plasmid pHyGe206 was constructed by insertion of a triple tandem promoter from plasmid pHyGe201 into plasmid vector pMDT131. Plasmid pMDT131 was digested with Cla I and Not I and analyzed by 1.0% agarose electrophoresis in TAE buffer, and a vector fragment of approximately 5568 bp was purified using a QIAQUICK® Gel Extraction Kit. Plasmid pHyGe201 was digested with Cla I and Not I and analyzed by 1.0% agarose electrophoresis in TAE buffer, and a vector fragment of approximately 983 bp, bearing a triple tandem promoter, was purified using a QIAQUICK® Gel Extraction Kit. The pMDT131 vector fragment and the triple tandem promoter fragment were ligated using a Rapid Ligation Kit according to the manufacturer's instructions, and *Bacillus subtilis* strain 168Δ4 was transformed with the ligation according to the procedure of Anagnostopoulos and Spizizen, 1961, supra, selecting for chloramphenicol resistance on TBAB chloramphenicol plates at 34° C. The resulting plasmid was designated pHyGe206 (FIG. 16). The plasmid was confirmed by digestion with Pac I followed by 1.0% agarose electrophoresis in TAE buffer, which yielded expected fragments of approximately 3187 bp, 2490 bp, and 874 bp.

Example 17

Construction of *Bacillus licheniformis* Strains with a cryIIIA mRNA Processing/Stabilizing Sequence and *Bacillus clausii* aprH Gene Inserted at the amyL Locus

*Bacillus licheniformis* strain MDT283 was transformed with plasmid pHyGe204 as described in Example 12. Electroporated cells were then transferred to 950 μl of LBSM medium containing 0.2 μg/ml erythromycin for induction of erythromycin resistance. The transformants were incubated for 2, 5-3 hours at 34° C. and 250 rpm and then selected for erythromycin resistance on TBAB erythromycin/lincomycin plates at 34° C.

One such transformant was grown on TBAB plates with erythromycin selection at 50° C. in order to select for integration of pHyGe204 into the chromosome at the amyL locus. One such integrant was then grown in VY medium without selection at 34° C. in order to permit excision and loss of the integrated plasmid. The culture was plated on LB plates at 37° C., and colonies were screened for sensitivity to erythromycin, indicating loss of the plasmid. Erythromycin-sensitive colonies were screened for inability to form a zone of clearing on agar containing 0.5% starch azure (Sigma-Aldrich, St. Louis, Mo., USA), indicating that the amyL gene had been replaced by the cryIIIA mRNA processing/stabilizing sequence and *Bacillus clausii* aprH gene, insertion of the cryIIIA mRNA processing/stabilizing sequence and aprH gene at the amyL locus was confirmed by PCR using primer 950872, which binds upstream of amyL, and primer 950984, which binds within the aprH coding region. One such strain was designated *Bacillus licheniformis* HyGe208.

```
Primer 950872:                    (SEQ ID NO: 19)
5'-CCAGGCCTTAAGGGCCGCATGCGTCCTTCTTTGTGCT-3'

Primer 950964:                    (SEQ ID NO: 20)
5'-CGACTTCCTCTTCCTCAGAG-3'
```

*Bacillus licheniformis* strain MDT283 was transformed with plasmid pHyGe205 by electroporation as described above, selecting for erythromycin resistance on TBAB erythromycin/lincomycin plates at 34° C. One such transformant was grown on TBAB plates with erythromycin selection at 50° C. in order to select for integration of pHyGe205 into the chromosome at the amyL locus. One such integrant was then grown in VY medium without selection at 34° C. in order to permit excision and loss of the integrated plasmid. The culture was plated on LB plates at 37° C., and colonies were screened for sensitivity to erythromycin, indicating loss of the plasmid. Erythromycin-sensitive colonies were screened for inability to form a zone of clearing on agar containing 0.5% starch azure, indicating that the amyL gene had been replaced by the modified cryIIIA mRNA processing/stabilizing sequence and *Bacillus clausii* aprH gene. Insertion of the cryIIIA mRNA processing/stabilizing sequence and aprH gene at the amyL locus was confirmed by PCR using primers 950872 and 950984 shown above. One such strain was designated *Bacillus licheniformis* HyGe209.

Example 18

Construction of *Bacillus licheniformis* Strains with a Triple Tandem Promoter and *Bacillus clausii* aprH Gene Inserted at the amyL Locus

*Bacillus licheniformis* strains HyGe208 and HyGe209 were transformed with plasmid pHyGe206 as described in Example 12, selecting for erythromycin resistance on TBAB erythromycin/lincomycin plates at 34° C. One such transformant was grown on TBAB plates with erythromycin selection at 50° C. in order to select for integration of pHyGe205 into the chromosome at the amyL locus. One such integrant was then grown in VY medium without selection at 34° C. in order to permit excision and loss of the integrated plasmid. The culture was plated on LB plates at 37° C., and colonies were screened for sensitivity to erythromycin, indicating loss of the plasmid. Erythromycin-sensitive colonies were screened for ability to form large zones of clearing on agar containing 1% nonfat dry milk, indicating that the triple tandem promoter had been inserted upstream of the *Bacillus clausii* aprH gene. The presence of an aprH expression cassette at the amyL locus was confirmed by PCR using primer 950872 shown above, which binds upstream of amyL, and primer 991797, which binds downstream of amyL. One such strain derived from *Bacillus licheniformis* HyGe208 and had an expected PCR product of approximately 3094 bp was designated *Bacillus licheniformis* HyGe210: one derived from *Bacillus licheniformis* HyGe209 and had an expected PCR product of approximately 3119 bp was designated *Bacillus licheniformis* HyGe211, *Bacillus licheniformis* strain HyGe210 contains an aprH expression cassette comprising the $P_{amyL4199}/P_{short\ consensus\ amyQ}/P_{cryIIIA}$/cryIIIA stab promoter at the amyL locus. *Bacillus licheniformis* strain HyGe211 contains an aprH expression cassette comprising the $P_{amL4199}/P_{short\ consensus\ amyQ}/P_{cryIIIA}$/mod, cryIIIA stab promoter at the amryL locus. The sequences of the aprH expression cassettes in HyGe210 and HyGe211 were confirmed by DNA sequencing of the PCR products.

Example 19

Evaluation of Triple Tandem Promoter Variants

*Bacillus licheniformis* strains HyGe210 and HyGe211 were cultivated in standard small fermentation tanks under conditions suitable for *Bacillus clausii* alkaline protease (AprH) production, using a medium comprising hydrolyzed potato protein and mineral salts with a sucrose feed. Whole broth samples were assayed for protease activity at various time points during fermentation.

Protease activity was measured according to the following procedure. Culture supernatants were diluted appropriately in sample buffer (0.01% TWEEN®, 100 mM TRIS pH 8.5) followed with a series dilution from 1-fold to ⅓-fold to ⅑- fold of the diluted sample. *Bacillus clausii* alkaline protease (AprH) standard (Novozymes A/S, Bagsværd, Denmark) was diluted in sample buffer using two-fold steps starting with a 0.625 NPU/m concentration and ending with a 0.078 NPU/ml concentration. A total of 20 μl of each dilution including standard was transferred to a 96-well flat-bottom plate. Two hundred microliters of a Suc-Ala-Ala-Pro-Phe-pNA substrate solution (100 mg of Suc-Ala-Ala-Pro-Phe-pNA per ml DMSO diluted 1:55.6 in 100 mM TRIS pH 8.5) was added to each well, and the plate was incubated at ambient temperature for 10 minutes. During the incubation the rate of the reaction was measured at 405 nm using a BIOMEK® 3000. Sample concentrations were determined by extrapolation from the generated standard curve.

Figure 17:
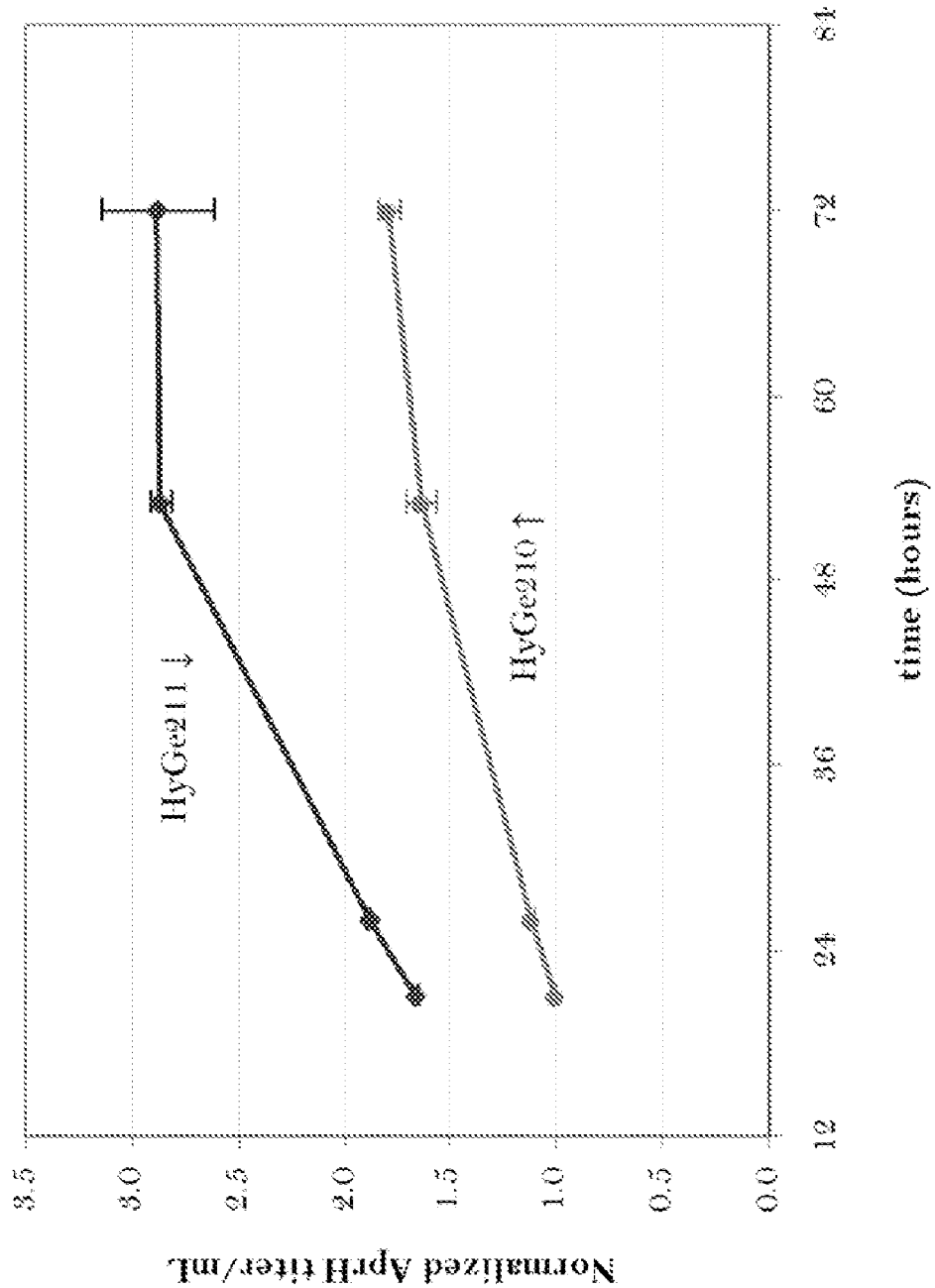
FIG. 17 shows the effect of triple tandem promoter variants on *Bacillus clausii* alkaline protease (AprH) production in *Bacillus licheniformis* strains HyGe210 and HyGe211.

The results are shown in FIG. 17. The results demonstrated that *Bacillus licheniformis* HyGe211, in which the protease was expressed from a triple promoter construct comprising a modified cryIIIA mRNA processing/stabilizing sequence, produced more protease than *Bacillus licheniformis* HyGe210, in which the protease was expressed from a triple promoter construct comprising an unmodified cryIIIA mRNA processing/stabilizing sequence. After the 72 hour fermentation, *Bacillus licheniformis* HyGe211 provided a 61% increase in comparison to *Bacillus licheniformis* HyGe210.

Example 20

Construction of pMDT100

Plasmid pMDT100 is an *E. coli* replicon containing the $P_{amyL4199}/P_{short\ consensus\ amyQ}/P_{cryIIIA}$/cryIIIAstab triple tandem promoter driving expression of the *Bacillus clausii* alkaline protease gene (aprH). This aprH expression cassette and the cat gene of pC194 (Horinouchi and Weisblum, 1982, *J. Bacteriol.* 150: 804-814) are flanked on both sides by fragments of the *Bacillus subtilis* alpha-amylase (amyE) gene, permitting insertion of the aprH expression cassette and cat gene at the amyE locus of the *Bacillus subtilis* chromosome by double homologous recombination via the two amyE fragments. Replacement of the aprH gene in pMDT100 with another gene allows chromosomal insertion and expression of that gene in *Bacillus subtilis*. The construction of pMDT100 is described below.

Figure 18:
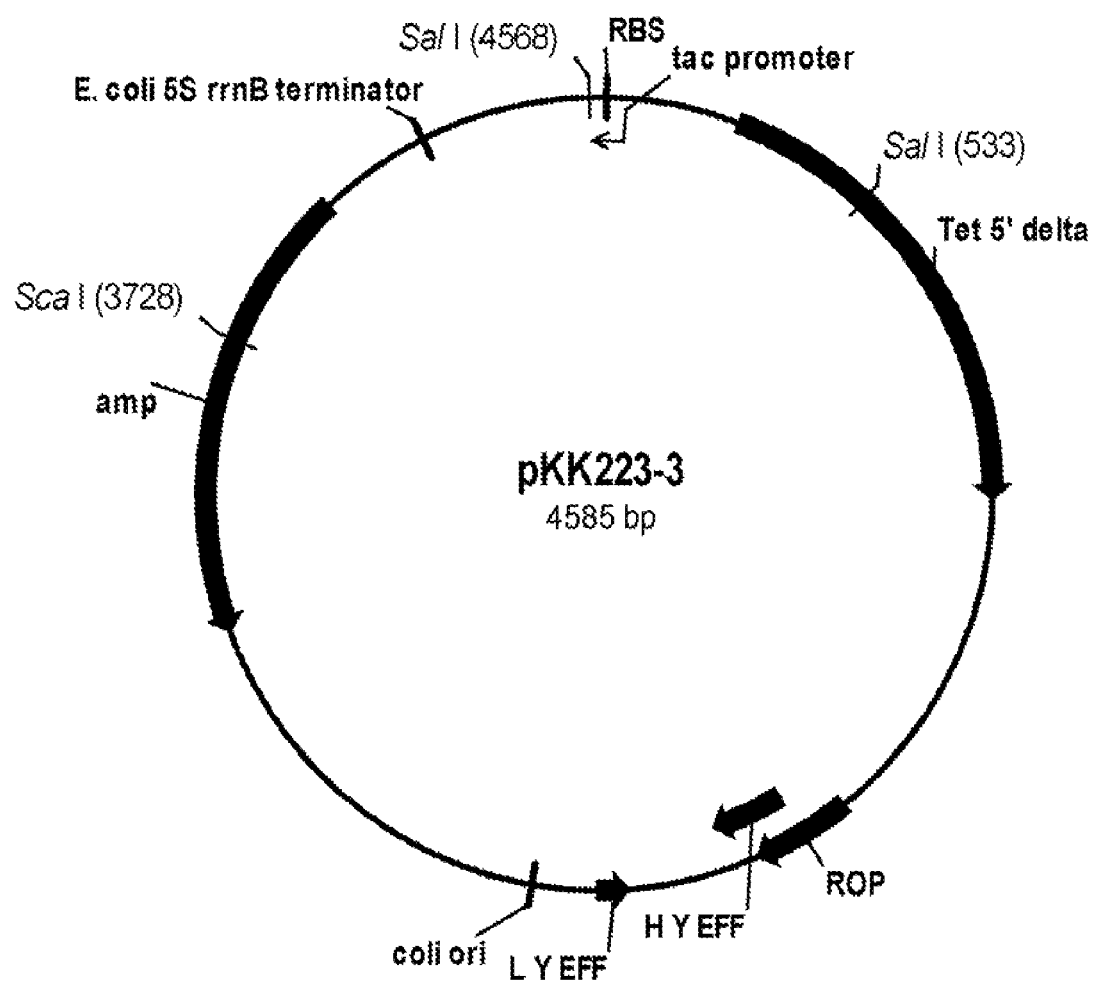
FIG. 18 shows a restriction map of pKK223-3.
Figure 19:
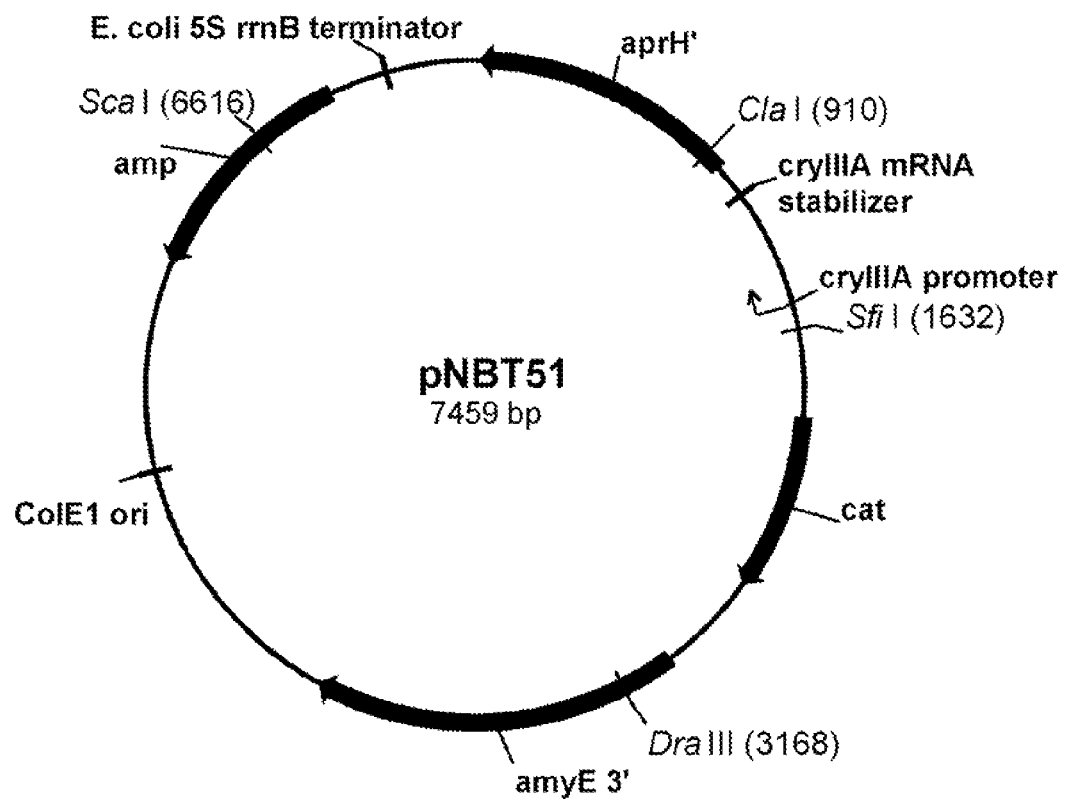
FIG. 19 shows a restriction map of pNBT51.

Plasmid pNBT51. Plasmid pNBT10 (pDG268MCS-Pr$_{cryIIIA}$/cryIIIAstab/SAV; U.S. Pat. No. 6,255,076) was isolated from *E. coli* DH5α as a host, using a QIAGEN® Plasmid Kit (QIAGEN Inc., Valencia, Calif., USA) according to the manufacturer's instructions, and digested with Cla I and Sca I. Cleavage occurred at the Cla I site at approximately codon 326 of the aprH coding sequence and not at the Cla I site at approximately codon 23, which was blocked by methylation due to *E. coli* Dam DNA methyltransferase. The Cla I ends were blunted using Klenow fragment (New England Biolabs, Inc., Beverly, Mass., USA) and dNTPs according to the manufacturer's instructions. The digested plasmid was analyzed by 0.8% agarose electrophoresis in TBE buffer, and a vector fragment of approximately 6615 bp was purified using a QIAQUICK® Gel Extraction Kit. Plasmid pOS4301 (Bacillus Genetic Stock Center, Ohio State University, Columbus, Ohio, USA) was digested with Sal I and Sca I, and the Sal I ends were blunted using Klenow fragment and dNTPs, as described above. The digested plasmid was analyzed by 0.8% agarose electrophoresis in TBE buffer, and a fragment of approximately 840 bp bearing the *E. coli* rrnB transcription terminator was purified using a QIAQUICK® Gel Extraction Kit. The same 840 bp Sal I/Sca I fragment could be isolated from the vector pKK223-3 (GE Healthcare, Piscataway, N.J., USA) (FIG. 18). The pNBT10 vector fragment and terminator-bearing fragment were ligated together with T4 DNA ligase (Roche Diagnostics Corporation, Indianapolis, Ind., USA) according to the manufacturer's instructions, and *E. coli* DH5α cells were transformed with the ligation according to the manufacturer's instructions, selecting for ampicillin resistance on 2×YT ampicillin plates at 37° C. The resulting plasmid was designated pNBT51 (pDG268-P$_{cryIIIA}$/cryIIIAstab/SAVΔ) (FIG. 19).

Figure 20:
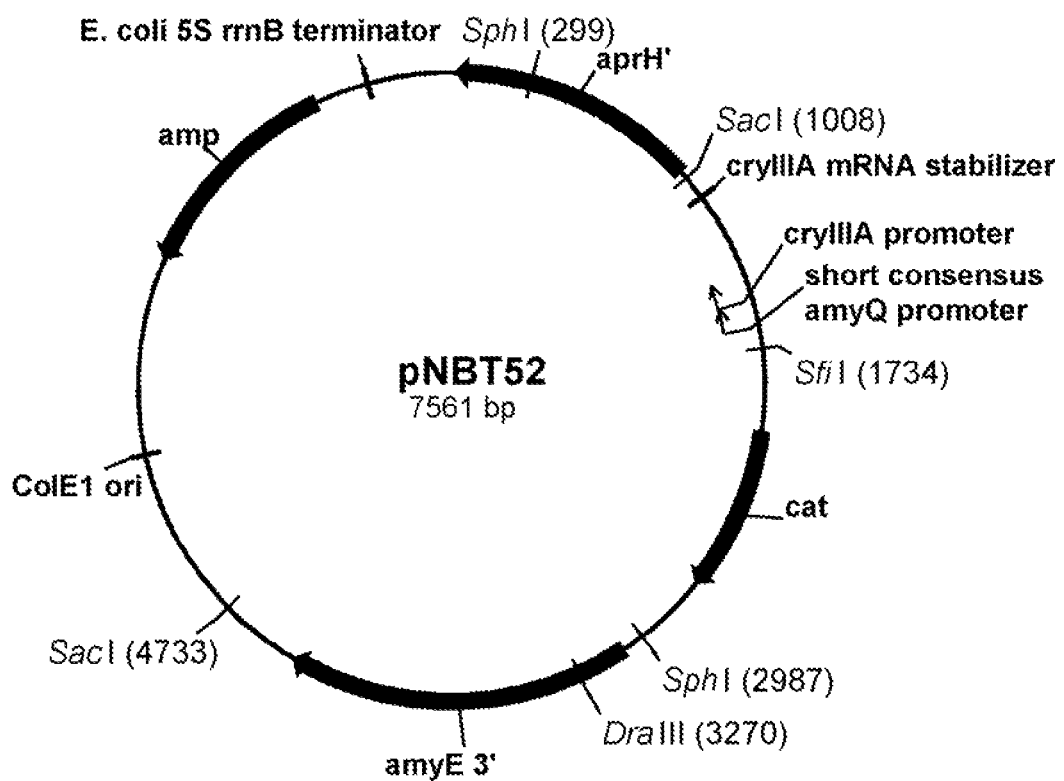
FIG. 20 shows a restriction map of pNBT52.

Plasmid pNBT52. Plasmid pNBT51 was digested with Sfi I, and the ends were blunted by incubation for 20 minutes at 11° C. with T4 DNA polymerase (Roche Diagnostics Corporation, Indianapolis, Ind., USA) and 25 μM of each dNTP, followed by heat-inactivation of the polymerase by incubation for 10 minutes at 75° C. The blunt-ended plasmid was then digested with Dra III and analyzed by 0.8% agarose electrophoresis in TBE buffer, and a vector fragment of approximately 5920 bp was purified using a QIAQUICK® Gel Extraction Kit. Plasmid pNBT20 (pDG268MCS-P$_{short\ consensus\ amyQ}$/SAV; U.S. Pat. No. 6,255,076) was digested with Dra III and Ecl 136II, and a fragment of approximately 1641 bp bearing a short consensus amyQ promoter (P$_{short\ consensus\ amyQ}$) was purified using a QIAQUICK® Gel Extraction Kit. The pNBT51 vector fragment and P$_{short\ consensus\ amyQ}$ fragment were ligated as described above, and *E. coli* DH5α cells were transformed with the ligation as described above, selecting for ampicillin resistance on 2×YT ampicillin plates at 37° C. Plasmid DNA was isolated from several transformants using a QIAPREP® 8 Miniprep Kit, digested with Sph I, and analyzed by 0.8% agarose electrophoresis in TBE buffer. One plasmid with expected restriction fragments of approximately 4873 bp and 2688 bp was designated pNBT52 (pDG268-P$_{short\ consensus\ amyQ}/P_{cryIIIA}$/cryIIIAstab/SAVΔ) (FIG. 20).

Figure 21:
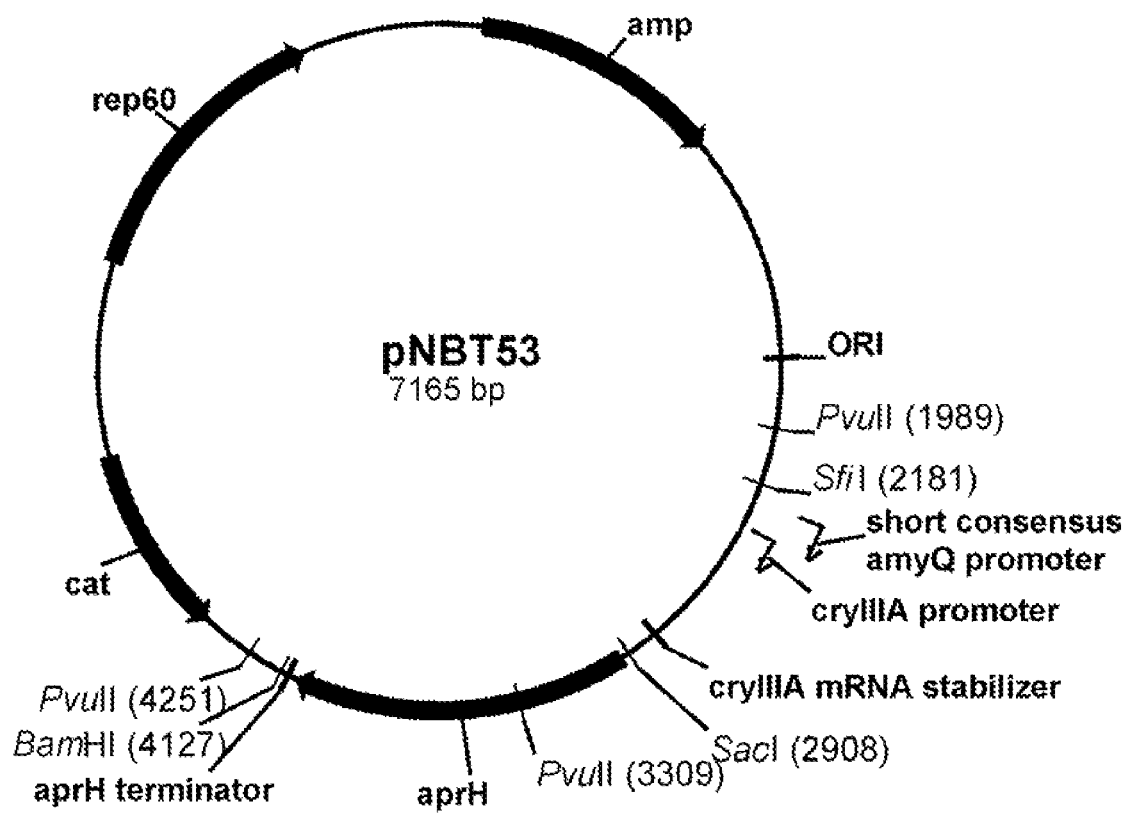
FIG. 21 shows a restriction map of pNBT53.

Plasmid pNBT53. Plasmid pNBT6 (pHP13amp-SAV: U.S. Pat. No. 6,255,076) was digested with Sfi I and Sac I and analyzed by 0.8% agarose electrophoresis in TBE buffer, and a vector fragment of approximately 6438 bp was purified using a QIAQUICK® Gel Extraction Kit. Plasmid pNBT52 was digested with Sfi I and Sac I and analyzed by 0.8% agarose electrophoresis in TBE buffer, and a fragment of approximately 727 bp bearing the P$_{short\ consensus\ amyQ}/P_{cryIIIA}$/cryIIIAstab tandem promoter was purified using a QIAQUICK® Gel Extraction Kit. The pNBT6 vector fragment and P$_{short\ consensus\ amyQ}/P_{cryIIIA}$/cryIIIAstab fragment were ligated as described above, and *E. coli* DH5α cells were transformed with the ligation as described above, selecting for ampicillin resistance on 2×YT ampicillin plates at 37° C. Plasmid DNA was isolated from several transformants using a QIAPREP® 8 Miniprep Kit, digested with Pvu II, and analyzed by 0.8% agarose electrophoresis using TBE buffer. One plasmid with expected restriction fragments of approximately 4903 bp, 1320 bp, and 942 bp was designated pNBT53 (pHP13 amp-P$_{short\ consensus\ amyQ}/P_{cryIIIA}$/cryIIIAstab/SAV) (FIG. 21).

Figure 22:
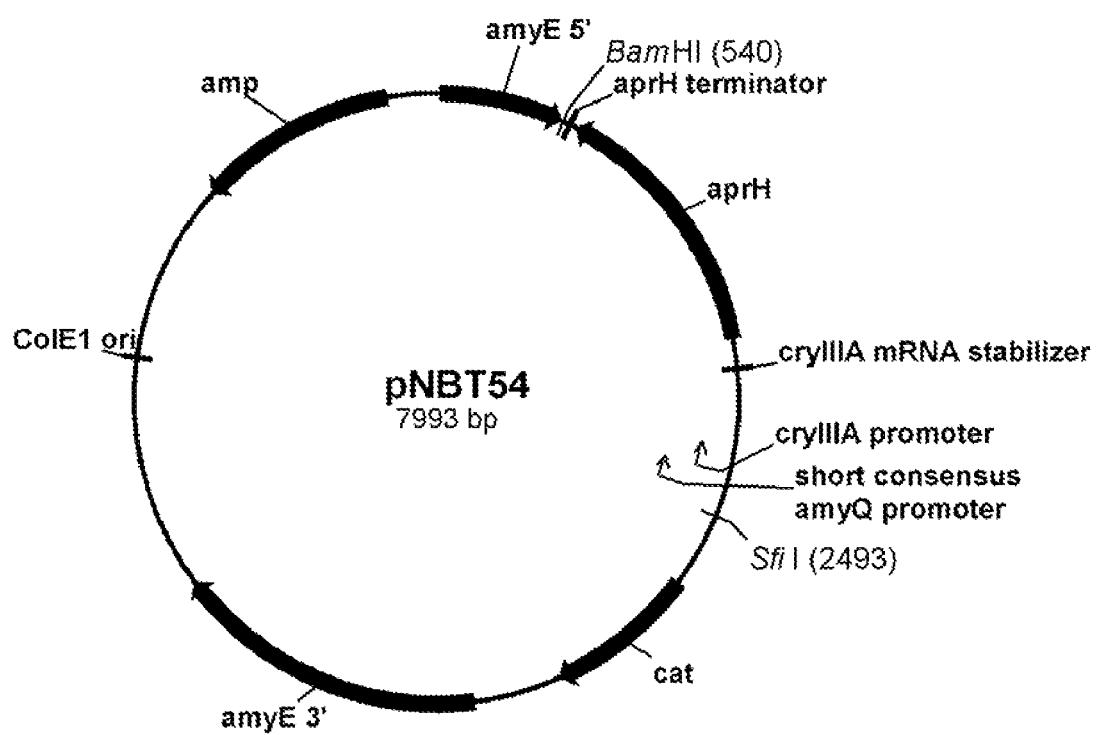
FIG. 22 shows a restriction map of pNBT54.

Plasmid pNBT54. Plasmid pNBT1 (pDG268MCS; U.S. Pat. No. 6,255,076) was digested with Sfi I and Bam HI and analyzed by 0.8% agarose electrophoresis in TBE buffer, and a vector fragment of approximately 6040 bp was purified using a QIAQUICK® Gel Extraction Kit. Plasmid pNBT53 was digested with Sfi I and Bam HI and analyzed by 0.8% agarose electrophoresis in TBE buffer, and a fragment of approximately 1953 bp bearing the P$_{short\ consensus\ amyQ}/P_{cryIIIA}$/cryIIIAstab/SAV cassette was purified using a QIAQUICK® Gel Extraction Kit. The pNBT1 vector fragment and P$_{short\ consensus\ amyQ}/P_{cryIIIA}$/cryIIIAstab/SAV fragment were ligated as described above, and *E. coli* DH5α cells were transformed with the ligation as described above, selecting for ampicillin resistance on 2×YT ampicillin plates at 37° C. Plasmid DNA was isolated from several transformants using a QIAPREP® 8 Miniprep Kit and analyzed by simultaneous digestion with Sfi I and Bam HI followed by 0.8% agarose gel electrophoresis in TBE buffer. One plasmid with expected restriction fragments of approximately 6040 bp and 1953 bp was designated pNBT54 (pDG268MCS-P$_{short\ consensus\ amyQ}$/P$_{cryIIIA}$/cryIIIAstab/SAV) (FIG. 22).

Figure 23:
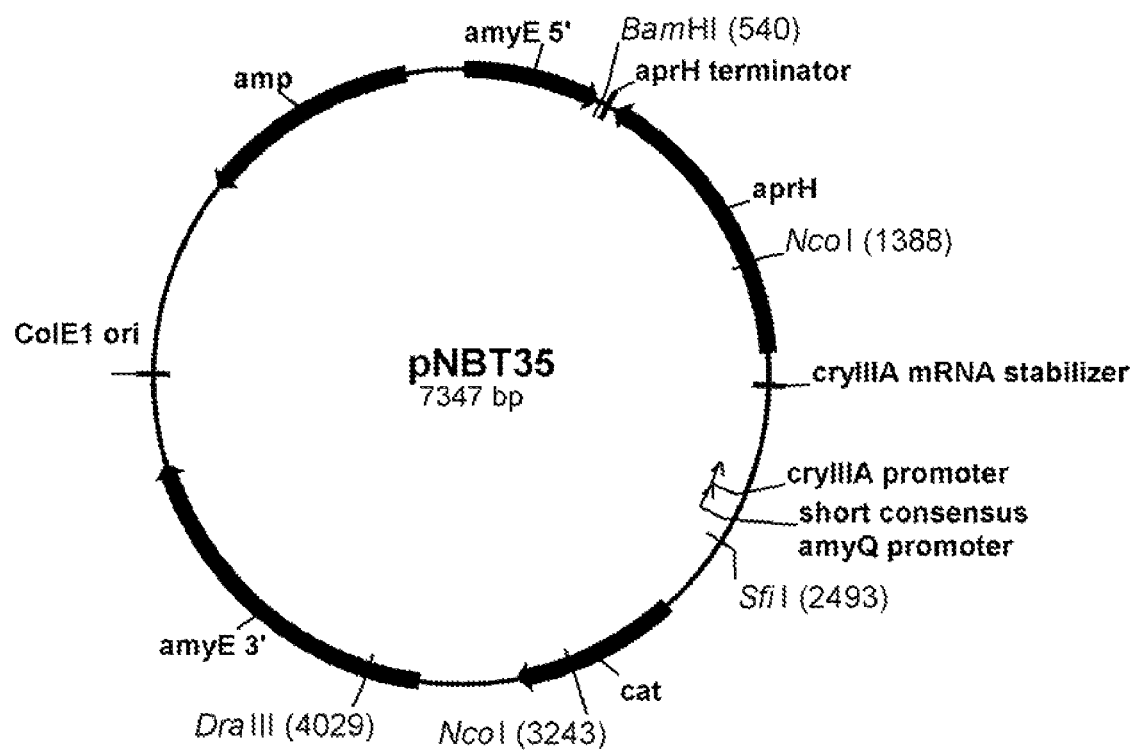
FIG. 23 shows a restriction map of pNBT35.

Plasmid pNBT35. Plasmid pNBT2 (pDG268MCSA-Pr$_{cryIIIA}$/cryIIIAstab/SAV; U.S. Pat. No. 6,255,076) was digested with Sfi I and Bam HI and analyzed by 0.8% agarose gel electrophoresis in TBE buffer, and a vector fragment of approximately 5394 bp was purified using a QIAQUICK® Gel Extraction Kit, Plasmid pNBT54 was digested with Sfi I and Bam HI, and analyzed by 0.8% agarose gel electrophoresis in TBE buffer, and a fragment of approximately 1953 bp bearing the P$_{short\ consensus\ amyQ}$/P$_{cryIIIA}$/cryIIIAstab/SAV cassette was purified using a QIAQUICK® Gel Extraction Kit. The pNBT2 vector fragment and P$_{short\ consensus\ amyQ}$/P$_{cryIIIA}$/cryIIIAstab/SAV fragment were ligated as described above, and *E. coli* DH5α cells were transformed with the ligation as described above, selecting for ampicillin resistance on 2×YT ampicillin plates at 37° C. Plasmid DNA was isolated from several transformants using a QIAPREP® 8 Miniprep Kit, digested with Nco I, and analyzed by 0.8% agarose gel electrophoresis in TBE buffer. One plasmid with expected restriction fragments of approximately 5492 bp and 1855 bp was designated pNBT35 (pDG268MCSΔ-P$_{short\ consensus\ amyQ}$/P$_{cryIIIA}$/cryIIIAstab/SAV) (FIG. 23).

Plasmid pNBT30. Plasmid pNBT30 was constructed to contain a PCR clone of the amyL4199 variant of the amyL gene promoter (U.S. Pat. No. 6,100,063). *Bacillus licheniformis* SJ1904 genomic DNA was isolated according to the procedure of Pitcher et al., 1989, supra. The amyL4199 promoter (P$_{amyL4199}$) gene was amplified by PCR from *Bacillus licheniformis* SJ1904 genomic DNA using primers 950872 and 991151 shown below. Primer 950872 incorporates an Sfi I restriction site, and primer 991151 incorporates a Sac I restriction site and the variant nucleotides of P$_{amyL4199}$.

```
Primer 950872:                      (SEQ ID NO: 21)
5'-CCAGGCCTTAAGGGCCGCATGCGTCCTTCTTTGTGCT-3'

Primer 991151:                      (SEQ ID NO: 22)
5'-GAGCTCCTTTCAATGTGATACATATGA-3'
```

The PCR was performed using AMPLITAQ® Gold DNA Polymerase (Applied Biosystems, Foster City, Calif., USA) according to manufacturer's recommendations, except that the MgCl$_2$ concentration was 3 mM, rather than the standard 1.5 mM. The amplification reaction (50 µl) was composed of 10 mM Tris-HCl (pH 8.3), 50 mM KCl, 3.0 mM MgCl$_2$. 200 µM of each dNTP, 0.5 µM of each primer, 0.25 units of AMPLITAQ® Gold DNA Polymerase, and approximately 200 ng of template DNA. The PCR was performed in a ROBOCYCLER® 40 Temperature Cycler programmed for 1 cycle at 95° C. for 9 minutes; 30 cycles each at 95° C. for 1 minute, 55° C. for 1 minute, and 72° C. for 1 minute; and 1 cycle at 72° C. for 3 minutes.

Figure 24:
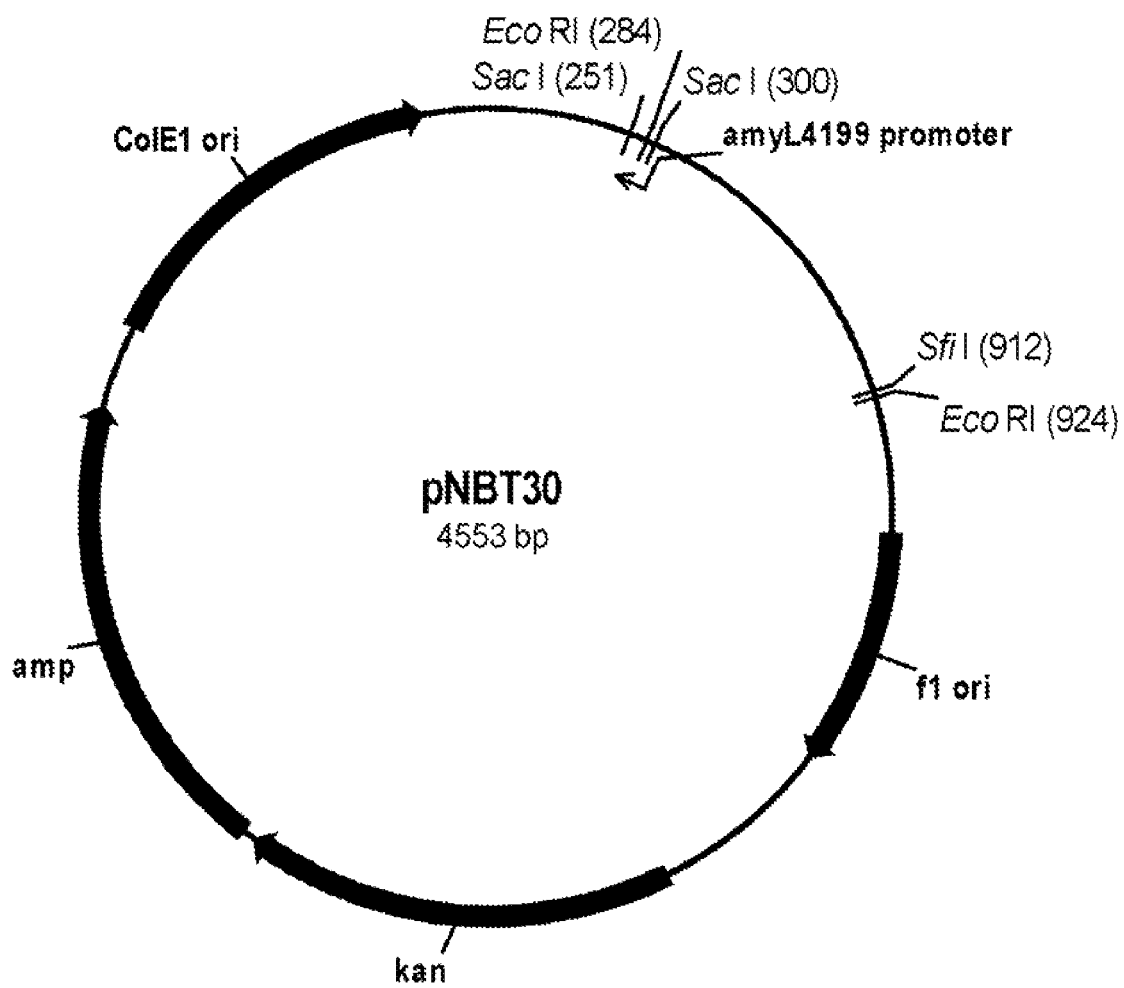
FIG. 24 shows a restriction map of pNBT30.

The resulting PCR product of approximately 625 bp was cloned into vector pCR2.1 using a TOPO® TA Cloning Kit and transformed into ONE SHOT® TOP10 Chemically Competent *E. coli* cells according to the manufacturer's instructions. Plasmid DNA was isolated from several transformants using a QIAPREP® 8 Miniprep Kit and analyzed for the presence of the cloned PCR fragment by digestion with Eco RI followed by 0.8% agarose electrophoresis in TBE buffer. One plasmid with expected restriction fragments of approximately 3913 bp and 640 bp was designated pNBT30 (pCR2.1-amyL4199) (FIG. 24). The DNA sequence of the cloned PCR fragment was confirmed by DNA sequencing.

Figure 25:
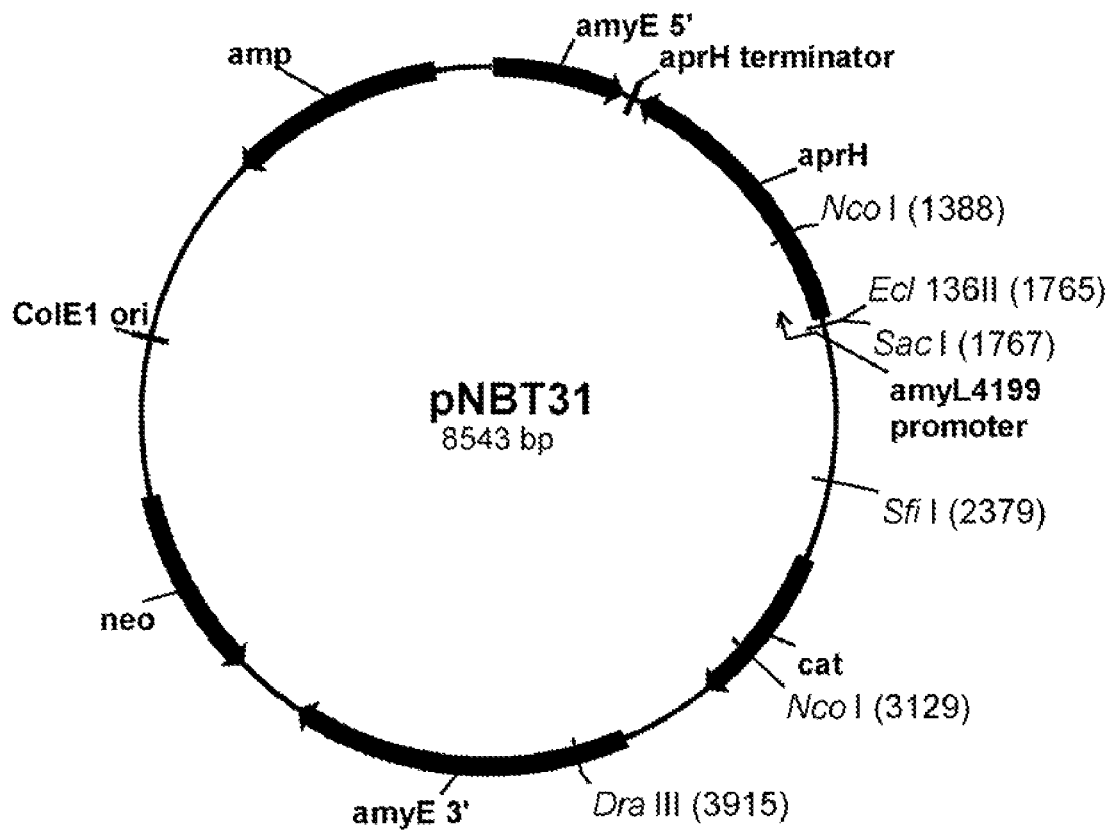
FIG. 25 shows a restriction map of pNBT31.

Plasmid pNBT31. Plasmid pNBT3 (pDG268MCSΔneo-Pr$_{cryIIIA}$/cryIIIAstab/SAV; U.S. Pat. No. 6,255,076) was digested with Sfi I and Sac I and analyzed by 0.8% agarose electrophoresis in TBE buffer, and a vector fragment of approximately 7931 bp was purified using a QIAQUICK® Gel Extraction Kit. Plasmid pNBT30 was digested with Sfi I and Sac I, analyzed by 0.8% agarose electrophoresis in TBE buffer, and a fragment of approximately 612 bp bearing P$_{amyL4199}$ was purified using a QIAQUICK® Gel Extraction Kit. The pNBT3 vector fragment and P$_{amyL4199}$ fragment were ligated as described above, and *E. coli* XL1-Blue cells (Stratagene Corporation, La Jolla, Calif., USA) were transformed with the ligation according to the manufacturer's instructions, selecting for ampicillin resistance on 2×YT ampicillin plates at 37° C. Plasmid DNA was isolated from several transformants using a QIAPREP® 8 Miniprep Kit, digested with Nco I, and analyzed by 0.8% agarose electrophoresis in TBE buffer. One plasmid with expected restriction fragments of approximately 6802 bp and 1741 bp was designated pNBT31 (FIG. 25).

Figure 26:
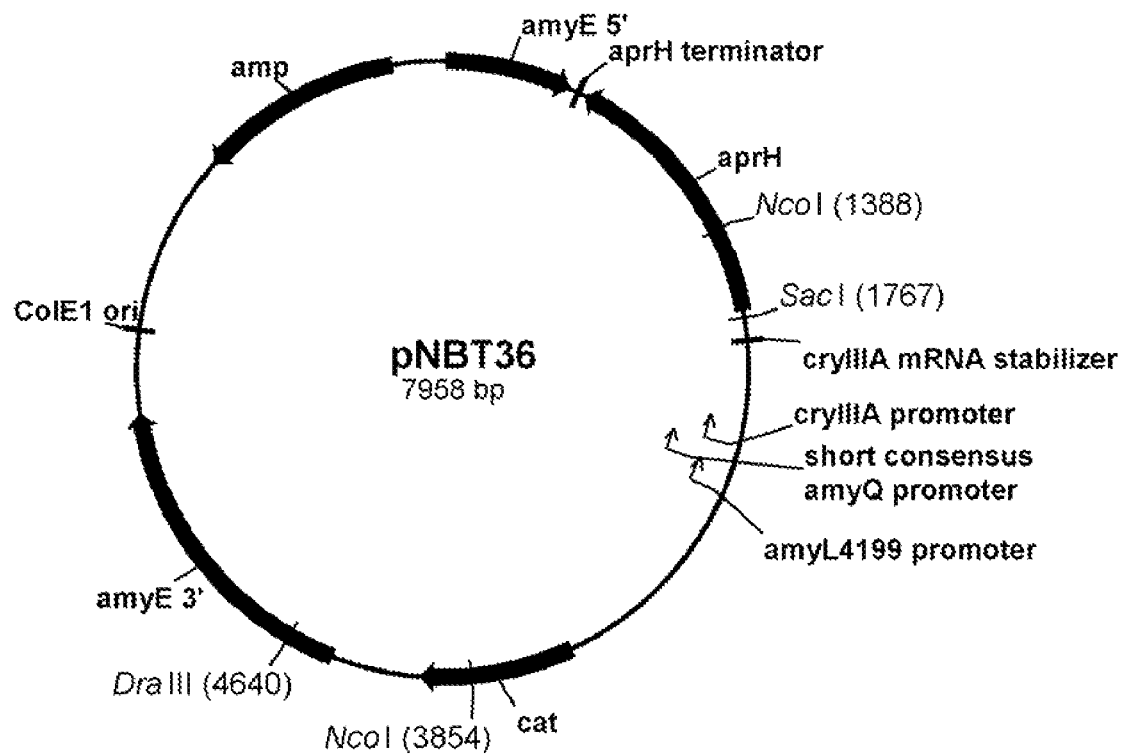
FIG. 26 shows a restriction map of pNBT36.

Plasmid pNBT36. Plasmid pNBT35 was digested with Sfi I, and the ends were blunted using T4 DNA polymerase and dNTPs, as described above. The blunt ended plasmid was then digested with Dra III, and analyzed by 0.8% agarose electrophoresis in TBE buffer. A vector fragment of approximately 5808 bp was purified using a QIAQUICK® Gel Extraction Kit. Plasmid pNBT31 was digested with Dra III and Ecl 136II, analyzed by 0.8% agarose electrophoresis in TBE buffer, and a fragment of approximately 2150 bp bearing P$_{amyL4199}$ was purified using a QIAQUICK® Gel Extraction Kit. The pNBT35 vector fragment and P$_{amyL4199}$ fragment were ligated as described above, and *E. coli* SURE® cells (Stratagene Corporation, La Jolla, Calif., USA) were transformed with the ligation according to the manufacturer's instructions, selecting for ampicillin resistance on 2×YT ampicillin plates at 37° C. Plasmid DNA was isolated from several transformants using a QIAPREP® 8 Miniprep Kit, digested with Nco I, and analyzed by 0.8% agarose electrophoresis in TBE buffer. One plasmid with expected restriction fragments of approximately 5492 bp and 2466 bp was designated pNBT36 (FIG. 26).

Figure 27:
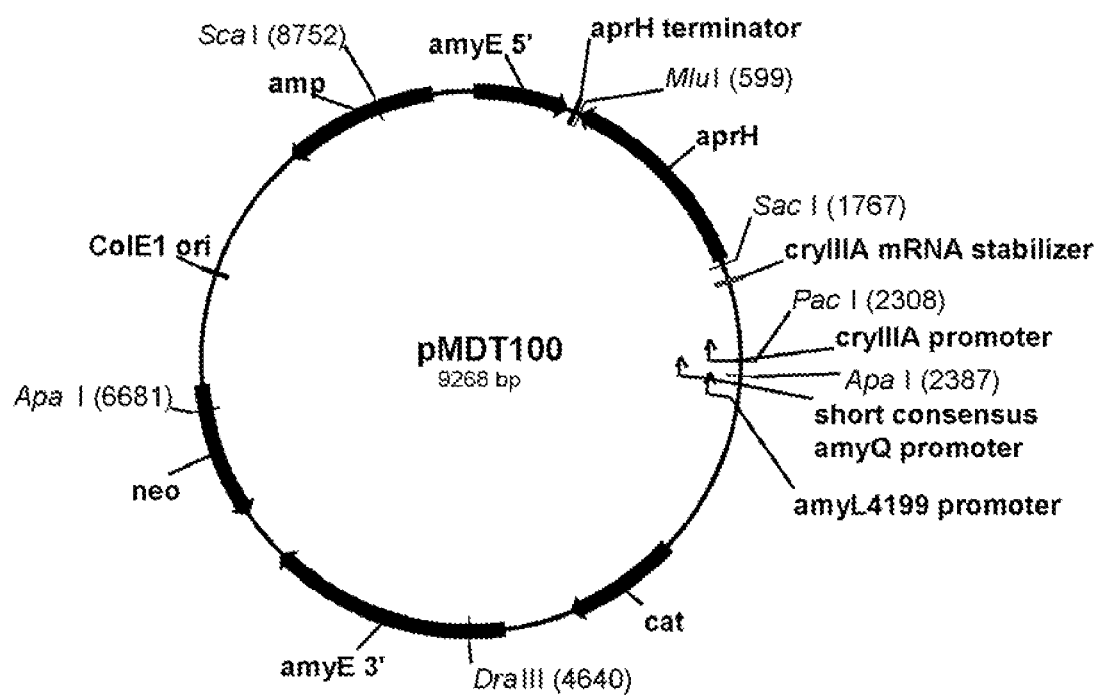
FIG. 27 shows a restriction map of pMDT100.

Plasmid pMDT100. Plasmid pNBT13 (pDG268Δneo-P$_{amyL}$/P$_{cryIIIA}$/cryIIIAstab/SAV; U.S. Pat. No. 6,255,076) was digested with Dra III and Sac I, and a vector fragment of approximately 6395 bp was purified using a QIAQUICK® Gel Extraction Kit. Plasmid pNBT36 was digested with Dra III and Sac I, analyzed by 0.8% agarose electrophoresis in TBE buffer, and a fragment of approximately 2873 bp bearing the P$_{aamyL4199}$/P$_{amyQ(sc)}$/P$_{cryIIIA}$ triple tandem promoter was purified using a QIAQUICK® Gel Extraction Kit. The pNBT13 vector fragment and P$_{amyL4199}$/P$_{amyQ(sc)}$/P$_{cryIIIA}$ fragment were ligated as described above, and *E. coli* SURE® cells were transformed with the ligation as described above, selecting for ampicillin resistance on 2×YT ampicillin plates at 37° C. Plasmid DNA was isolated from several transformants using a QIAPREP® 8 Miniprep Kit, digested with Apa I, and analyzed by 0.8% agarose electrophoresis in TBE buffer. One plasmid with expected restriction fragments of approximately 4974 bp and 4294 bp was designated pMDT100 (FIG. 27).

Plasmid pMDT100 was linearized by digestion with Sca I. *Bacillus subtilis* 168Δ4 was transformed with the linearized plasmids according to the procedure of Anagnostopoulos and Spizizen, 1961, supra, and transformants were selected for chloramphenicol resistance on TBAB chloramphenicol plates at 37° C. Chloramphenicol-resistant transformants were screened for protease production by patching colonies onto TBAB milk plates and scoring for clearing zones and also for neomycin sensitivity by patching colonies onto TBAB neomycin plates at 37° C. to confirm that the DNA had inserted into the amyE gene of the *Bacillus subtilis* chromosome by double crossover. A chloramphenicol resistant, neomycin sensitive, protease-producing transformant (with the $P_{amyL4199}/P_{short\ consensus\ amyQ}/P_{cryIIIA}$/cryIIIA stab/aprH cassette inserted at the amyE locus) was identified and designated *Bacillus subtilis* MDT130.

Example 21

Construction of pMDT174

Figure 28:
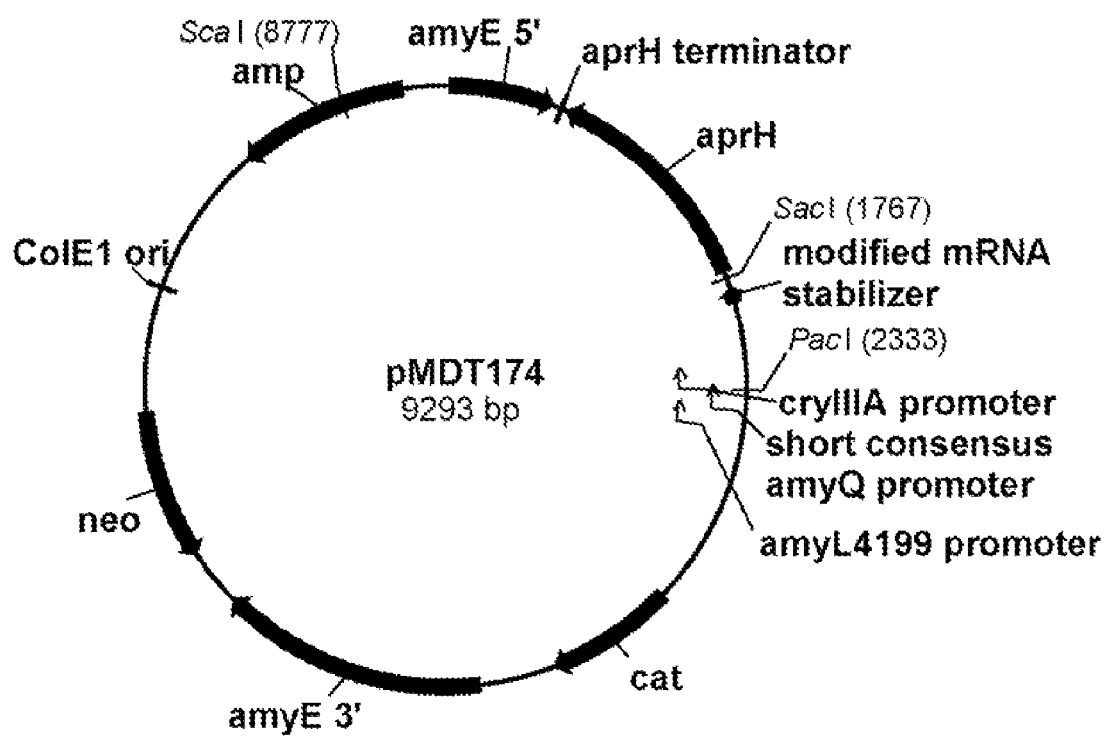
FIG. 28 shows a restriction map of pMDT174.

Plasmids pMDT100 and pGME080 were digested with Pac I and Sac I. The digested plasmids were analyzed by 0.8% agarose electrophoresis in TBE buffer, and an approximately 8727 bp vector fragment of pMDT100 and an approximately 566 bp fragment of pGME080 bearing the modified cryIIIA stabilizer were purified using a QIAQUICK® Gel Extraction Kit. The purified fragments were ligated together with T4 DNA ligase as described above, and *E. coli* XL10-GOLD® Ultracompetent cells were transformed with the ligation according to manufacturer's instructions. Plasmid DNA from several transformants was purified using a BIOROBOT® 9600 and tested by digestion with Fnu 4HI followed by 0.8% agarose electrophoresis in TBE buffer. Digestion of the desired ligation product was expected to produce approximately 36 fragments, including an approximately 912 bp fragment not expected from pMDT100 and excluding an approximately 1045 bp fragment expected for pMDT100. One plasmid with such a restriction pattern was designated pMDT174 (FIG. 28), which contains an aprH expression cassette comprising a triple tandem promoter with a modified cryIIIA mRNA processing/stabilizing sequence ($P_{amyL4199}/P_{short\ consensus\ amyQ}/P_{cryIIIA}$/mod. cryIIIA stab)

Plasmid pMDT100 was linearized by digestion with Sca I. *Bacillus subtilis* 168Δ4 was transformed with the linearized plasmids according to the procedure of Anagnostopoulos and Spizizen, 1961, supra, and transformants were selected for chloramphenicol resistance on TBAB chloramphenicol plates at 37° C. Chloramphenicol-resistant transformants were screened for protease production by patching colonies onto TBAB milk plates and scoring for clearing zones and also for neomycin sensitivity by patching colonies onto TBAB neomycin plates at 37° C. to confirm that the DNA had inserted into the amyE gene of the *Bacillus subtilis* chromosome by double crossover. A chloramphenicol resistant, neomycin sensitive, protease-producing transformant (with the $P_{amyL4199}/P_{short\ consensus\ amyQ}/P_{cryIIIA}$/mod. cryIIIA stab/aprH cassette inserted at the amyE locus) was identified and designated *Bacillus subtilis* MDT131.

Example 22

Evaluation of Triple Tandem Promoter Variants in *Bacillus subtilis*

Plasmids pMDT100 and pMDT174 were linearized by digestion with Sca I. *Bacillus subtilis* 168Δ4 was transformed with the linearized plasmids according to the procedure of Anagnostopoulos and Spizizen, 1961, supra, and transformants were selected for chloramphenicol resistance on TBAB chloramphenicol plates at 37° C. Chloramphenicol-resistant transformants were screened for protease production by patching colonies onto TBAB milk plates and scoring for clearing zones and also for neomycin sensitivity by patching colonies onto TBAB neomycin plates at 37° C. to confirm that the DNA had inserted into the amyE gene of the *Bacillus subtilis* chromosome by double crossover. Chloramphenicol resistant, neomycin sensitive, protease-producing transformants were identified; one derived from pMDT100 (with the $P_{amyL4199}/P_{short\ consensus\ amyQ}/P_{cryIIIA}$/cryIIIA stab/aprH cassette inserted at the amyE locus) was designated *Bacillus subtilis* MDT130, and one derived from pMDT100 (with the $P_{amyL4199}/P_{short\ consensus\ amyQ}/P_{cryIIIA}$/mod. cryIIIA stab/aprH cassette inserted at the amyE locus) was designated *Bacillus subtilis* MDT131.

Genomic DNA was isolated from *Bacillus subtilis* strains MDT130 and MDT131 according to the procedure of Pitcher et al., 1989, supra. *Bacillus subtilis* A164Δ5 (U.S. Pat. No. 5,891,701) was transformed with the genomic DNAs according to the procedure of Anagnostopoulos and Spizizen, 1961, supra, and transformants were selected for chloramphenicol resistance on TBAB chloramphenicol plates at 37° C. One transformant derived from MDT130 DNA (with the $P_{amyL4199}/P_{short\ consensus\ amyQ}/P_{cryIIIA}$/cryIIIA stab/aprH cassette inserted at the amyE locus) was designated MDT134; one derived from MDT131 DNA (with the $P_{amyL4199}/P_{short\ consensus\ amyQ}/P_{cryIIIA}$/mod. cryIIIA stab/aprH cassette inserted at the amyE locus) was designated MDT135.

*Bacillus subtilis* strains MDT134 and MDT135 were grown at 37° C. in triplicate in 250 ml shake flasks containing 50 ml of PS-1 medium. Samples were removed at 3, 4, and 5 days, and whole broths were assayed for protease activity as described above.

Figure 29:
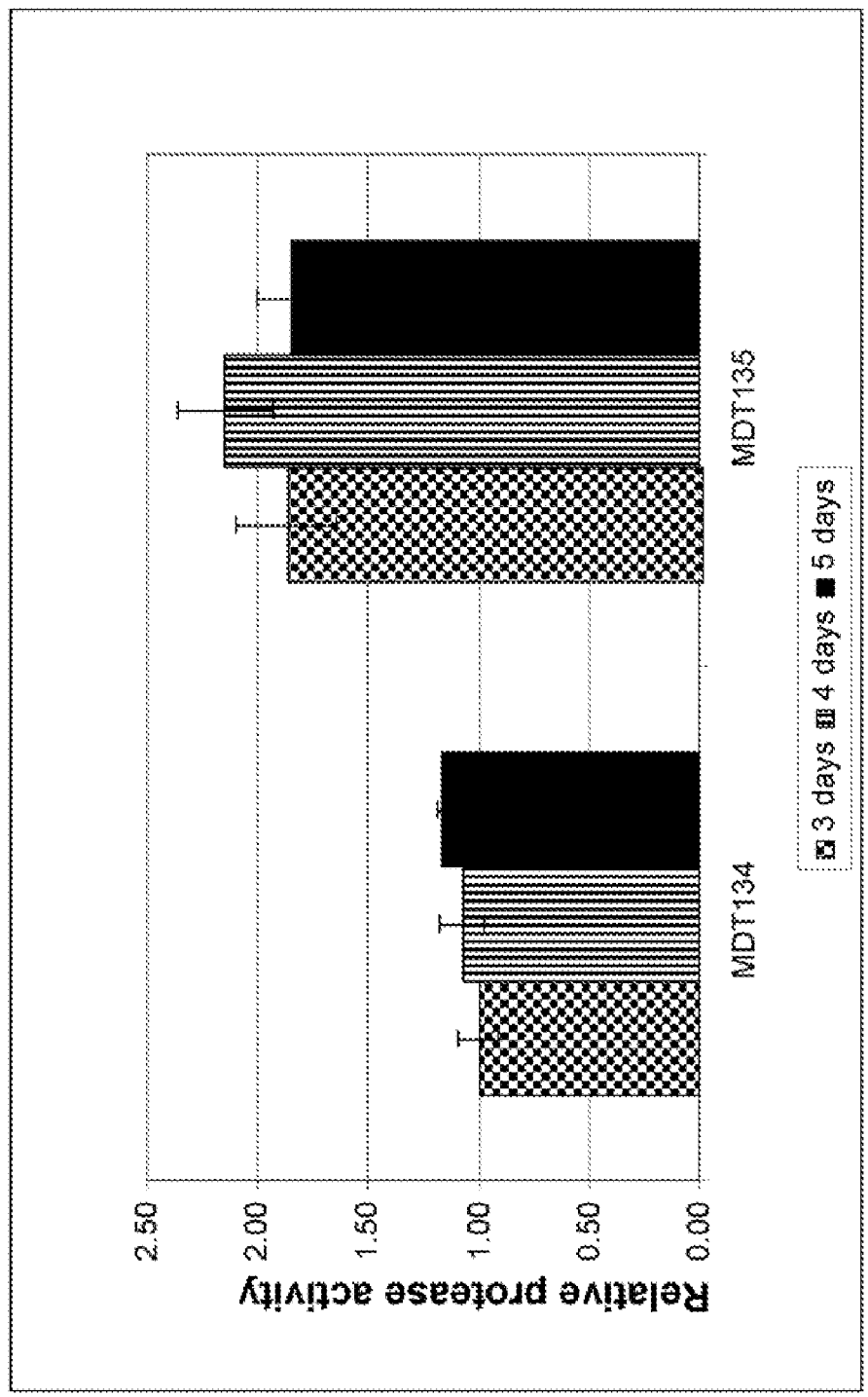
FIG. 29 shows the relative protease activity of *Bacillus subtilis* strains MDT134 and MDT135.

The results are shown in FIG. 29. The results demonstrated that *Bacillus subtilis* MDT135, in which the protease was expressed from a triple promoter construct comprising a modified cryIIIA mRNA processing/stabilizing sequence, produced more protease than *Bacillus subtilis* MDT134, in which the protease was expressed from a triple promoter construct comprising an unmodified cryIIIA mRNA processing/stabilizing sequence, in comparison to *Bacillus subtilis* MDT134, *Bacillus subtilis* MDT135 provided an 87% increase after three days, a 100% increase after 4 days, and a 58% increase after 5 days.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for producing a polypeptide having biological activity in a bacterial host cell, comprising:
   (a) cultivating the bacterial host cell in a medium conducive for production of the polypeptide having biological activity, wherein the bacterial host cell comprises one or more copies of a nucleic acid construct comprising a promoter region operably linked to a polynucleotide sequence encoding the polypeptide having biological activity and a modified mRNA processing/stabilizing sequence located downstream of the promoter region and upstream of the ribosome binding site of the polynucleotide sequence encoding the polypeptide having biological activity, wherein the modified mRNA processing/stabilizing sequence is a cryIIIA mRNA processinq/stabilizing sequence comprising at least one additional copy of a Shine-Dalgarno sequence or a SP82 mRNA processing/stabilizing sequence comprising at least one additional copy of a Shine-Dalgamo sequence; and wherein the modified mRNA processing/stabilizing sequence promotes higher expression of the polynucleotide sequence compared to an unmodified mRNA processing/stabilizing sequence; and
   (b) isolating the polypeptide having biological activity from the cultivation medium.

2. The method of claim 1, wherein the bacterial host cell is a *Bacillus* cell.

3. A bacterial cell comprising a nucleic acid construct that comprises one or more copies of a nucleic acid construct comprising a promoter region operably linked to a polynucleotide sequence encoding the polypeptide having biological activity and a modified mRNA processing/stabilizing sequence located downstream of the promoter region and upstream of the ribosome binding site of the polynucleotide sequence encoding the polypeptide having biological activity, wherein the modified mRNA processing/stabilizing sequence is a cryIIIA mRNA processinq/stabilizinq sequence comprising at least one additional copy of a Shine-Dalqarno sequence or a SP82 mRNA processinq/stabilizinq sequence comprising at least one additional copy of a Shine-Dalqarno sequence; and wherein the modified mRNA processinq/stabilizinq sequence promotes higher expression of the polynucleotide sequence compared to an unmodified mRNA processing/stabilizing sequence.

4. The bacterial cell of claim 3, which is a *Bacillus* cell.

5. A method for producing a selectable marker-free mutant of a bacterial cell, comprising deleting a selectable marker gene of the bacterial cell, wherein the bacterial cell comprises one or more copies of a nucleic acid construct comprising a promoter region operably linked to a polynucleotide sequence encoding the polypeptide having biological activity and a modified mRNA processing/stabilizing sequence located downstream of the promoter region and upstream of the ribosome binding site of the polynucleotide sequence encoding the polypeptide having biological activity, wherein the modified mRNA processing/stabilizing sequence is a cryIIIA mRNA processinq/stabilizinq sequence comprising at least one additional copy of a Shine-Dalqarno sequence or a SP82 mRNA processinq/stabilizinq sequence comprising at least one additional copy of a Shine-Dalqarno sequence; and wherein the modified mRNA processinq/stabilizinq sequence promotes higher expression of the polynucleotide sequence compared to an unmodified mRNA processing/stabilizing sequence.

6. The method of claim 5, wherein the bacterial host cell is a *Bacillus* cell.

7. A method for obtaining a bacterial host cell, comprising introducing into a bacterial host cell one or more copies of a nucleic acid construct comprising a promoter region operably linked to a polynucleotide sequence encoding the polypeptide having biological activity and a modified mRNA processing/stabilizing sequence located downstream of the promoter region and upstream of the ribosome binding site of the polynucleotide sequence encoding the polypeptide having biological activity, wherein the modified mRNA processing/stabilizing sequence is a cryIIIA mRNA processing/stabilizing sequence comprising at least one additional copy of a Shine-Dalqarno sequence or a SP82 mRNA processing/stabilizing sequence comprising at least one additional copy of a Shine-Dalgarno sequence; and wherein the modified mRNA processing/stabilizing sequence promotes higher expression of the polynucleotide sequence compared to an unmodified mRNA processing/stabilizing sequence.

8. The method of claim 7, wherein the bacterial host cell is a *Bacillus* cell.

9. The method of claim 1, wherein the modified mRNA processing/stabilizing sequence is a cryIIIA mRNA processing/stabilizing sequence comprising at least one additional copy of a Shine-Dalgarno sequence.

10. The method of claim 1, wherein the modified mRNA processing/stabilizing sequence is a SP82 mRNA processing/stabilizing sequence comprising at least one additional copy of a Shine-Dalgarno sequence.

11. The method of claim 1, wherein the at least one additional copy of a Shine-Dalgarno sequence comprises the sequence GGAG.

12. The method of claim 1, wherein the at least one additional copy of a Shine-Dalgarno sequence comprises the sequence GGAGG.

13. The method of claim 1, wherein the at least one additional copy of a Shine-Dalgarno sequence comprises SEQ ID NO: 1.

14. The bacterial cell of claim 3, wherein the modified mRNA processing/stabilizing sequence is a cryIIIA mRNA processing/stabilizing sequence comprising at least one additional copy of a Shine-Dalgarno sequence.

15. The bacterial cell of claim 3, wherein the modified mRNA processing/stabilizing sequence is a SP82 mRNA processing/stabilizing sequence comprising at least one additional copy of a Shine-Dalgarno sequence.

16. The bacterial cell of claim 3, wherein the at least one additional copy of a Shine-Dalgarno sequence comprises the sequence GGAG.

17. The bacterial cell of claim 3, wherein the at least one additional copy of a Shine-Dalgarno sequence comprises the sequence GGAGG.

18. The bacterial cell of claim 3, wherein the at least one additional copy of a Shine-Dalgarno sequence comprises SEQ ID NO: 1.

19. The method of claim 5, wherein the modified mRNA processing/stabilizing sequence is a cryIIIA mRNA processing/stabilizing sequence comprising at least one additional copy of a Shine-Dalgarno sequence.

20. The method of claim 5, wherein the modified mRNA processing/stabilizing sequence is a SP82 mRNA processing/stabilizing sequence comprising at least one additional copy of a Shine-Dalgarno sequence.

21. The method of claim 5, wherein the at least one additional copy of a Shine-Dalgarno sequence comprises the sequence GGAG.

22. The method of claim 5, wherein the at least one additional copy of a Shine-Dalgarno sequence comprises the sequence GGAGG.

23. The method of claim 5, wherein the at least one additional copy of a Shine-Dalgarno sequence comprises SEQ ID NO: 1.

24. The method of claim 7, wherein the modified mRNA processing/stabilizing sequence is a cryIIIA mRNA processing/stabilizing sequence comprising at least one additional copy of a Shine-Dalgarno sequence.

25. The method of claim 7, wherein the modified mRNA processing/stabilizing sequence is a SP82 mRNA processing/stabilizing sequence comprising at least one additional copy of a Shine-Dalgarno sequence.

26. The method of claim 7, wherein the at least one additional copy of a Shine-Dalgarno sequence comprises the sequence GGAG.

27. The method of claim 7, wherein the at least one additional copy of a Shine-Dalgarno sequence comprises the sequence GGAGG.

28. The method of claim 7, wherein the at least one additional copy of a Shine-Dalgarno sequence comprises SEQ ID NO: 1.

* * * * *

SEQUENCE LISTING

<160> NUMBER OF SEQ ID NOS: 22

<210> SEQ ID NO 1
<211> LENGTH: 10
<212> TYPE: DNA
<213> ORGANISM: Bacillus thuringiensis

<400> SEQUENCE: 1
agaaaggagg                                                            10

<210> SEQ ID NO 2
<211> LENGTH: 25
<212> TYPE: DNA
<213> ORGANISM: Bacillus thuringiensis

<400> SEQUENCE: 2
agaaaggagg tgatccagcc gcacc                                           25

<210> SEQ ID NO 3
<211> LENGTH: 28
<212> TYPE: DNA
<213> ORGANISM: Bacillus thuringiensis

<400> SEQUENCE: 3
tagaaaggag gtgatccagc cgcacctt                                        28

<210> SEQ ID NO 4
<211> LENGTH: 546
<212> TYPE: DNA
<213> ORGANISM: Bacillus thuringiensis

<400> SEQUENCE: 4
agcttaatta aagataatat ctttgaattg taacgcccct caaaagtaag aactacaaaa      60
aaagaatacg ttatatagaa atatgtttga accttcttca gattacaaat atattcggac     120
ggactctacc tcaaatgctt atctaactat agaatgacat acaagcacaa ccttgaaaat     180
ttgaaaatat aactaccaat gaacttgttc atgtgaatta tcgctgtatt taattttctc     240
aattcaatat ataatatgcc aatacattgt tacaagtaga aattaagaca cccttgatag     300
ccttactata cctaacatga tgtagtatta aatgaatatg taaatatatt tatgataaga     360
agcgacttat ttataatcat tacatatttt tctattggaa tgattaagat tccaatagaa     420
tagtgtataa attatttatc ttgaaaggag ggatgcctaa aaacgaagaa cattaaaaac     480
atatatttgc accgtctaat ggatttatga aaaatcattt tatcagtttg aaaattatgt     540
attatg                                                               546

<210> SEQ ID NO 5
<211> LENGTH: 571
<212> TYPE: DNA
<213> ORGANISM: Bacillus subtilis

<400> SEQUENCE: 5
agcttaatta aagataatat ctttgaattg taacgcccct caaaagtaag aactacaaaa      60
aaagaatacg ttatatagaa atatgtttga accttcttca gattacaaat atattcggac     120
ggactctacc tcaaatgctt atctaactat agaatgacat acaagcacaa ccttgaaaat     180
ttgaaaatat aactaccaat gaacttgttc atgtgaatta tcgctgtatt taattttctc     240
aattcaatat ataatatgcc aatacattgt tacaagtaga aattaagaca cccttgatag     300

```
ccttactata cctaacatga tgtagtatta aatgaatatg taaatatatt tatgataaga    360
agcgacttat ttataatcat tacatatttt tctattggaa tgattaagat tccaatagaa    420
tagtgtataa attatttatc ttgaaaggag ggatgcctaa aaacgaagaa cattaaaaac    480
atatatttgc accgtctaat ggatagaaag gaggtgatcc agccgcacct tatgaaaaat    540
cattttatca gtttgaaaat tatgtattat g                                   571
```

<210> SEQ ID NO 6
<211> LENGTH: 42
<212> TYPE: DNA
<213> ORGANISM: Artificial
<220> FEATURE:
<223> OTHER INFORMATION: Bacillus thuringensis
<400> SEQUENCE: 6

```
ggagccgctg agctaccaca gattgtgaaa ggagaggtta ac                       42
```

<210> SEQ ID NO 7
<211> LENGTH: 97
<212> TYPE: DNA
<213> ORGANISM: Bacillus thuringiensis
<400> SEQUENCE: 7

```
cgggccttaa gggccctcga acgtaagat gaaaccttag ataaaagtgc ttttttttgtt    60 gacattgaag aattattaat gttataatta attaagg                             97
```

<210> SEQ ID NO 8
<211> LENGTH: 97
<212> TYPE: DNA
<213> ORGANISM: Bacillus thuringiensis
<400> SEQUENCE: 8

```
ccttaattaa ttataacatt aataattctt caatgtcaac aaaaaaagca cttttatcta    60
aggtttcatc ttacgtttcg agggccctta aggcccg                             97
```

<210> SEQ ID NO 9
<211> LENGTH: 21
<212> TYPE: DNA
<213> ORGANISM: Bacillus thuringiensis
<400> SEQUENCE: 9

```
cgggccttaa gggccctcga a                                              21
```

<210> SEQ ID NO 10
<211> LENGTH: 20
<212> TYPE: DNA
<213> ORGANISM: Bacillus thuringiensis
<400> SEQUENCE: 10

```
ccttaattaa ttataacatt                                                20
```

<210> SEQ ID NO 11
<211> LENGTH: 20
<212> TYPE: DNA
<213> ORGANISM: Bacillus thuringiensis
<400> SEQUENCE: 11

```
agcttaatta aagataatat                                                20
```

<210> SEQ ID NO 12
<211> LENGTH: 40
<212> TYPE: DNA

```
<213> ORGANISM: Bacillus thuringiensis

<400> SEQUENCE: 12
ggctggatca cctcctttct atccattaga cggtgcaaat                                40

<210> SEQ ID NO 13
<211> LENGTH: 45
<212> TYPE: DNA
<213> ORGANISM: Bacillus clausii

<400> SEQUENCE: 13
agaaaggagg tgatccagcc gcaccttatg aaaaatcatt ttatc                          45

<210> SEQ ID NO 14
<211> LENGTH: 20
<212> TYPE: DNA
<213> ORGANISM: Bacillus clausii

<400> SEQUENCE: 14
aagcttgcgc caccacgaat                                                      20

<210> SEQ ID NO 15
<211> LENGTH: 24
<212> TYPE: DNA
<213> ORGANISM: Bacillus licheniformis

<400> SEQUENCE: 15
gaattcgacg gcttcccgtg cgcc                                                 24

<210> SEQ ID NO 16
<211> LENGTH: 28
<212> TYPE: DNA
<213> ORGANISM: Bacillus licheniformis

<400> SEQUENCE: 16
aagcttccat tcaaacctgg tgaggaag                                             28

<210> SEQ ID NO 17
<211> LENGTH: 24
<212> TYPE: DNA
<213> ORGANISM: Bacillus licheniformis

<400> SEQUENCE: 17
gcggccgctc gctttccaat ctga                                                 24

<210> SEQ ID NO 18
<211> LENGTH: 31
<212> TYPE: DNA
<213> ORGANISM: Bacillus licheniformis

<400> SEQUENCE: 18
atcgataata atttatacac tattctattg g                                         31

<210> SEQ ID NO 19
<211> LENGTH: 37
<212> TYPE: DNA
<213> ORGANISM: Bacillus licheniformis

<400> SEQUENCE: 19
ccaggcctta agggccgcat gcgtccttct ttgtgct                                   37

<210> SEQ ID NO 20
<211> LENGTH: 20
<212> TYPE: DNA
```

```
<213> ORGANISM: Bacillus licheniformis

<400> SEQUENCE: 20
cgacttcctc ttcctcagag                                               20

<210> SEQ ID NO 21
<211> LENGTH: 37
<212> TYPE: DNA
<213> ORGANISM: Bacillus licheniformis

<400> SEQUENCE: 21
ccaggcctta agggccgcat gcgtccttct ttgtgct                            37

<210> SEQ ID NO 22
<211> LENGTH: 27
<212> TYPE: DNA
<213> ORGANISM: Bacillus licheniformis

<400> SEQUENCE: 22
gagctccttt caatgtgata catatga                                       27
```